(12) United States Patent
Jin et al.

(10) Patent No.: US 10,265,051 B2
(45) Date of Patent: Apr. 23, 2019

(54) PROBE FOR ULTRASONIC IMAGING APPARATUS AND METHOD FOR MANUFACTURING THE SAME

(71) Applicant: SAMSUNG MEDISON CO., LTD., Gangwon-Do (KR)

(72) Inventors: Gil-Ju Jin, Seoul (KR); Jung-Lim Park, Seongnam-si (KR)

(73) Assignee: SAMSUNG MEDISON CO., LTD., Hongcheon-Gun, Gangwon-do (KR)

( * ) Notice: Subject to any disclaimer, the term of this patent is extended or adjusted under 35 U.S.C. 154(b) by 582 days.

(21) Appl. No.: 14/673,693

(22) Filed: Mar. 30, 2015

(65) Prior Publication Data
US 2016/0066885 A1 Mar. 10, 2016

(30) Foreign Application Priority Data

Sep. 4, 2014 (KR) .......................... 10-2014-0117965

(51) Int. Cl.
*A61B 8/00* (2006.01)
*H01R 13/502* (2006.01)
(Continued)

(52) U.S. Cl.
CPC .......... *A61B 8/4444* (2013.01); *B06B 1/0622* (2013.01); *B60R 16/0222* (2013.01);
(Continued)

(58) Field of Classification Search
CPC . A61B 8/4444; B06B 1/0622; B60R 16/0222; B60R 16/03
(Continued)

(56) References Cited

U.S. PATENT DOCUMENTS

2001/0041837 A1* 11/2001 Takeuchi .............. B06B 1/0622
600/437
2002/0073781 A1 6/2002 Hashimoto et al.
(Continued)

OTHER PUBLICATIONS

European Search Report issued in Application No. 15156651.0 dated Apr. 29, 2016.
(Continued)

*Primary Examiner* — Bryan P Gordon
(74) *Attorney, Agent, or Firm* — Morgan Lewis & Bockius LLP

(57) ABSTRACT

A probe of an ultrasonic imaging apparatus and a method for manufacturing the same are disclosed. The probe for an ultrasonic imaging apparatus includes a piezoelectric unit including a piezoelectric substance and an electrode; a printed circuit board (PCB) unit having a printed circuit board (PCB), configured to be formed at a lateral surface of the piezoelectric unit; a matching layer formed at front surfaces of the piezoelectric unit and the PCB unit; and a backing layer formed at a back surface of the piezoelectric unit and the PCB unit. The probe and a method for manufacturing the probe can reduce a variation of ultrasonic acoustic characteristics caused by a printed circuit board (PCB) because the PCB is not arranged among a piezoelectric substance, a matching layer, and a backing layer. A PCB is provided at a lateral surface of the piezoelectric substance, so that strength against impact can be increased either during channel division based on dicing or during the usage time of a probe. In addition, a single crystal (monocrystal) may be used as a piezoelectric substance or the like, such that a probe having a large bandwidth can be formed, and low-frequency ultrasonic signals and high-frequency ultrasonic signals can be transmitted and received. In addition, the probe and the method for manufacturing the same can easily perform channel division of the acoustic module, and make
(Continued)

the divided acoustic module using a curvature, and thus can be applied to various technical fields without being limited to the shapes of probes.

20 Claims, 50 Drawing Sheets

(51) Int. Cl.
    *B60R 16/02*     (2006.01)
    *B60R 16/03*     (2006.01)
    *B06B 1/06*     (2006.01)

(52) U.S. Cl.
    CPC ......... *B60R 16/03* (2013.01); *H01R 13/5025* (2013.01); *A61B 2560/0468* (2013.01); *A61B 2562/166* (2013.01); *B06B 1/0685* (2013.01); *H01R 13/502* (2013.01)

(58) Field of Classification Search
    USPC ........................................................ 310/334
    See application file for complete search history.

(56) References Cited

U.S. PATENT DOCUMENTS

| | | | |
|---|---|---|---|
| 2008/0238262 A1* | 10/2008 | Takeuchi | B06B 1/0622 310/346 |
| 2008/0312537 A1 | 12/2008 | Hyuga | |
| 2009/0034370 A1 | 2/2009 | Guo | |
| 2010/0103637 A1* | 4/2010 | Jin | A61B 8/4483 361/777 |
| 2010/0176688 A1* | 7/2010 | Jin | A61B 8/00 310/327 |
| 2011/0105906 A1* | 5/2011 | Lee | A61B 8/4281 600/459 |
| 2011/0316389 A1 | 12/2011 | Kwon et al. | |
| 2013/0231566 A1 | 9/2013 | Jin et al. | |

OTHER PUBLICATIONS

European Office Action issued in Application No. 15 156 651.0 dated Mar. 29, 2018.

* cited by examiner

FIG. 2
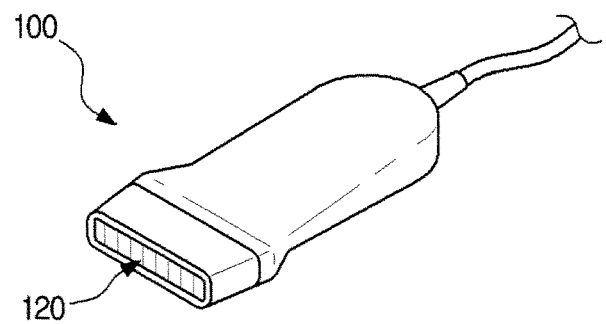
(a)
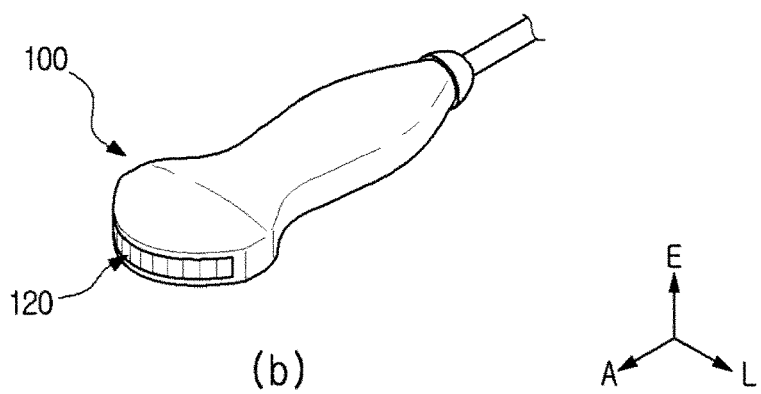
(b)
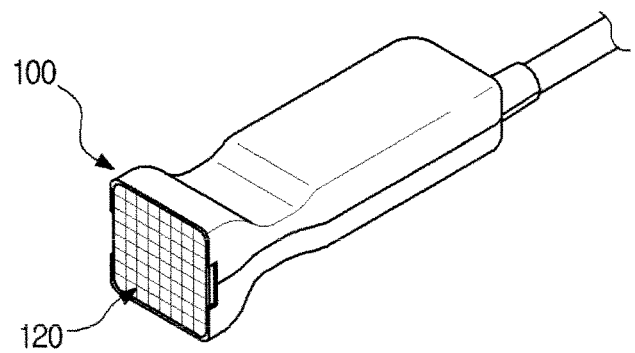
(c)

110: 120, 130a, 130b
210: 220, 260

FIG. 7
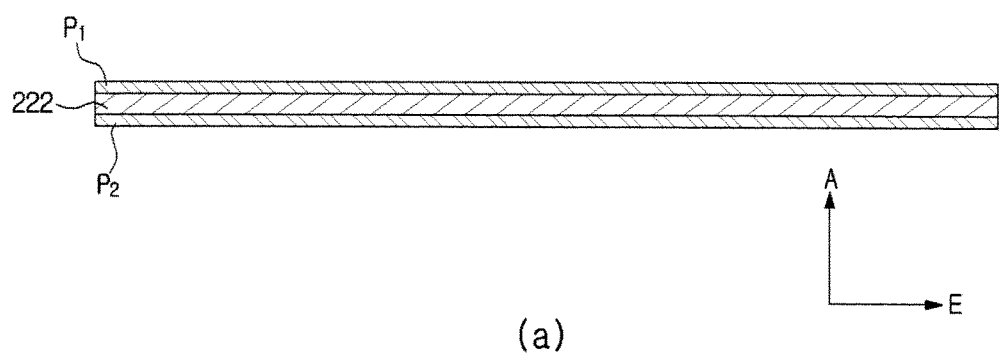
(a)
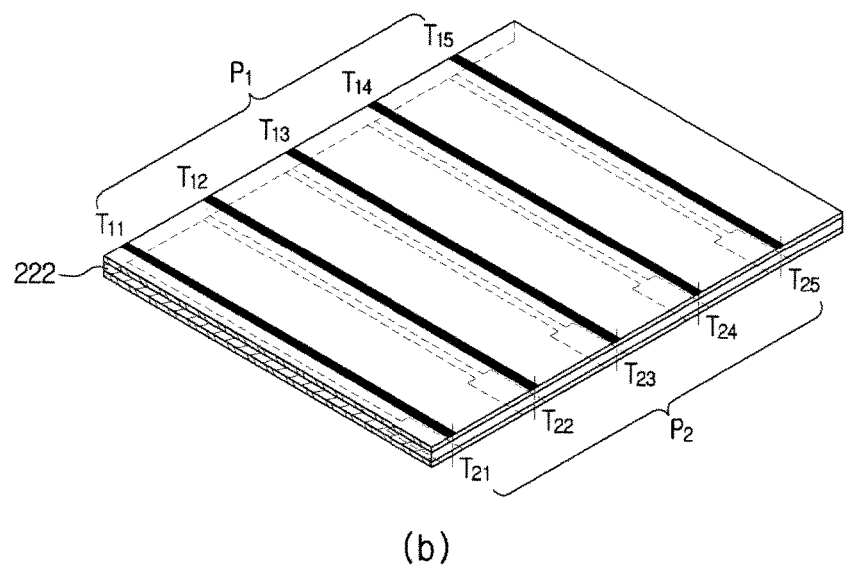
(b)

110: 120, 130a, 130b
310: 321a, 321b, 322, 360

FIG. 30
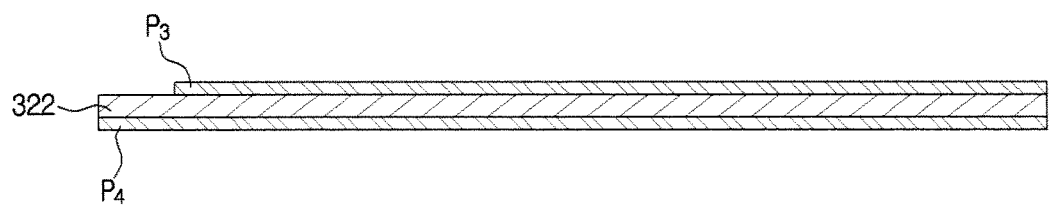
(a)
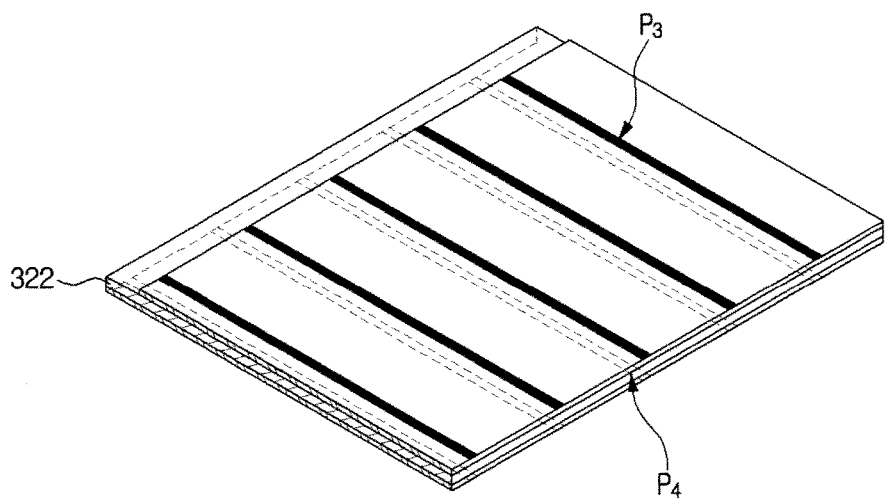
(b)

FIG. 31
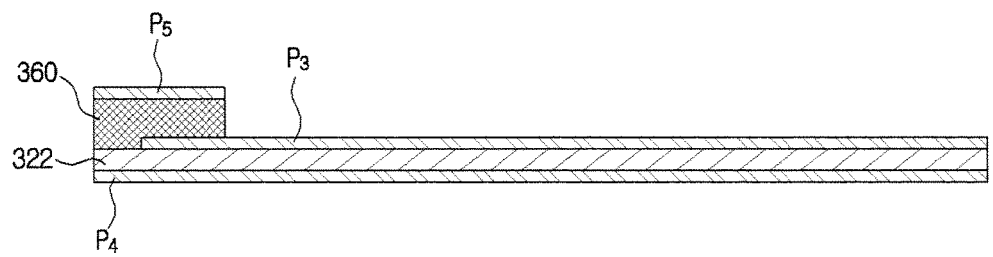
(a)
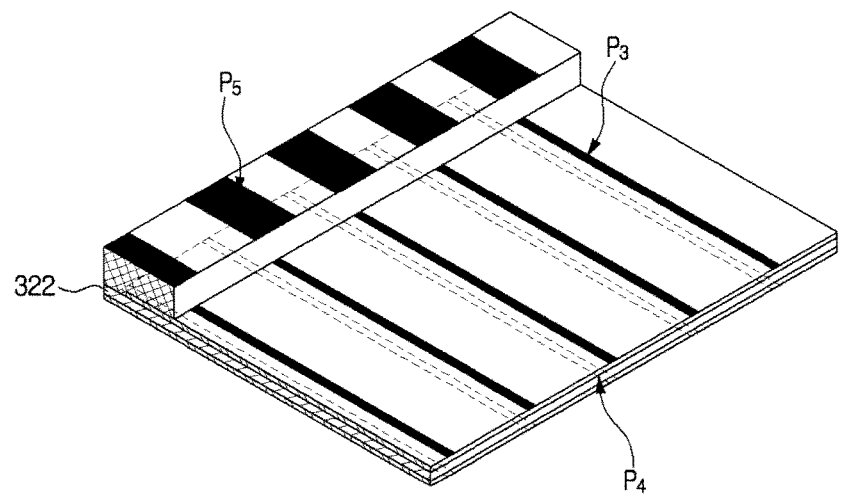
(b)

FIG. 32
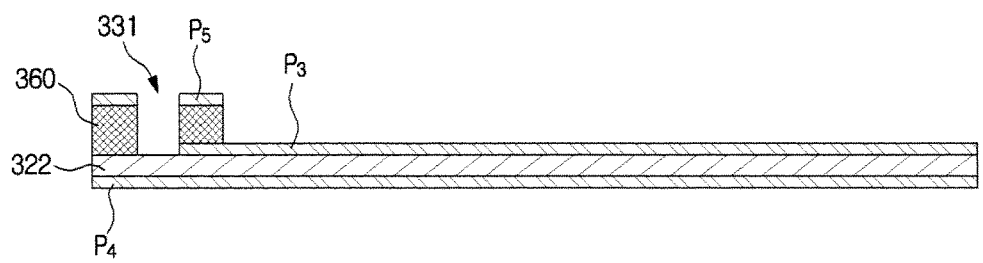
(a)
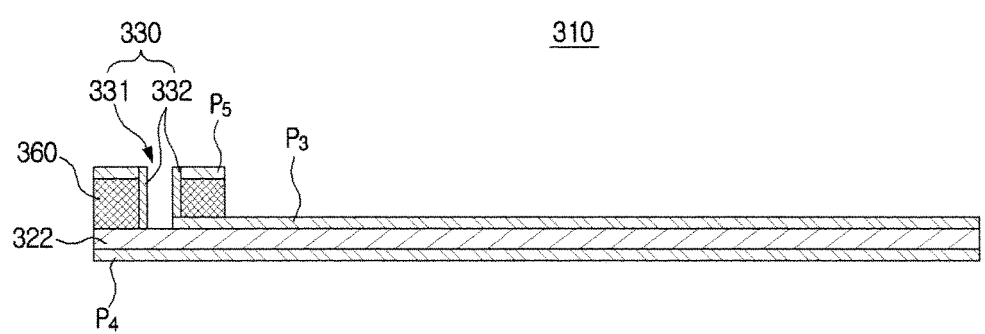
(b)

FIG. 50
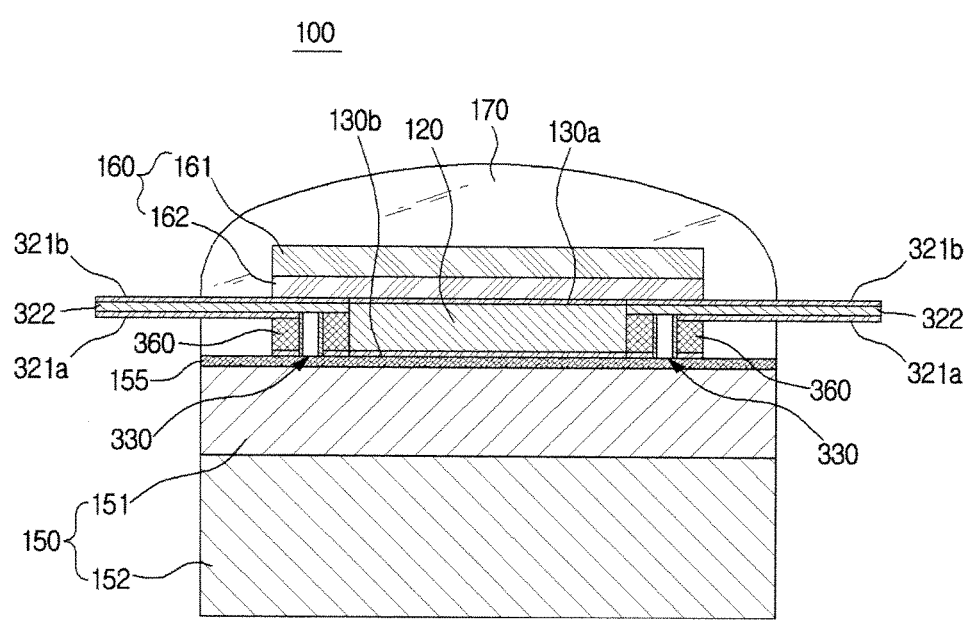
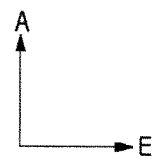

PROBE FOR ULTRASONIC IMAGING APPARATUS AND METHOD FOR MANUFACTURING THE SAME

CROSS-REFERENCE TO RELATED APPLICATION

This application claims the benefit of Korean Patent Application No. 10-2014-0117965, filed on Sep. 4, 2014 in the Korean Intellectual Property Office, the disclosure of which is incorporated herein by reference.

BACKGROUND

1. Field

Embodiments of the present invention relate to a probe, and more particularly to a probe for an ultrasonic imaging apparatus so as to generate images of the inside of a target object using ultrasonic waves, and a method for manufacturing the same.

2. Description of the Related Art

An ultrasonic imaging apparatus applies an ultrasonic signal from the surface of an object (for example, a human body) to a target site of the inside of the body of the object, acquires tomograms of soft tissues or images regarding blood flow using information of reflected ultrasonic signals (ultrasonic echo signals), and provides information regarding a necessary target part to be diagnosed.

The ultrasonic imaging apparatus, as compared to other image diagnostic apparatuses, such as an X-ray diagnostic apparatus, computerized tomography (CT) scanner, a magnetic resonance imaging (MRI) apparatus, and a nuclear medical diagnostic apparatus, has compact size and low price, non-invasive and non-destructive characteristics. Accordingly, the ultrasonic imaging apparatus has been widely utilized for cardiac, abdominal, and urologic diagnosis as well as obstetric and gynecological diagnosis.

The ultrasonic imaging apparatus includes a probe for transmitting ultrasonic signals to a target object so as to acquire an ultrasonic image of the target object, and receiving ultrasonic echo signals reflected from the target object. The probe is connected to a piezoelectric substance, a matching layer, a backing layer (serving as a sound absorption layer), a lens, etc., and includes a case having an opened upper and a cover coupled to an upper end of the opened case and directly contacting a surface of the target object.

SUMMARY

Therefore, it is an aspect of the present invention to provide a probe for an ultrasonic imaging apparatus so as to generate images of the inside of a target object using ultrasonic waves, and a method for manufacturing the same.

Additional aspects of the invention will be set forth in part in the description which follows and, in part, will be obvious from the description, or may be learned by practice of the invention.

In accordance with one aspect of the present invention, a probe for an ultrasonic imaging apparatus includes: a piezoelectric unit including a piezoelectric substance and an electrode; a printed circuit board (PCB) unit having a printed circuit board (PCB), configured to be formed at a lateral surface of the piezoelectric unit; a matching layer formed at front surfaces of the piezoelectric unit and the PCB unit; and a backing layer formed at a back surface of the piezoelectric unit and the PCB unit.

The PCB unit may be formed at both lateral surfaces of the piezoelectric unit on the basis of the piezoelectric unit inserted into the PCB unit.

The spacing between one PCB unit formed at one side of the piezoelectric unit and another PCB unit formed at the other side thereof may correspond to an elevation-directional width of the piezoelectric unit.

The PCB unit may have the same height as an axial-directional height of the piezoelectric unit.

The PCB unit may further include a support unit that has a predetermined thickness so as to support the PCB unit.

The PCB unit may have the same height as an axial-directional height of the piezoelectric unit on the basis of a thickness of the support unit.

The PCB may include a flexible printed circuit board (FPCB).

The PCB unit may have a folded shape in a manner that one end of the FPCB encloses the support unit.

The support unit may be a rigid support unit; and the PCB unit may have a rigid-flexible printed circuit board (R-FPCB) shape formed by bonding of the rigid support unit and the FPCB.

The R-FPCB may include an internal space corresponding to a size of the piezoelectric unit.

The piezoelectric unit may be bonded to the internal space.

The PCB unit may include a line electrically connected to the electrode.

The line may include a plurality of lines, wherein the plurality of lines is arranged to be spaced apart from each other by a predetermined distance in a lateral direction.

The plurality of lines arranged at one side of the piezoelectric unit and the plurality of lines arranged at the other side thereof may be arranged to cross each other.

The piezoelectric unit and the PCB unit may channel division in a lateral direction on the basis of the arrangement of the lines.

The PCB unit may further include a conductive through hole electrical connected to lines formed on a front surface of the PCB unit.

The conductive through hole may be bonded to the support unit or is formed to pass through the support unit.

At least one of the matching layer and the backing layer may include a conductive material.

The probe may further include: at least one electrode layer configured to electrically connect the electrode to the PCB.

The backing layer may include a plurality of backing layers.

The PCB unit may be bonded to the piezoelectric unit through an adhesive, wherein the adhesive is formed of a non-conductive material.

In accordance with another aspect of the present invention, a method for manufacturing a probe of an ultrasonic imaging apparatus includes: forming a piezoelectric unit configured to include a piezoelectric substance and an electrode; forming a printed circuit board (PCB) unit configured to include a printed circuit board (PCB) and a support unit; and bonding the piezoelectric unit and the PCB unit to a backing layer.

The forming of the PCB unit may include: forming the PCB unit to have the same height as an axial-directional height of the piezoelectric unit on the basis of a thickness of the support unit.

The bonding to the backing layer may include: bonding the PCB unit to be located at a lateral surface of the piezoelectric unit.

The bonding to the backing layer may include: bonding the PCB unit so that the PCB unit is located at both sides of the piezoelectric unit on the basis of the piezoelectric unit interposed in the PCB unit.

The bonding to the backing layer may include: performing bonding in such a manner that a spacing between one PCB unit formed at one side of the piezoelectric unit and another PCB unit formed at the other side thereof corresponds to an elevation-directional width of the piezoelectric unit.

The forming of the PCB unit may include: forming the PCB including a flexible printed circuit board (FPCB).

The forming of the PCB unit may include: forming the PCB unit in such a manner that one end of the FPCB has a folded shape enclosing the support unit.

The support unit may be a rigid support unit; and the PCB unit may have a rigid-flexible printed circuit board (R-FPCB) shape formed by bonding of the rigid support unit and the FPCB.

The forming of the PCB unit may include: forming the R-FPCB in such a manner that the R-FPCB includes an internal space corresponding to a size of the piezoelectric unit.

The bonding to the backing layer may include: bonding the piezoelectric unit to the internal space.

BRIEF DESCRIPTION OF THE DRAWINGS

These and/or other aspects of the invention will become apparent and more readily appreciated from the following description of the embodiments, taken in conjunction with the accompanying drawings of which:

FIG. 2 exemplarily shows various types of probes;

FIGS. 7 to 9 illustrate a process for forming the printed circuit board (PCB) unit 210;

FIGS. 30 to 32 illustrate processes for forming the PCB unit 310;

FIG. 50 is a cross-sectional view illustrating a probe for an ultrasonic imaging apparatus according to still another embodiment.

DETAILED DESCRIPTION

Figure 1:
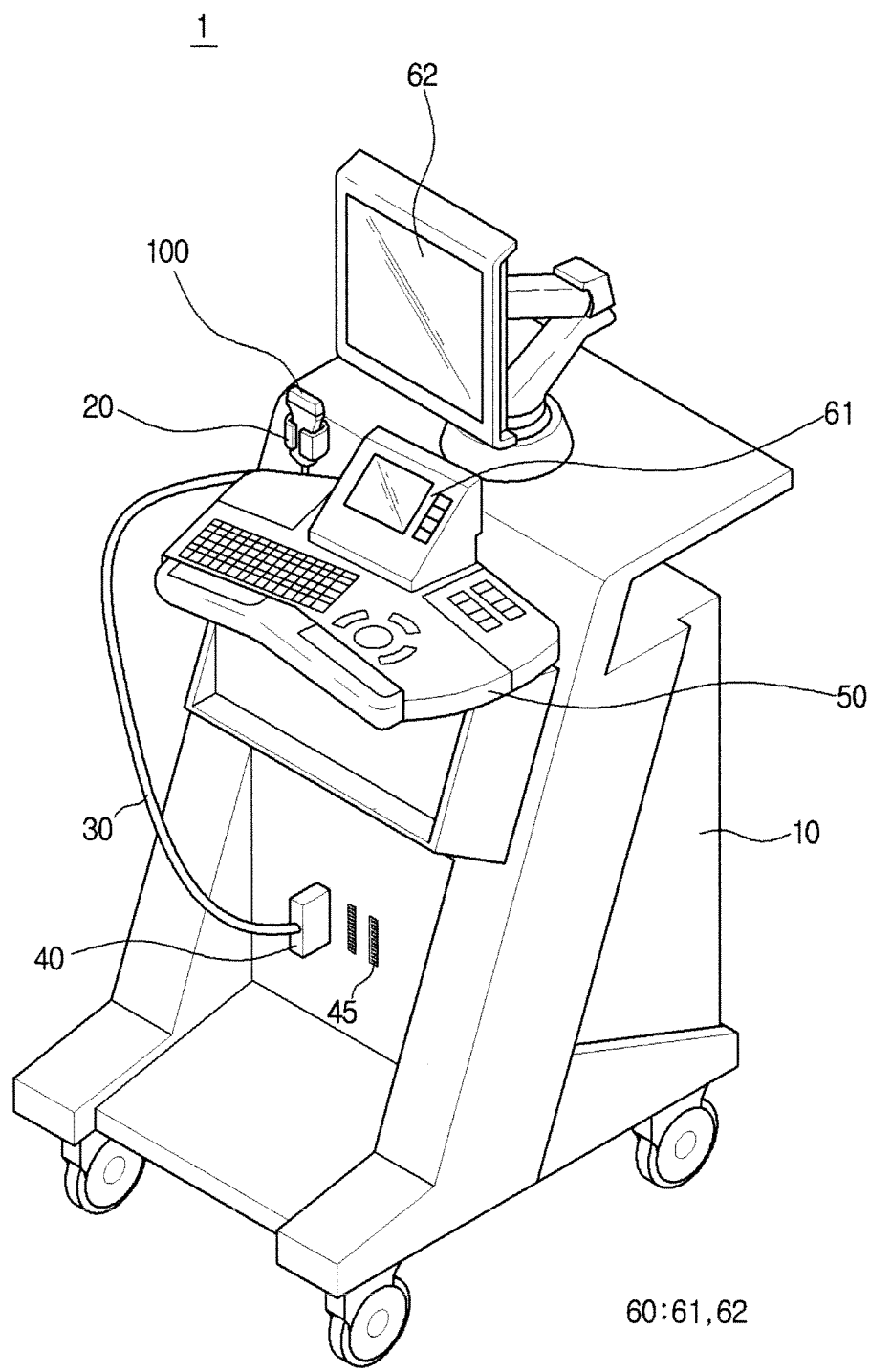
FIG. 1 is a perspective view illustrating the appearance of an ultrasonic imaging apparatus according to an exemplary embodiment of the present invention.

Reference will now be made in detail to the embodiments of the present invention, examples of which are illustrated in the accompanying drawings, wherein like reference numerals refer to like elements throughout.

A probe for an ultrasonic imaging apparatus and a method for manufacturing the same according to the embodiments will hereinafter be described with reference to the attached drawings.

FIG. 1 is a perspective view illustrating the appearance of an ultrasonic imaging apparatus according to an exemplary embodiment of the present invention. FIG. 2 exemplarily shows various types of probes.

Referring to FIG. 1, the ultrasonic imaging apparatus 1 may include a probe 100, a main body 10, and a user interface 60.

The probe 100 directly contacting a target object transmits and receives ultrasonic signals to/from the target object, and thus acquires an ultrasonic image regarding the interior of the target object. In more detail, the probe 100 includes a piezoelectric substance (also called piezoelectrics 120 of FIG. 2) by converting an electric signal into vibration energy. The probe 100 may transmit an ultrasonic signal to the target object using the piezoelectric substance 120, and receives an echo ultrasonic signal reflected from the target object. In this case, although the target object may be a living body of a human or an animal, and a target site may be tissue in the living body, such as blood vessels, bones, muscles, or the like, the scope or spirit of the present invention is not limited thereto. If necessary, all kinds of objects, internal structures of which can be imaged by the ultrasonic imaging apparatus 1, may be used as the target object without departing from the scope or spirit of the present invention.

In accordance with an arrangement format of the piezoelectric substance 120, the probe 100 may be provided as a linear probe having a linear surface as shown in FIG. 2(a), may be provided as a convex probe having a convex surface as shown in FIG. 2(b), or may be provided as a matrix probe as shown in FIG. 2(c). However, the scope or spirit of the present invention is not limited thereto, and the probe 100 may be provided not only as the shape of FIG. 2 but also as other shapes well known to those skilled in the art.

Three directions perpendicular to one another on the basis of the center point of the probe 100 may be defined as an axis direction (A), a lateral direction (L), and an elevation direction (E). In more detail, a direction of ultrasonic irradiation is defined as the axis direction (A), a direction along which the piezoelectric substance forms a column is defined as the lateral direction (L), and the remaining one direction perpendicular to the directions (A and L) may be defined as the elevation direction (E).

One end of a cable 30 may be connected to the probe 100, and a male connector 40 (not shown) may be connected to the other end of the cable 30. The male connector 40 may be physically coupled to the female connector 45 of the main body 10.

The main body 10 may include the principal constituent elements of the ultrasonic imaging apparatus 1, for example, a controller (not shown), an image processing unit (not shown), or the like. If a user or inspector inputs an ultrasonic diagnosis command, the controller (not shown) generates a control signal for irradiation of ultrasonic signals, and transmits the control signal to the probe 200. The controller receives an ultrasonic echo signal reflected from the target object, and transmits the ultrasonic echo signal to the image processing unit (not shown). The image processing unit (not shown) may perform image processing, such as noise elimination or distortion correction, on the basis of the ultrasonic echo signal, and may generate an ultrasonic image regarding the interior of the target object.

As described above, the main body 10 may transmit and receive signals to/from the probe 100. For this purpose, the main body 10 includes at least one female connector 45, and the female connector 45 may be connected to the probe 100 through the cable 30 and the male connector 40.

In addition, a plurality of casters (not shown) for mobility of the ultrasonic imaging apparatus 1 may be provided at the lower portion of the main body 10. The plural casters may fix the ultrasonic imaging apparatus 1 in a specific place or allow the ultrasonic imaging apparatus 1 to move in a specific direction.

The user interface 60 including an input unit 61 and a display unit 62 may be provided above the main body 10, so that the user interface may receive a user command as an input or may display an ultrasonic image.

The input unit 61 may receive commands regarding the operations of the ultrasonic imaging apparatus 1. For example, the input unit 61 may receive commands to select one of ultrasonic diagnosis start, diagnosis part selection, and mode selection of the output ultrasonic images, from the user. The commands inputted through the input unit 70 may be transmitted to the main body 10 through wired communication or wireless communication.

Here, the user may be, but not limited to, a person who diagnoses the target object using the ultrasonic imaging apparatus 1, for example, a doctor, radiologist, or nurse, and may include any one who uses the ultrasonic imaging apparatus 1. The ultrasonic imaging apparatus 1 may acquire an amplitude mode (A-mode) image, a brightness mode (B-mode) image, a Doppler mode (D-mode) image, a motion mode (M-mode) image, an elastography mode (E-mode) image, etc., and may also be formed as other formats well known to those skilled in the art.

The input unit 61 may include various buttons for user input or hardware (H/W) input units, for example, a switch, a pedal, a keyboard, a mouse, a trackball, a lever, a handle, and a stick, without being limited thereto. The input unit 61 is implemented as a graphical user interface (GUI) such as a touch pad for user input. That is, the input unit 61 may include a software input device. The touch pad may be implemented as a touch screen panel (TSP), so that the touch pad and the display unit 62 may constitute a mutual layer structure.

The input unit 61 may be located over the main body 10 as shown in FIG. 1. However, if the input unit 61 is implemented as a foot switch or a foot pedal, the input unit 61 may also be provided at the lower part of the main body 10. At least one probe holder 20 may be disposed around the input unit 61. Therefore, a user may hold the probe 100 on the probe holder 20 when the ultrasonic imaging apparatus 1 is not used.

The display unit 62 may display images acquired from the ultrasonic diagnosis process. The display unit 62 may display images in response to a mode selected by the user. If the user-selected mode is not present, images may be displayed as images of a fundamental mode (e.g., B mode) predetermined by the user.

The display unit 62 may be implemented as any one of a Cathode Ray Tube (CRT), a Digital Light Processing (DLP) panel, a Plasma Display Panel, a Liquid Crystal Display (LCD) panel, an Electro Luminescence (EL) panel, an Electrophoretic Display (EPD) panel, an Electrochromic Display (ECD) panel, a Light Emitting Diode (LED) panel, and an Organic Light Emitting Diode (OLED) panel, without being limited thereto.

As described above, if the display unit 62 is implemented as a touch screen that makes a mutual layer structure in cooperation with the touch pad as described above, the display unit 62 may also be used as an input unit as necessary.

Although the display unit 62 may be coupled to the main body 10 as shown in FIG. 1, it should be noted that the display unit 62 can also be detachably coupled to the main body 10 as necessary. Although not shown in FIG. 1, the ultrasonic imaging apparatus 1 may further include an additional sub-display unit for displaying applications (e.g., menu or information needed for ultrasonic diagnosis) associated with the operations of the ultrasonic imaging apparatus 1.

Figure 3:
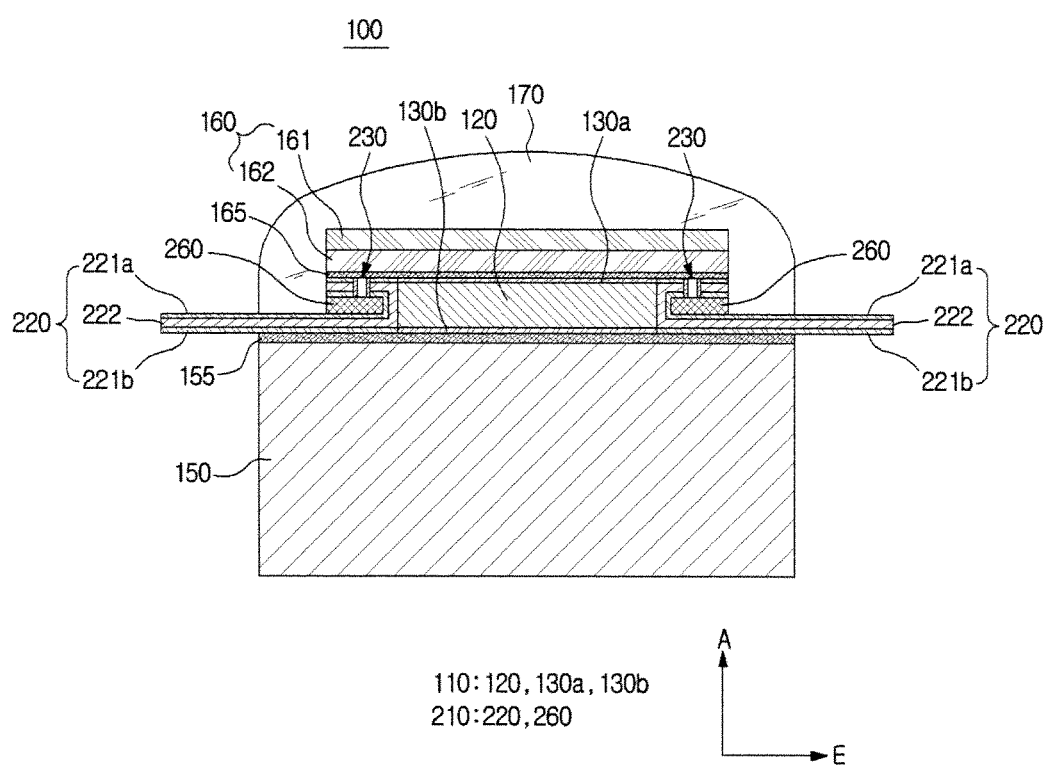
FIG. 3 is a cross-sectional view illustrating a probe for an ultrasonic imaging apparatus according to an exemplary embodiment of the present invention.
Figure 4:
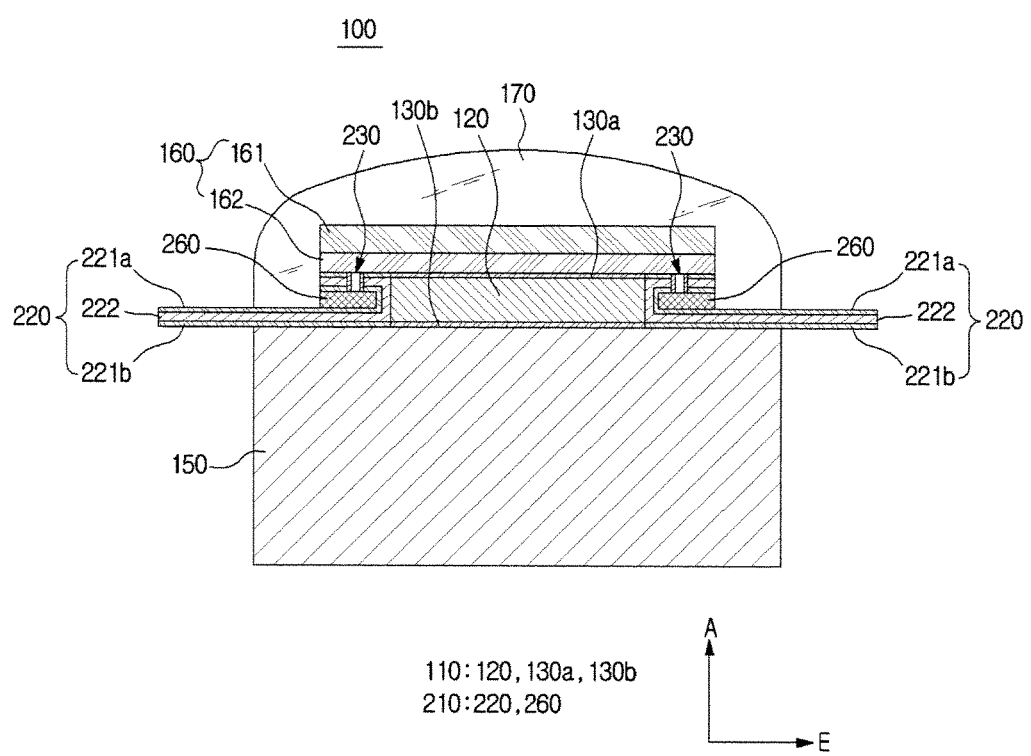
FIG. 4 is a cross-sectional view illustrating a probe for an ultrasonic imaging apparatus according to another exemplary embodiment of the present invention.

FIG. 3 is a cross-sectional view illustrating a probe for an ultrasonic imaging apparatus according to an exemplary embodiment of the present invention. FIG. 4 is a cross-sectional view illustrating a probe for an ultrasonic imaging apparatus according to another exemplary embodiment of the present invention. In FIGS. 3 and 4, a cross-sectional view of the probe 100 is a cross-section parallel to a plane of the axis direction (A) and the elevation direction (E).

Referring to FIGS. 3 and 4, the probe 100 may include a piezoelectric substance 120, electrodes (130a, 130b) formed in the piezoelectric substance, a printed circuit board 220 provided at a lateral surface of the piezoelectric substance 120, a backing layer 150 provided at a back surface of the piezoelectric substance 120, a backing layer provided in a forward direction of the piezoelectric substance 120, and a lens 170. Hereinafter, one progressing direction of ultrasonic waves is referred to as a forward direction, the other progressing direction opposite to the above progressing direction is referred to a backward direction, a surface located forward is referred to as a front surface, and a surface located backward is referred to as a back surface.

Electrodes (130a, 130b) may include a first electrode 130a and a second electrode 130b. The first electrode 130a and the second electrode 130b may be separated from each other on the basis of the piezoelectric substance 120 interposed therebetween. For example, the first electrode 130a may be arranged at the front surface of the piezoelectric substance 120, and the second electrode 130b may be arranged at the back surface of the piezoelectric substance 120.

The first electrode 130a and the second electrode 130b may be formed of high-conductivity metal such as gold, silver, or copper, so that the first and second electrodes 130a and 130b may provide an electric signal to the piezoelectric substance 120. Any one of the first electrode 130a and the second electrode 130b may be used as a signal electrode (or an anode) of the piezoelectric substance 120, and the other one of the first and second electrodes 130a and 130b may be used as a ground electrode (or a cathode) of the piezoelectric substance 120. For convenience of description, the first electrode 130a may be used as a ground electrode and the second electrode 130b may be used as a signal electrode.

The piezoelectric substance 120 may generate ultrasonic waves using the resonance phenomenon. The piezoelectric substance 120 converts electric signals received from the electrodes (130a, 130b) into dynamic vibration energy to generate ultrasonic waves, and may re-convert vibration energy received from a target object into electric signals. In more detail, if the probe 100 receives a current from an external power-supply device or an internal power source such as a battery, the current may be applied to the piezoelectric substance 120 through the electrodes (130a, 130b).

The piezoelectric substance 120 generates ultrasonic waves simultaneously while being vibrated along the received current, and transmits the ultrasonic waves to a target object located outside. The piezoelectric substance 120 receives again ultrasonic echo signals reflected from the target object, vibrates along the ultrasonic echo signals, generates a current having a frequency corresponding to a vibration frequency, and transmits the generated current to the neighbor electrodes (130a, 130b).

The piezoelectric substance 120 may include a PZT (lead zirconate titanate) ceramic, a PZNT single crystal formed of a solid solution of lead zinc niobate and lead titanate, a PZMT single crystal formed of a solid solution of lead magnesium niobate and lead titanate, or the like, but is not limited thereto. If the piezoelectric substance 120 is formed of a single crystal (monocrystal), the probe having a large bandwidth may be formed, and low-frequency ultrasonic signals and high-frequency ultrasonic signals can be transmitted and received through the piezoelectric substance 120.

The piezoelectric substance 120 may be divided into a plurality of sub-piezoelectric substances by dicing so as to form an array. The electrodes (130a, 130b) arranged at the front and back surfaces of the piezoelectric substance 120 are divided into a plurality of sub-electrodes so as to form an array. That is, the array formed by the piezoelectric substance 120 is opposite to the array formed by the electrodes (130a, 130b), such that a plurality of channels may be constructed. A method for constructing the plurality of channels of the piezoelectric substance 120 and the electrodes (130a, 130b) will hereinafter be described in detail. In addition, the piezoelectric substance 120 and the electrodes (130a, 130b) are included in a piezoelectric unit 110.

The PCB 220 may be provided at a lateral surface of the piezoelectric unit 110. Since the PCB 220 is provided at a lateral surface but not the front or back surface of the piezoelectric unit 110 (i.e., since the PCB 220 is not provided at the progressing direction of ultrasonic waves), ultrasonic waves generated from the piezoelectric substance 120 can be transmitted to the target object. While the ultrasonic echo signals from the target object are received by the piezoelectric substance 120, ultrasonic acoustic characteristics changed by the PCB 220 can be prevented from changing.

The PCB 220 is coupled to a support unit 260 supporting the PCB 220. The PCB 220 and the support unit 260 are contained in a PCB unit 210. The PCB unit 210 may have the same height as the piezoelectric unit 110 in response to a thickness variation of the support unit 260. Each PCB 210 may be arranged at each of both lateral surfaces of the piezoelectric unit 110, so that the PCBs 210 may be arranged at both lateral surfaces of the piezoelectric unit 110 one by one.

A circuit board (CB) 220 may be implemented as a Flexible Printed Circuit Board (FPCB). Since the PCB 220 is implemented as the Flexible Printed Circuit Board (FPCB), the PCB unit 210 may form a folded structure as shown in FIG. 3. A method for forming the folded-type PCB unit 210 will hereinafter be described in detail.

The PCB unit 220 may be a double-sided PCB, and may include a first line unit 221a, a second line unit 220b, and an insulation unit 222.

The insulation unit 222 may be disposed between the first line unit 221a and the second line unit 221b, or may be provided at a connection part of the first line unit 221a. The insulation unit 222 may be formed of a soft insulation material. For example, the insulation unit 222 may be formed of a polyester (PET) film, a polyimide (PI) film, or the like, but not limited thereto. The insulation unit 222 may be formed of other soft insulation materials well known to those skilled in the art.

The first line unit 221a and the second line unit 221b may be spaced apart from each other by the insulation unit 222 interposed therebetween. As described above, since the insulation unit 222 is formed of an insulation material, electric connection between the first line unit 221a and the second line unit 221b is severed through the insulation unit 222.

Figure 10:
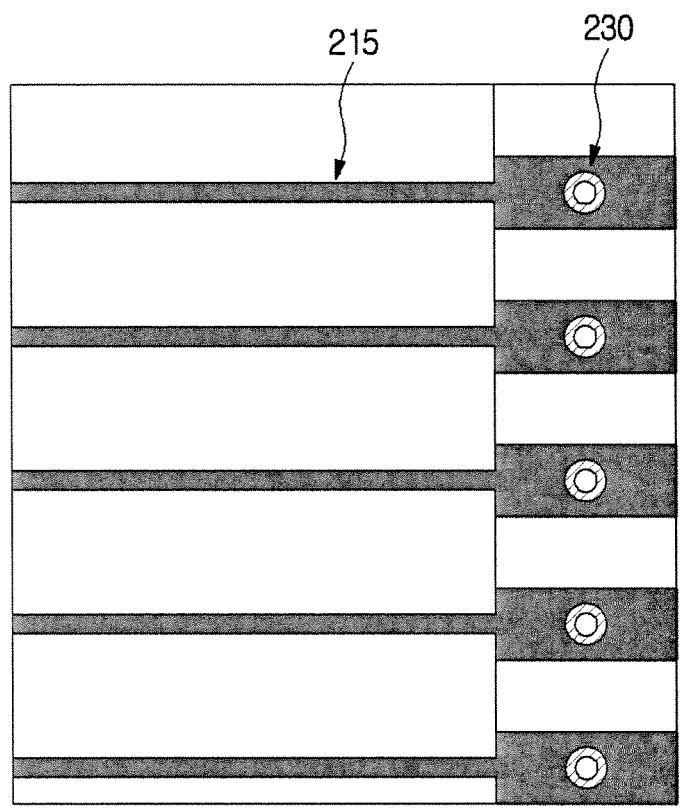
FIG. 10 is a plan view illustrating the PCB unit including a conductive through hole according to an exemplary embodiment.

Each of the first line unit 221a and the second line unit 221b may include a plurality of conductive lines (See 215 of FIG. 10). The plural conductive lines 215 may be spaced apart from each other at intervals of a predetermined distance in the lateral direction (L), and the position of the conductive line 215 of the first line unit 221a is opposite to the position of the conductive line 215 of the second line unit 221b. The conductive line 215 of the PCB unit 210 located at one lateral surface of the piezoelectric unit 110 and the conductive line 215 of the PCB unit 210 located at the other lateral surface are arranged to cross each other, and a detailed description thereof will hereinafter be described.

Since the PCB unit 210 is arranged at a lateral surface of the piezoelectric unit 110, any one of the first line unit 221a and the second line unit 221b is coupled to the first electrode 130a, and the other one is coupled to the second electrode 130b. For convenience of description and better understanding of the present invention, the first line unit 221a is coupled to the first electrode 130a, and the second line unit 221b is coupled to the second electrode 130b. The conductive line 215 of the first line unit 221a may be electrically coupled to the first electrode 130a acting as a ground electrode, so that the first line unit 221a may be used as a ground line. In addition, the conductive line 215 of the second line unit 221b may be electrically coupled to the second electrode 130b acting as a signal electrode, so that the second line unit 221b may be used as a line unit for signaling.

The support unit 260 may be disposed between the PCBs 220 so as to support the PCB 220. The support unit 260 may be formed of an insulation material or a conductive material. The support unit 260 may be formed of a soft material or a rigid material. In addition, the support unit 260 may be provided as a block form. For example, the support unit 260 may be formed of a ceramic or epoxy material, or may be formed of an epoxy block. Assuming that the support unit 260 can support the PCB unit 220, constituent elements or shapes of the support unit 260 are not limited.

The support unit 260 may be formed to have a predetermined thickness. As described above, the PCB unit 210 may have the same height as the piezoelectric unit 110 through thickness control of the support unit 260.

The backing layer 150 may be arranged at the rear of the piezoelectric unit 110. The backing layer 150 reduces a pulse width of ultrasonic waves by suppressing vibration of the piezoelectric substance 120, and prevents the ultrasonic waves from being propagated to the rear of the piezoelectric substance 120, so that it can prevent image distortion. For this purpose, the backing layer 150 may be formed of a material for vibration suppression or may also be formed of a material for ultrasonic absorption. For example, the backing layer 150 may be formed of rubber including epoxy resin or tungsten powder, etc.

An electrode layer 155 may be arranged at the front surface of the backing layer 150 as shown in FIG. 3. The electrode layer 155 may be disposed among the piezoelectric unit 110, the PCB unit 210, and the backing layer 150. The electrode layer 155 may be formed of a conductive material such as gold, silver, or copper, or may be formed by deposition, sputtering, plating, spraying or the like. Therefore, the electrode layer 155 may electrically connect the second electrode 130b of the piezoelectric unit 110 to the second line unit 221b of the PCB unit 210.

The backing layer 150 may be formed of a conductive material. The electrode layer 155 may be omitted as shown in FIG. 4. The backing layer 150 may be formed of a conductive material, or some parts thereof may also be formed of a conductive material. If some parts of the backing layer 150 are formed of a conductive material, the front surface of the backing layer 150 contiguous to the second electrode 130b of the piezoelectric unit 110 may be formed of a conductive material.

The matching layer 160 may be arranged in a forward direction of the piezoelectric unit 110 and the PCB unit 210. The matching layer 160 matches acoustic impedance of the piezoelectric substance 120 to another acoustic impedance of the target object, so that ultrasonic signals generated from the piezoelectric substance 120 can be efficiently transferred to the target object, or ultrasonic echo signals reflected from the target object can be efficiently transferred to the piezoelectric substance 120. Therefore, the matching layer 160 may have an intermediate value between the acoustic impedance of the piezoelectric substance 120 and the acoustic impedance of the target object.

In addition, the matching layer 160 may include a plurality of layers. If the matching layer 160 includes a plurality of layers, the plural layers may be provided in a manner that the acoustic impedance is gradually changed from the piezoelectric substance 120 to the target object, such that a difference in acoustic impedance between the piezoelectric substance 120 and the target object can be gradually reduced. For example, the matching layer 160 may include a first matching layer 161 and a second matching layer 162 as shown in FIG. 3. Each of the first matching layer 161 and the second matching layer 162 may have an intermediate value between the acoustic impedances of the piezoelectric substance 120 and the target object, and may be provided in a manner that the acoustic impedance of the first matching layer 161 and the acoustic impedance of the second matching layer 162 can be gradually changed.

For example, the first matching layer 161 and the second matching layer 162 may be formed of glass or resin. The first matching layer 161 and the second matching layer 162 may be formed of different materials in a manner that the acoustic impedance can be gradually changed. Alternatively, there may be a difference in material between the first matching layer 161 and the second matching layer 162, or there may also be a difference in thickness between the first matching layer 161 and the second matching layer 162.

An electrode layer 165 may be arranged at the back surface of the matching layer 160 as shown in FIG. 3. The electrode layer 165 may be disposed among the piezoelectric unit 110, the PCB unit 210, and the matching layer 160. The electrode layer 165 may be formed of a conductive material such as gold, silver or copper, or may also be formed by deposition, sputtering, plating or spraying. Therefore, the electrode layer 165 may electrically connect the first electrode 130a of the piezoelectric unit 110 to the first line unit 2218 of the PCB unit 210.

The matching layer 160 may be formed of a conductive material, for example, graphite, gold, silver or copper. The electrode layer 165 may be omitted as shown in FIG. 4. The matching layer 160 may be formed of a conductive material, or some parts thereof may be formed of a conductive material. If some parts of the matching layer 160 are formed of a conductive material, a back surface of the matching layer 160 contiguous to the first electrode 130a of the piezoelectric unit 110 may be formed of a conductive material.

The lens 170 may be provided at the front surface of the matching layer 160, and may focus ultrasonic waves progressing forward at a specific position. As shown in FIG. 3, the lens 170 may have a convex shape in a forward direction, may have a concave shape in a backward direction, or may also have other formats other than curved shapes. The focusing point of ultrasonic waves may be changed according to a curvature or shape of the lens 170.

Figure 5:
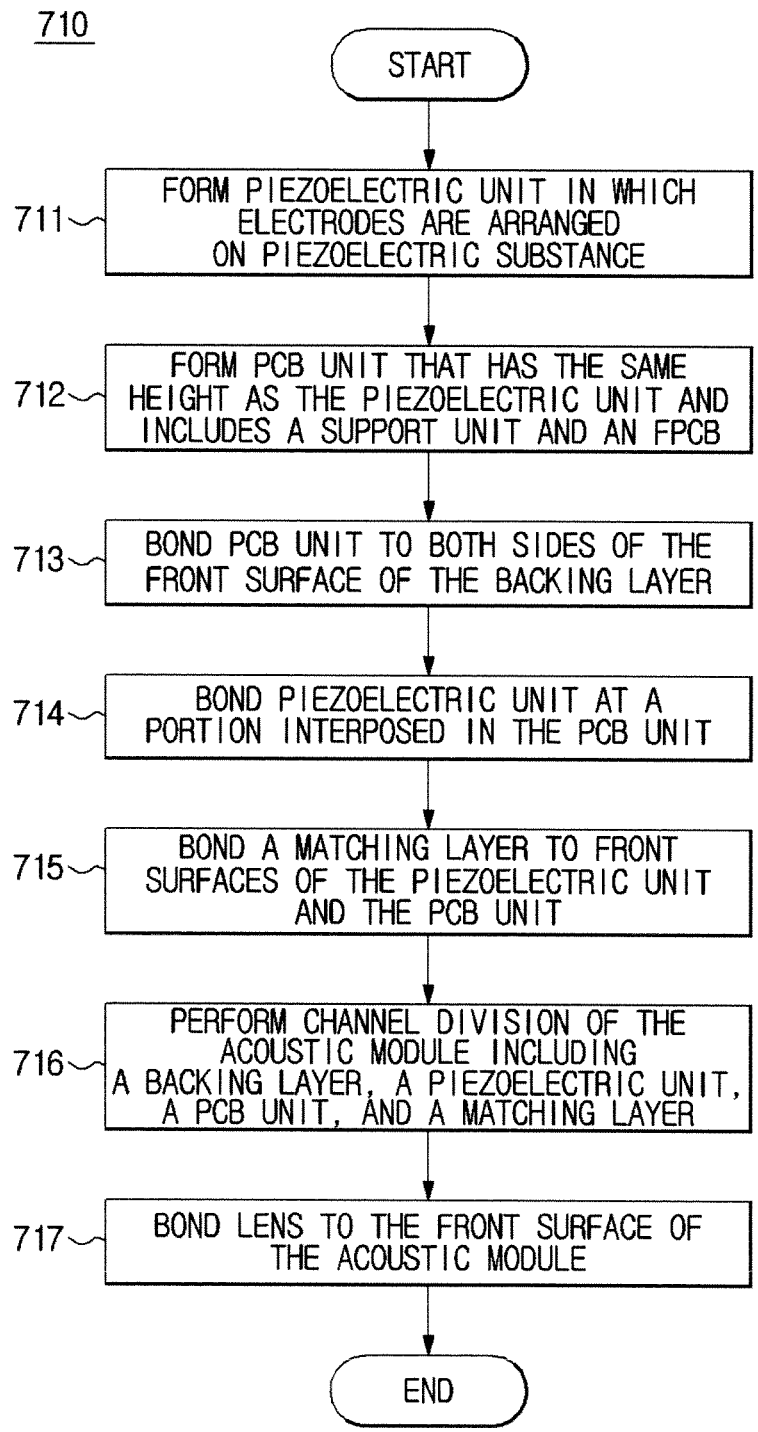
FIG. 5 is a flowchart illustrating a method for manufacturing the probe of the ultrasonic imaging apparatus shown in FIG. 3.

FIG. 5 is a flowchart illustrating a method for manufacturing the probe of the ultrasonic imaging apparatus shown in FIG. 3. FIGS. 6 to 14 illustrate processes for forming the piezoelectric substance.

Referring to FIG. 5, the piezoelectric unit 110 in which electrodes are arranged over the piezoelectric unit 120 is formed in operation 711.

Figure 6:
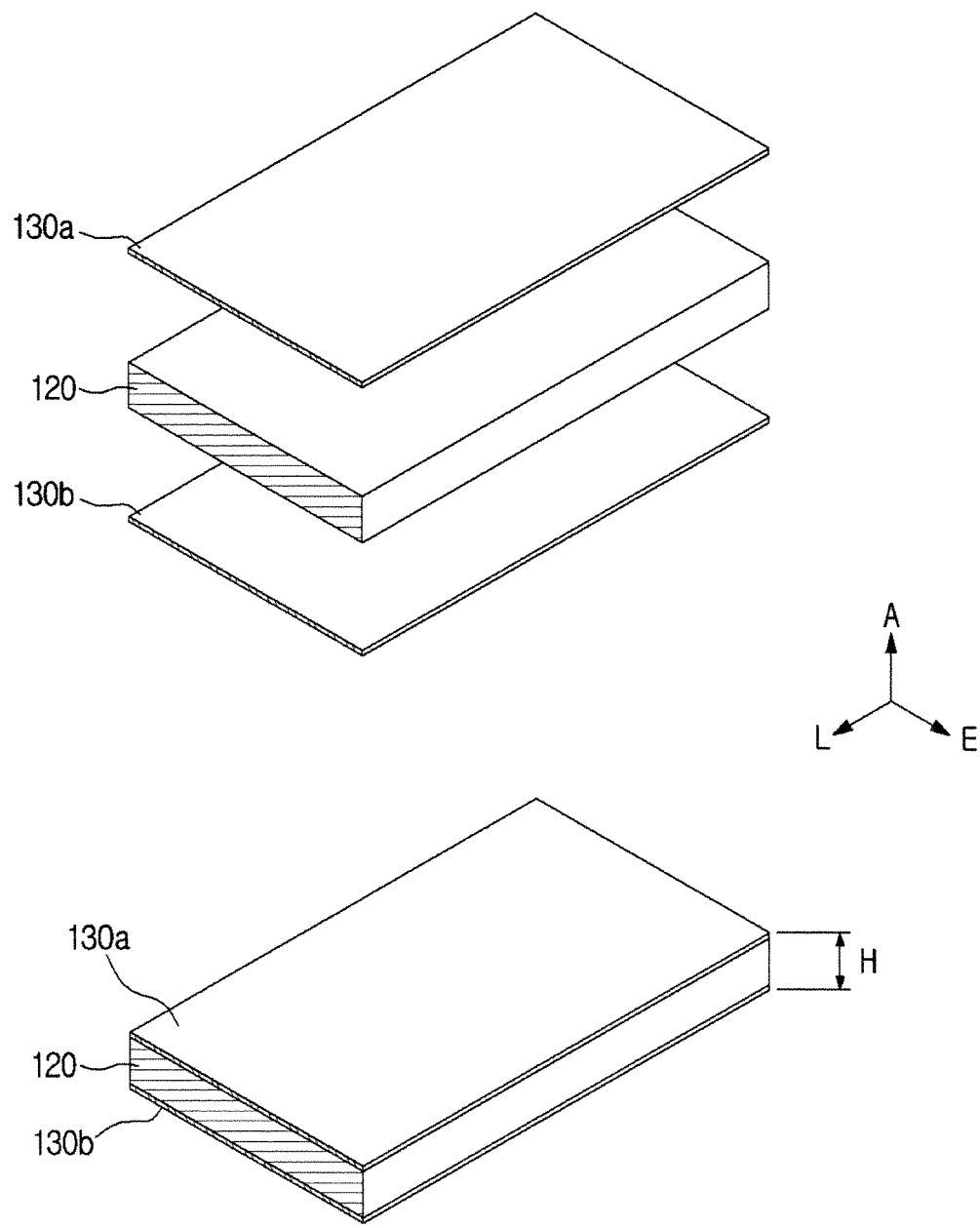
FIG. 6 illustrates a process for forming the piezoelectric substance.

FIG. 6 is a conceptual diagram illustrating a method for forming the piezoelectric unit 110.

As shown in the upper part of FIG. 6, electrodes formed of high-conductivity metal, such as gold, silver or copper, may be formed at the front and back surfaces of the piezoelectric unit 120. The first electrode 130a is arranged at the front surface of the piezoelectric unit 120, and the second electrode 130b is arranged at the back surface of the second electrode 130b. When the width is defined in the elevation direction (E) and the length is defined in the lateral direction (L), the width and length of the first electrode 130a may be respectively matched to the width and length of the piezoelectric substance 120. Likewise, the width and length of the second electrode 130b may be respectively matched to the width and length of the piezoelectric substance 120.

The first electrode 130a and the second electrode 130b respectively arranged at the front surface and the back surface of the piezoelectric substance 120 may be bonded to the piezoelectric substance 120 as shown in a lower part of FIG. 6, so that formation of the piezoelectric unit 110 is completed. The thickness or height in an axis direction of the piezoelectric unit 110 will hereinafter be referred to as H.

Figure 8:
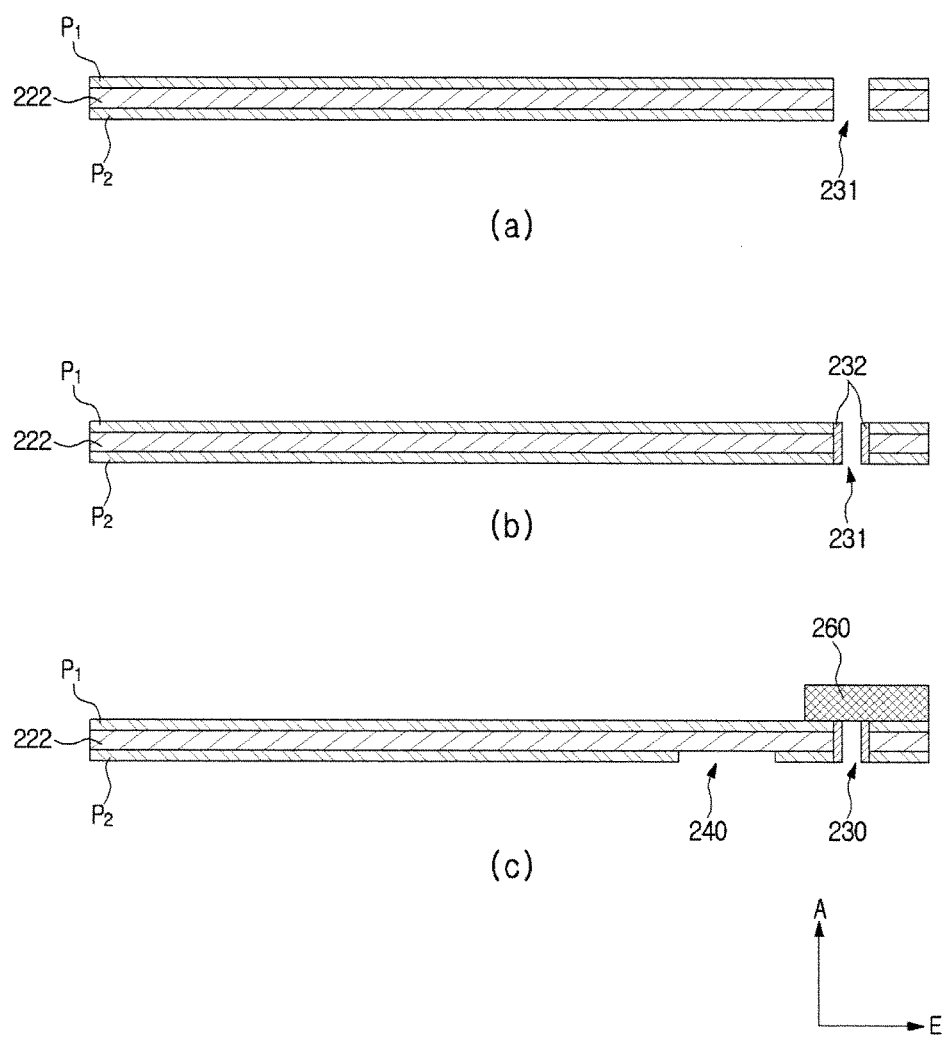
Figure 9:
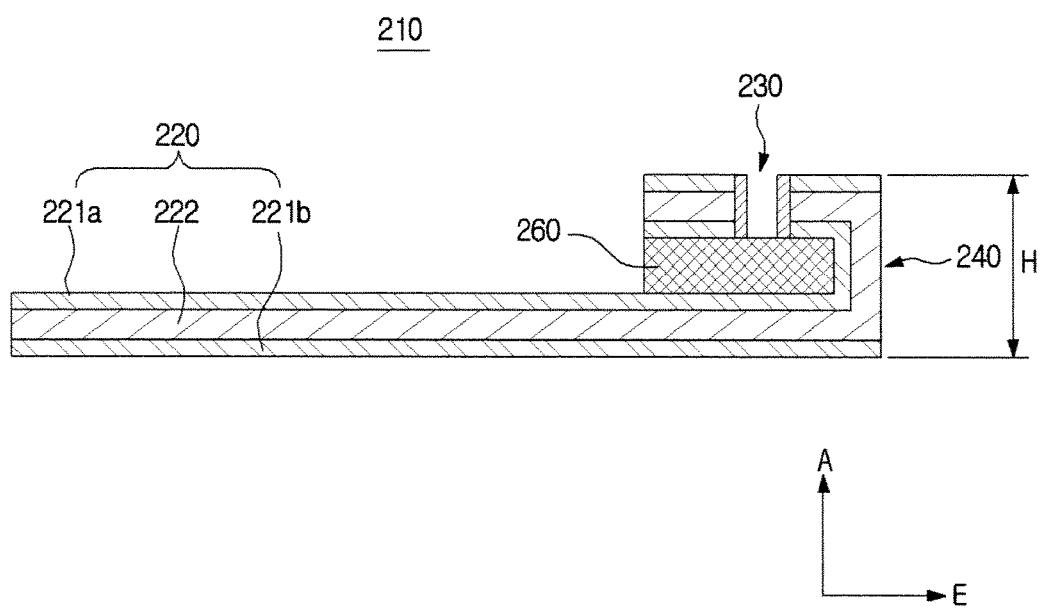

Thereafter, the piezoelectric unit 110 includes a support unit 260 and an FPCB 220, and the PCB unit 210 having the same height as the piezoelectric unit 110 is formed in operation 712. FIGS. 7 to 9 illustrate a method for forming the PCB unit 210.

As shown in FIG. 7, the FPCB 220 is a double-sided FPCB, so that plural conductive lines may be respectively printed at the front surface and the back surface of the insulation unit 222. In this case, a front line unit P1 including a plurality of conductive lines printed on the front surface of the insulation unit 222 is defined, and a back line unit P2 including a plurality of conductive lines printed on the back surface of the insulation unit 222 is defined.

The conductive lines of the front line unit P1 are printed on the front surface of the insulation unit 222 while being spaced apart from each other by a predetermined distance, and the conductive lines of the back line unit P2 are printed on the back surface of the insulation unit 222 while being spaced apart from each other by a predetermined distance. In this case, the position of the conductive line of the front line unit P1 is opposite to the position of the conductive line of the back line unit P2. As can be seen from FIG. 7(a), if the conductive lines (T11, T12, T13, T14, T15) of the front line unit P1 are printed while being spaced apart from each other by a predetermined distance (S) in the lateral direction (L), the conductive lines (T21, T22, T23, T24, T25) of the back line unit P2 are also printed while being spaced apart from each other by a predetermined distance (S) in the lateral direction (L). T1$i$ and T2$i$ may be constructed to have opposite positions in the order of i (where i=1, 2, 3, 4, 5).

Although the conductive lines may be printed at intervals of a predetermined distance as shown in FIG. 7(b), it should be noted that the spacing between both ends of the conductive lines may have different values. The spacing between the conductive lines may be gradually reduced or increased in the range from one end to the other end of the conductive lines.

The conductive lines may be printed to have a constant thickness, or may also be printed to have different thickness at both ends thereof. The thickness of the conductive lines may be gradually reduced or increased in the range from one end to the other end of the conductive lines. Specifically, both ends of the conductive lines contained in the back line unit P2 may be formed to have different widths as shown in FIG. 7(b).

A through hole 231 is formed at one end of the FPCB 220 having the thick conductive lines as shown in FIG. 8(a). The through hole 231 is formed over a conductive line. Electric connection of the front line unit P1 is severed by the through hole 231, and electric connection in the back line unit P2 is severed through the through hole 231. After generation of the through hole 231, the through hole 231 may be plated or fabricated with a conductive material such as gold, silver or copper. Because the through hole 231 is fabricated with the conductive material 232, the front line unit P1 and the back line unit P2 may be electrically interconnected as shown in FIG. 8(b). Therefore, the through hole 231 fabricated with the conductive material 232, or a material including the through hole 231 or the conductive material 232 will hereinafter be referred to as a conductive through hole 230.

After generation of the conductive through hole 230, a block-shaped second support unit 260 is bonded to one surface of the conductive through hole 230 as shown in FIG. 8(c), and a groove 240 is formed at the other surface of the conductive through hole 230 at intervals of a predetermined distance. Electric connection of the back line unit P2 is severed again in a section in which a groove 240 is formed.

As shown in FIG. 9, if the groove 240 is formed in the FPCB 220, one end of the FPCB 220 is folded using flexibility, and formation of the PCB unit 210 is completed. The above-mentioned structure in which one end of the FPCB 220 is folded and the support unit 260 is enclosed by the FPCB 220 is a folded structure of the PCB unit 210. A conductive line part remaining on a back surface of the support unit 260 from among the legacy back line unit P2 is referred to as a second line unit 221b, and a specific part excluded from the second line unit 221b from among the front line unit P1, the conductive through hole 230, and the back line unit P2 may be defined as a first line unit 221a. Alternatively, a conductive line part of the back line unit P2 connected to the front line unit P1 through the conductive through hole 230 may also be defined as the first line unit 221a.

The height of the PCB unit 210 may be adjusted through a thickness of the support unit 260 and the width of the groove 240, such that the PCB unit 210 may be formed to have the same height H as the piezoelectric unit 110.

Figure 11:
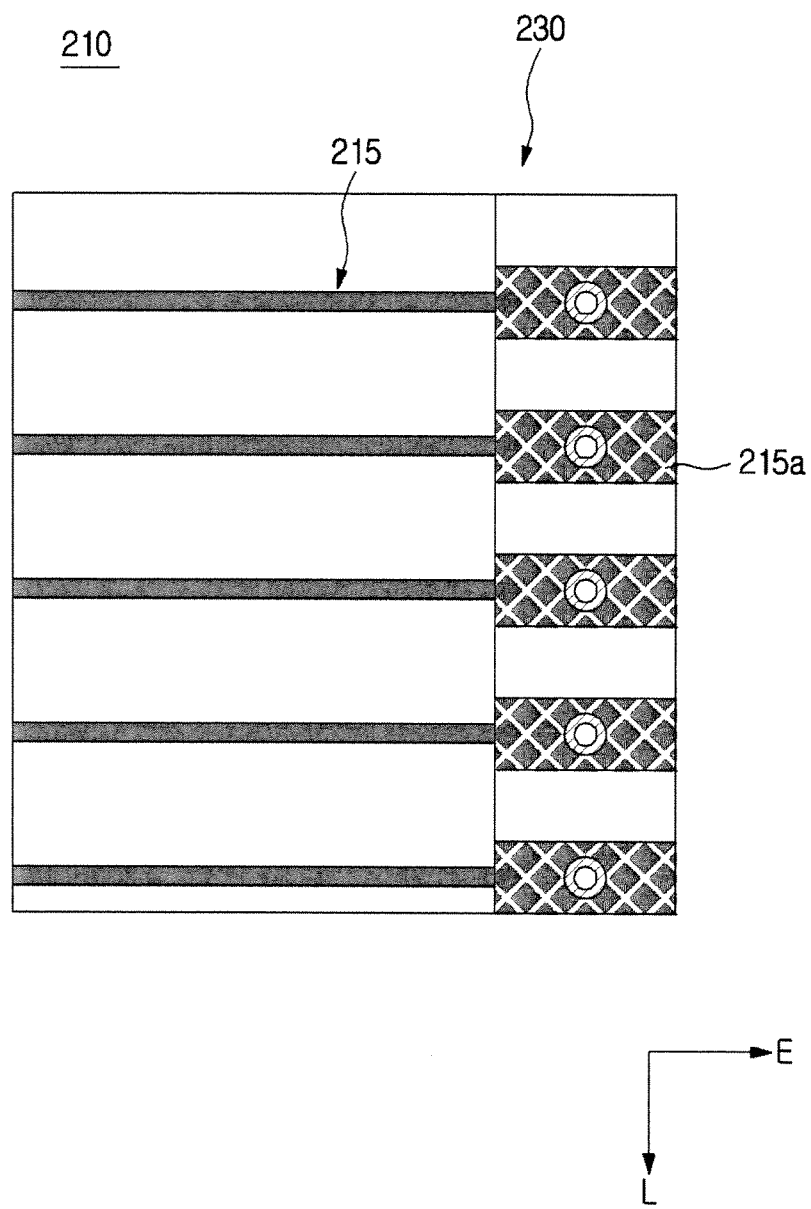
FIG. 11 is a plan view illustrating the PCB unit having a conductive through hole according to another embodiment.

FIG. 10 is a plan view illustrating the PCB unit including a conductive through hole according to an exemplary embodiment. FIG. 11 is a plan view illustrating the PCB unit having a conductive through hole according to another embodiment.

Referring to FIGS. 10 and 11, a plurality of conductive lines 215 may be spaced apart from each other by a predetermined distance on the PCB unit 210. In this case, the spacing between the conductive lines 215 may be gradually reduced in the range from one end having a folded structure to the other hand having no folded structure. By the folded structure of the PCB unit, a conductive line part located at the front of the PCB unit 210 may be formed to have a larger thickness than the remaining parts. The conductive through hole 230 may be arranged at the front of the PCB unit 210. In addition, the conductive through hole 230 may electrically connect the front line unit P1 to the back line unit P2, and may be formed over the conductive line 215.

Referring to FIG. 11, a groove 215a may be formed at a conductive line part arranged at the front of the PCB unit 210. The groove 215a may be formed by etching of the conductive lines. For etching, the dry etch method or the wet etch (◎) 불명확한 내용 확인요망 method can be applied. Although the groove 215a may form lattice structures having a regular spacing, it should be noted that a net structure having irregular spacing may be formed as necessary. Because of formation of the groove 215a, the conductive line 215 may be divided into a plurality of regions, and the plural regions may be formed in various shapes, for example, a diamond shape, a rectangular shape, a triangular shape, etc.

If the PCB unit 210 is formed in operation 712, the PCB unit 210 is bonded to both sides of the front surface of the backing layer 150 in operation 713. The piezoelectric unit 110 is bonded between the PCB units 210 in operation 714.

Figure 12:
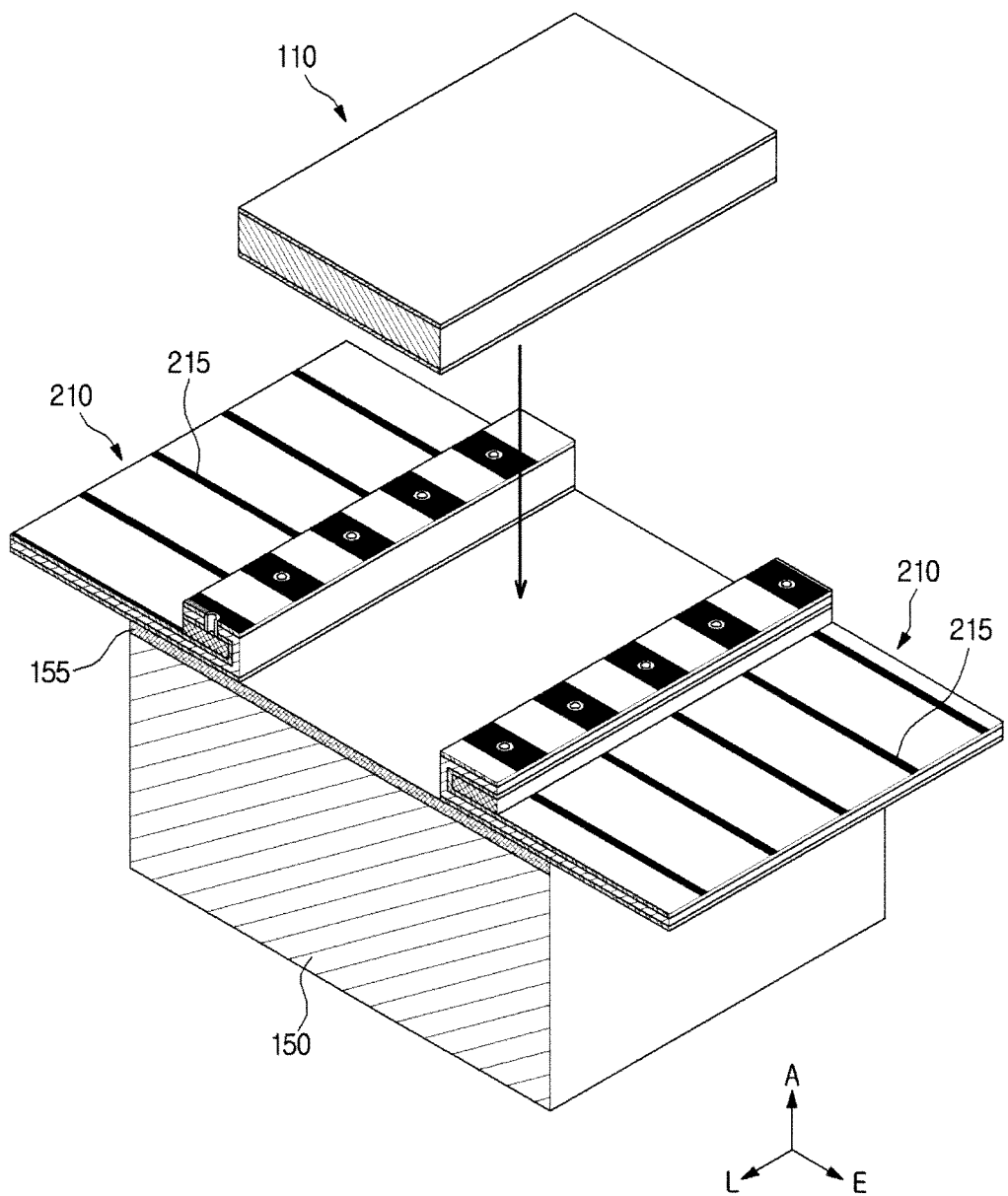
FIG. 12 illustrates an exemplary method for bonding the PCB unit 210 and a piezoelectric unit to a backing layer.

FIG. 12 illustrates an exemplary method for bonding the PCB unit 210 and a piezoelectric unit to a backing layer.

Referring to FIG. 12, by depositing a conductive material, such as gold, silver, or copper on the front surface of the backing layer 150, or by sputtering, plating, or spraying, the electrode layer 155 is formed. The PCB unit 210 is bonded to both sides of the front surface of the backing layer 150 including the electrode layer 155. If the backing layer 150 is formed of a conductive material, the electrode layer 155 may be omitted. Here, the PCB unit 210 may be directly bonded to the backing layer 150.

The backing layer 150 may have a larger width than the piezoelectric unit 110, and one PCB unit 210 may be bonded to each of one side and the other side of the front surface of the backing layer 150 on the basis of a predetermined interval corresponding to the width of the piezoelectric unit 110. In this case, the conductive line 215 of the PCB unit 210 bonded to the one side and the conductive line 215 of the PCB unit 210 bonded to the other side are arranged to cross each other. The piezoelectric unit 110 is bonded to be meshed with the spacing formed by the PCB unit 210.

The bonding (or attachment) of the PCB unit 210 or the bonding (or attachment) of the piezoelectric unit 110 may be achieved through an adhesive. The piezoelectric unit 110 may be bonded to the backing layer 150 and the PCB unit 210 through an adhesive. Here, the adhesive may be formed of a non-conductive material.

In accordance with the bonding between the PCB unit 210 and the piezoelectric unit 110, a first electrode 130a serving as a ground electrode of the piezoelectric unit 110 is connected to the first line unit 221a so as to form a line unit for grounding, and a second electrode 130b serving as a signal electrode is connected to the second line unit 221b so as to form a line unit for signaling.

If the piezoelectric unit 110 is bonded, the matching layer 160 is bonded to the front surfaces of the piezoelectric unit 110 and the PCB unit 210 in operation 715.

Figure 13:
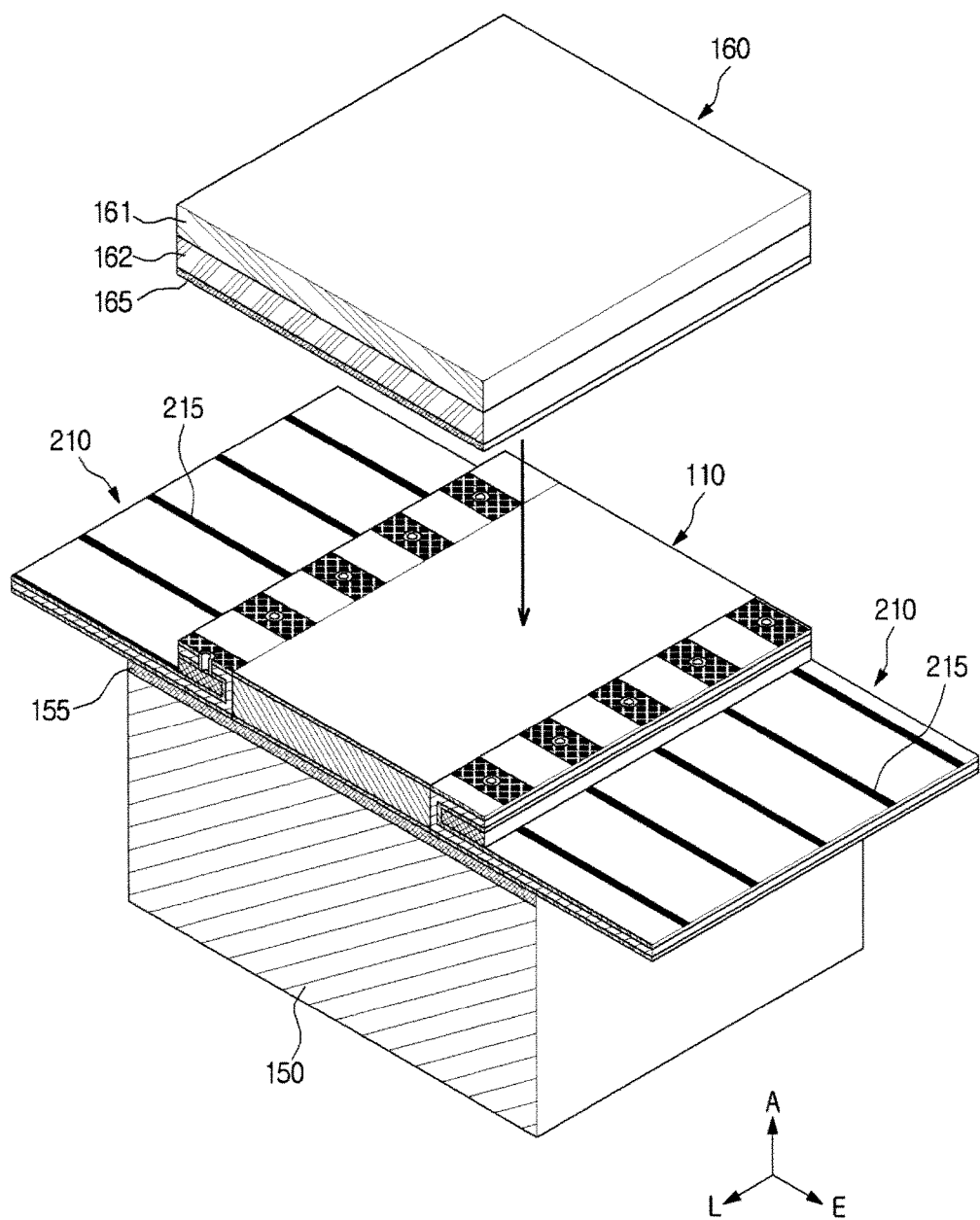
FIG. 13 illustrates an attachment example of a matching layer.

FIG. 13 illustrates an attachment example of a backing layer.

Referring to FIG. 13, by depositing a conductive material, such as gold, silver, or copper on the back surface of the matching layer 160, or by sputtering, plating, or spraying, the electrode layer 165 is formed. The matching layer 160 including the electrode layer 165 is bonded to the piezoelectric unit 110 and the PCB unit 210. If the matching layer 160 is formed of a conductive material, the electrode layer 165 may be omitted. Here, the matching layer 160 may be directly bonded to the piezoelectric unit 110 and the PCB unit 210.

The matching layer 160 may be deposited through an adhesive, or may be bonded through bonding. If a conductive line 215 of the PCB forms the groove 215a as shown in FIG. 13, a contact area between the adhesive of the PCB unit 210 and the electrode layer 165 is increased as large as the groove 215a. That is, according to formation of the groove 25a, electric resistance of the electrode layer 165 can be reduced. Coupling force between the PCB unit 210 and the matching layer 160 may be increased. Meanwhile, a module formed by bonding of the matching layer 160 (i.e., the module formed by bonding of the PCB unit 210 and the matching layer 160) will hereinafter be defined as an acoustic module.

The acoustic module including the backing layer 150, the piezoelectric unit 110, the PCB unit 210, and the matching layer 160 is channel-divided through dicing in operation 716.

Figure 14:
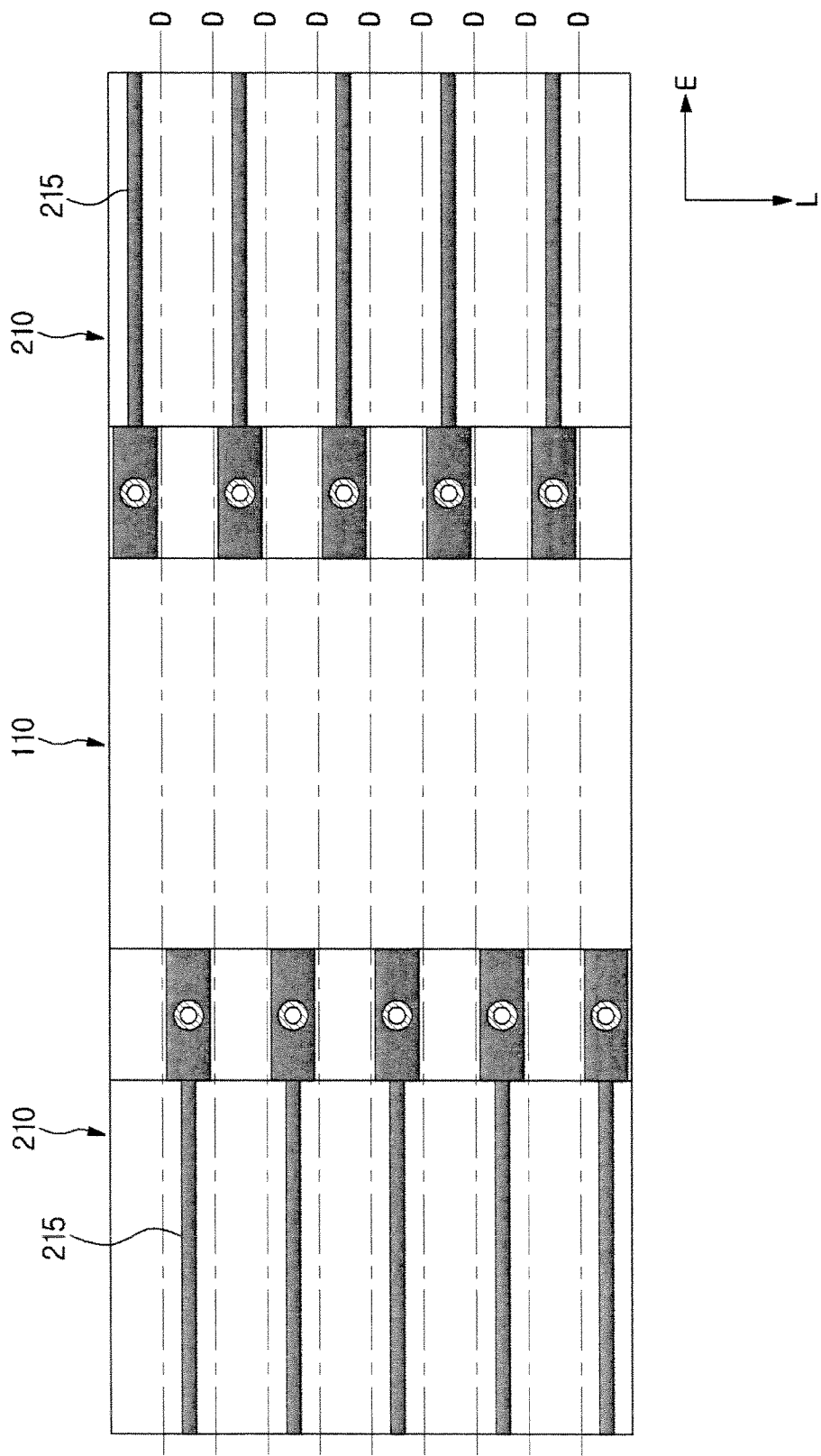
FIG. 14 illustrates a channel division process of an acoustic module.

FIG. 14 illustrates a channel division process of the acoustic module, and is a plan view of the acoustic module. As described above, although the acoustic module is formed by bonding of the piezoelectric unit 110, the PCB unit 210, and the matching layer 160, it should be noted that the matching layer 160 may be omitted from the following description for convenience of description.

Referring to FIG. 14, each of both PCB units 210 (i.e., one PCB unit 210 bonded to one side of the front surface of the backing layer 150 and the other PCB unit 210 bonded to the other side of the front surface of the backing layer 150) may include a plurality of conductive lines 215 spaced apart from each other by a predetermined distance. Here, the conductive line 215 of the PCB unit 210 bonded to one side and the other conductive line 215 of the PCB unit 210 bonded to the other side may be arranged to cross each other.

Dicing may be achieved considering that both conductive lines 215 are arranged to cross each other. In more detail, such dicing may be achieved along a specific line D disposed between one conductive line 215 provided at one side and the other conductive line 215 arranged at the other side. The conductive line 215 provided at one side and the other conductive line 215 provided at the other side may be electrically isolated from each other through dicing.

Dicing may be performed at a predetermined depth. In order to reliably isolate among the matching layer 160, the piezoelectric unit 110, and the PCB unit 210, the matching layer 160, the piezoelectric unit 110, the PCB unit 210, and the backing layer 150 may be diced to a predetermined depth. That is, the acoustic module including the backing layer 150, the piezoelectric unit 110, the PCB unit 210, and the matching layer 160 may be diced to a predetermined depth. Through dicing, the piezoelectric unit 110 and the PCB unit 210 are isolated from each other so as to form a plurality of arrays. This operation for forming the plural arrays may be referred to as an operation for constructing the plural channels or a channel division operation.

Although the above-mentioned description has exemplarily disclosed that channel division is performed through dicing of the acoustic module, the scope or spirit of the present invention is not limited thereto, and channel division may also be achieved using an arbitrary method (e.g., etching, photolithographic pattering, etc.) known to those skilled in the art. Meanwhile, since the piezoelectric unit 110 is disposed between the PCB units 210, the piezoelectric unit 110 or the piezoelectric substance 120 can be prevented from being damaged during the channel division caused by dicing, resulting in increased strength against impact.

Upon completion of channel division, the lens 170 is bonded to the front surface of the acoustic module, and the probe 100 shown in FIG. 3 is formed in operation 717. Prior to bonding of the lens 170, a process for forming at least one of a chemical shield (CS) and a radio frequency (RF) on the front surface of the acoustic module may be further used.

Figure 15:
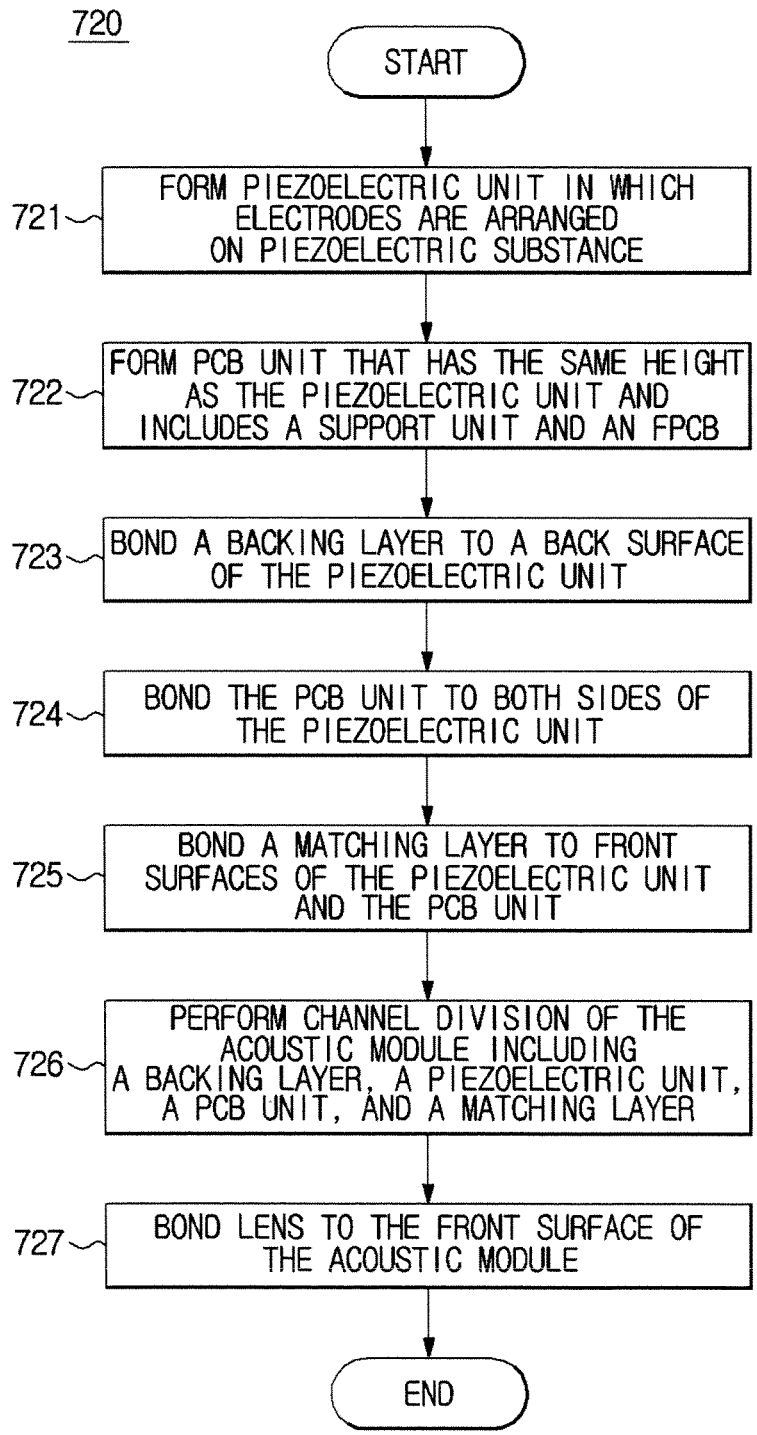
FIG. 15 is a flowchart illustrating a method for manufacturing the probe of the ultrasonic imaging apparatus shown in FIG. 3 according to another embodiment.
Figure 16:
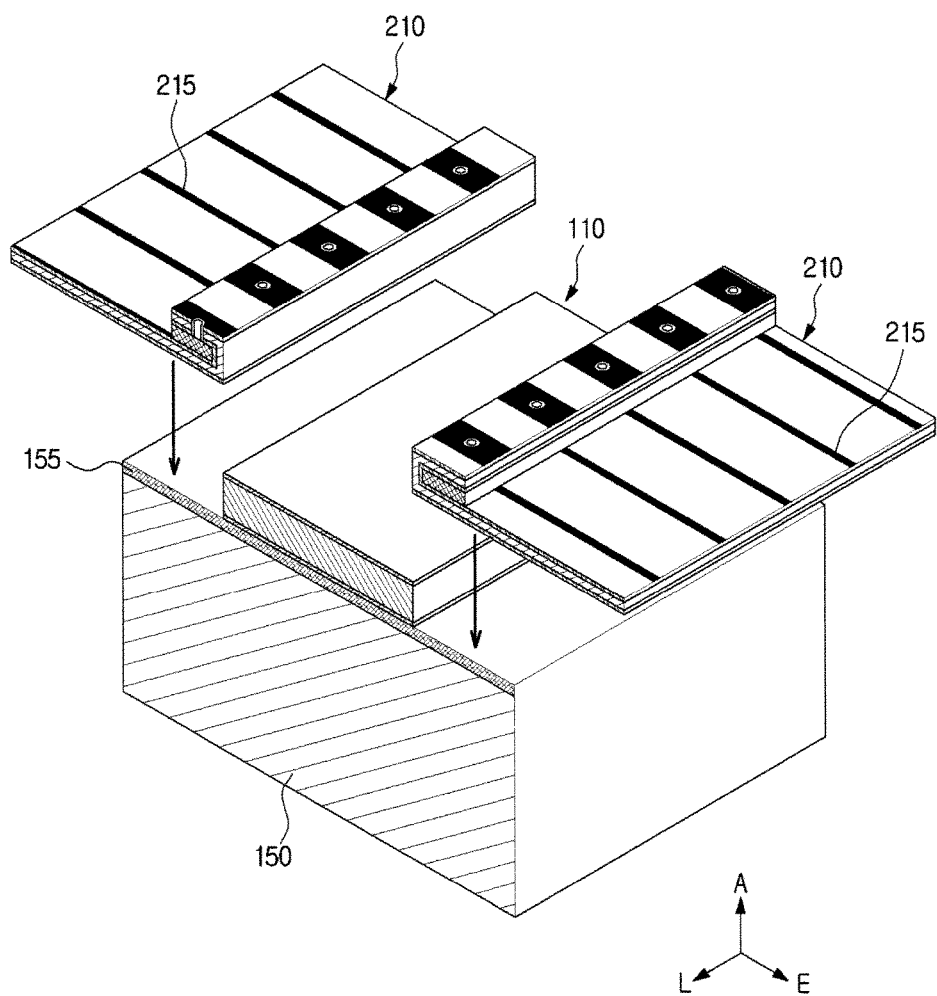
FIG. 16 illustrates a method for manufacturing the probe of the ultrasonic imaging apparatus according to another embodiment.

FIG. 15 is a flowchart illustrating a method for manufacturing the probe of the ultrasonic imaging apparatus shown in FIG. 3 according to another embodiment. FIG. 16 illustrates a method for manufacturing the probe of the ultrasonic imaging apparatus according to another embodiment. In a method for forming the probe of the ultrasonic imaging apparatus according to another embodiment, a detailed description of the same or similar process as in FIG. 5 will herein be omitted for convenience of description.

Referring to FIG. 15, the piezoelectric unit 110 in which electrodes are arranged in the piezoelectric substance 120 is formed in operation 721. Thereafter, the PCB unit 210 including the support unit 260 and the FPCB 220 is formed to have the same height as the piezoelectric unit 110 in operation 722. The operation 721 may correspond to the operation 711, and the operation 722 may correspond to the operation 712, and as such a detailed description thereof will herein be omitted for convenience of description.

If the PCB unit 210 is formed, the backing layer 150 may be bonded to the back surface of the piezoelectric substance 110, or the piezoelectric unit 110 may be bonded to the front surface of the backing layer 150 in operation 723. The PCB unit 210 may be bonded to both sides of the piezoelectric unit 110 in operation 724. FIG. 16 shows another example in which the PCB unit 210 and the piezoelectric unit are bonded to the backing layer.

Referring to FIG. 16, by depositing a conductive material, such as gold, silver, or copper on the front surface of the backing layer 150, or by sputtering, plating, or spraying, the electrode layer 155 is formed. The piezoelectric unit 110 may be bonded to the front surface of the backing layer 150 including the electrode layer 155. If the backing layer 150 is formed of a conductive material, the electrode layer 155 may be omitted. Here, the piezoelectric unit 110 may be directly bonded to the backing layer 150.

The backing layer 150 may have a larger width than the piezoelectric unit 110, and the piezoelectric unit 110 may be bonded to be located at the center of the front surface of the backing layer 150. One PCB unit 210 may be bonded to one side of the piezoelectric unit 110, and the other one PCB unit 210 may be bonded to the other side thereof. In this case, the conductive line 215 of the PCB unit 210 bonded to one side and the conductive line 215 of the PCB unit 210 bonded to the other side may be arranged to cross each other.

In addition, the bonding of the piezoelectric unit 110 or the bonding of the PCB unit 210 may be achieved by an adhesive. The piezoelectric unit 110 may be bonded to the backing layer 150 through adhesive, and the PCB unit 210 may be bonded to the backing layer 150 and the piezoelectric unit 110 through the adhesive. In this case, the adhesive may be formed of a non-conductive material.

In accordance with the bonding of the PCB unit 210 and the piezoelectric unit 110, a first electrode 130*a* acting as a ground electrode of the piezoelectric unit 110 is connected to the first line unit 221*a* so that a line unit for a grounding part is formed. A second electrode 130*b* acting as a signal electrode is connected to the second line unit 221*b* so that a line unit for a signaling part is formed.

If the PCB unit 210 is bonded, the matching layer 160 is bonded to the front surface of the PCB unit 210 in operation 725. The acoustic module including the backing layer 150, the piezoelectric unit 110, the PCB unit 210, and the matching layer 160 is channel-divided through dicing in operation 726. The lens 170 is bonded to the front surface of the channel-divided acoustic module, such that the probe 100 shown in FIG. 2 is formed in operation 727. Prior to bonding of the lens 170, a process for forming at least one of a chemical shield (CS) and a radio frequency (RF) on the front surface of the acoustic module may be further used. Operations 725 to 727 may respectively correspond to the operations 715 to 717, and as such a detailed description thereof will herein be omitted for convenience of description.

Although the above-mentioned description has exemplarily disclosed that a process (i.e., operation 722) for forming the PCB unit 210 is performed prior to the process (i.e., operation 723) for bonding the piezoelectric unit 110 to the backing layer 150, it should be noted that the process (i.e., operation 722) for forming the PCB unit 210 can also be achieved after the process (i.e., operation 723) for bonding the piezoelectric unit 110 to the backing layer 150.

Figure 17:
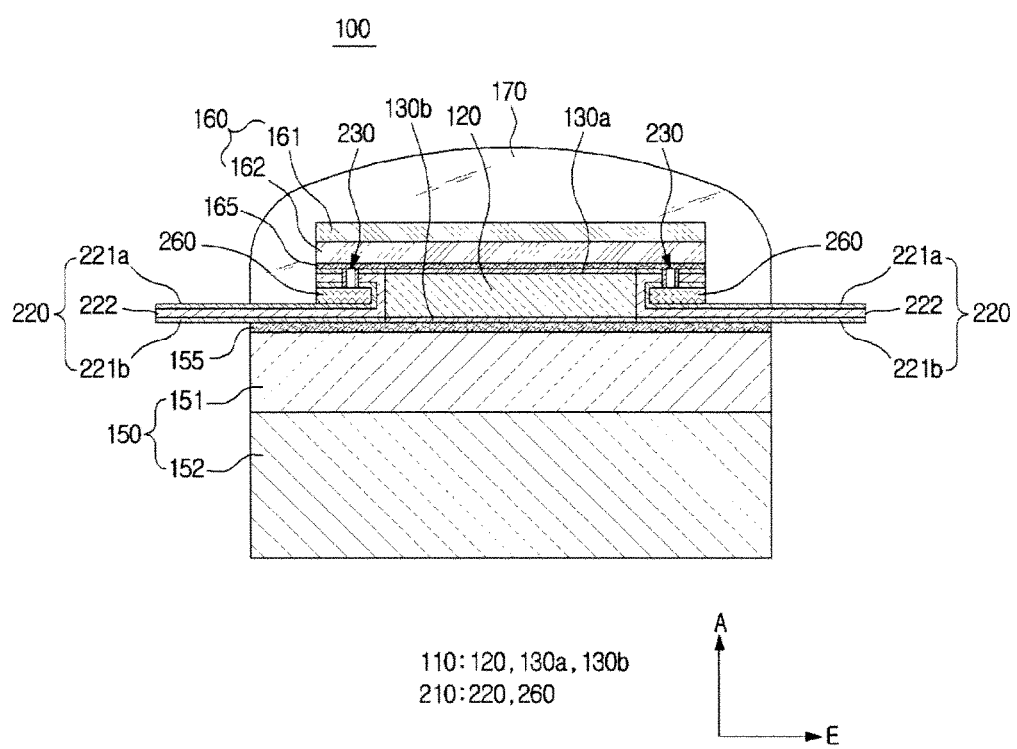
FIG. 17 is a cross-sectional view illustrating a probe for an ultrasonic imaging apparatus according to still another embodiment.

FIG. 17 is a cross-sectional view illustrating a probe for an ultrasonic imaging apparatus according to still another embodiment. For convenience of description, the same or similar structures in conduction and function as those described in the above-mentioned embodiment are denoted by the same reference numerals, and the explanation thereof will be omitted herein.

Referring to FIG. 17, the probe 100 may include a piezoelectric unit 110, a PCB unit 210 provided at a lateral surface of the piezoelectric unit 110, a backing layer 150 provided at a back surface of the piezoelectric unit 110, a matching layer 160 provided at a front surface of the piezoelectric unit 110, and a lens 170. In this case, the piezoelectric unit 110 may include the piezoelectric substance 120 and electrodes (130*a*, 130*b*) formed at front and back surfaces of the piezoelectric substance 120. The PCB unit 210 may include an FPCB 220 and a support unit 260 to support the FPCB 220, and form a folded structure. In addition, the PCB unit 210 may have the same height as that of the piezoelectric unit 110 through the support unit 260.

The backing layer 150 includes a plurality of layers, and is arranged at the back surface of the piezoelectric unit 110. As can be seen from FIG. 17, the backing layer 150 may include a first backing layer 151 and a second backing layer 152. The first backing layer 151 and the second backing layer 152 may be formed of a material of vibration suppression or a material of ultrasonic absorption, for example, rubber including epoxy resin or tungsten powder. The first backing layer 151 and the second backing layer 152 may be formed of the same material, or may also be formed of different materials. Alternatively, there is a difference in constituent ratio of material between the first backing layer 151 and the second backing layer 152.

The first backing layer 151 and the second backing layer 152 have different thicknesses. For example, the first backing layer 151 may be thinner than the second backing layer 152. The first backing layer 151 and the second backing layer 152 may have the same or different shapes. The arrangement shape of the piezoelectric substance 120 and the shape of the probe 100 may be determined according to the shapes of the first backing layer 151 and the second backing layer 152. For example, the first backing layer 151 and the second backing layer 152 are formed to have a block shape, and may form a linear probe. In addition, the first backing layer 151 is formed in a block shape, and the second backing layer 152 may have a convex shape in a forward direction so as to form a convex probe.

Figure 18:
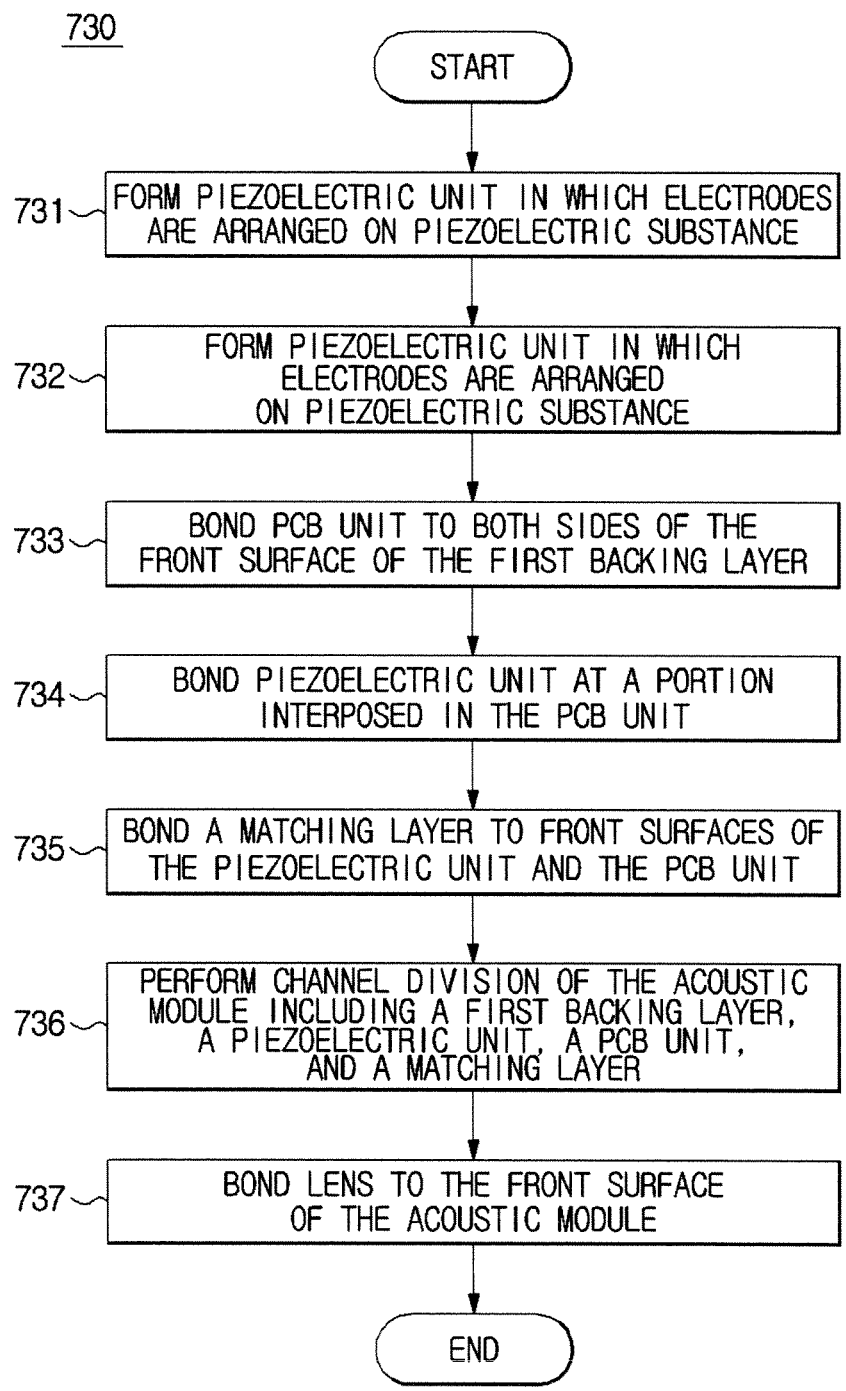
FIG. 18 is a flowchart illustrating a method for manufacturing the probe of the ultrasonic imaging apparatus shown in FIG. 17.
Figure 19:
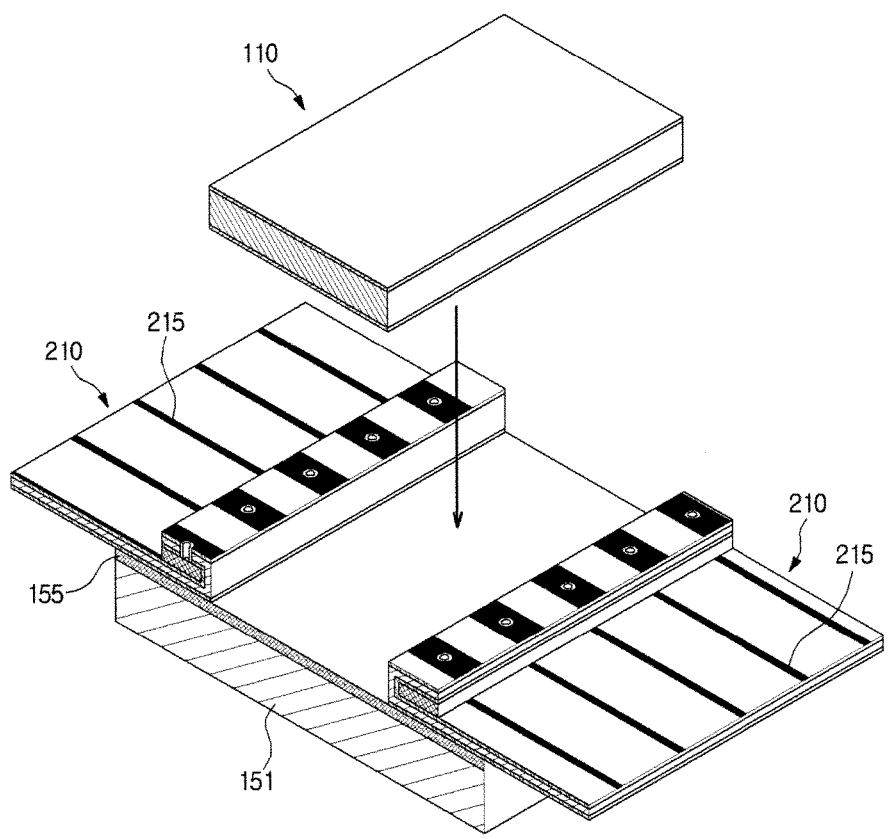
FIG. 19 illustrates an exemplary method for bonding a PCB unit 210 and a piezoelectric unit to a first backing layer.
Figure 20:
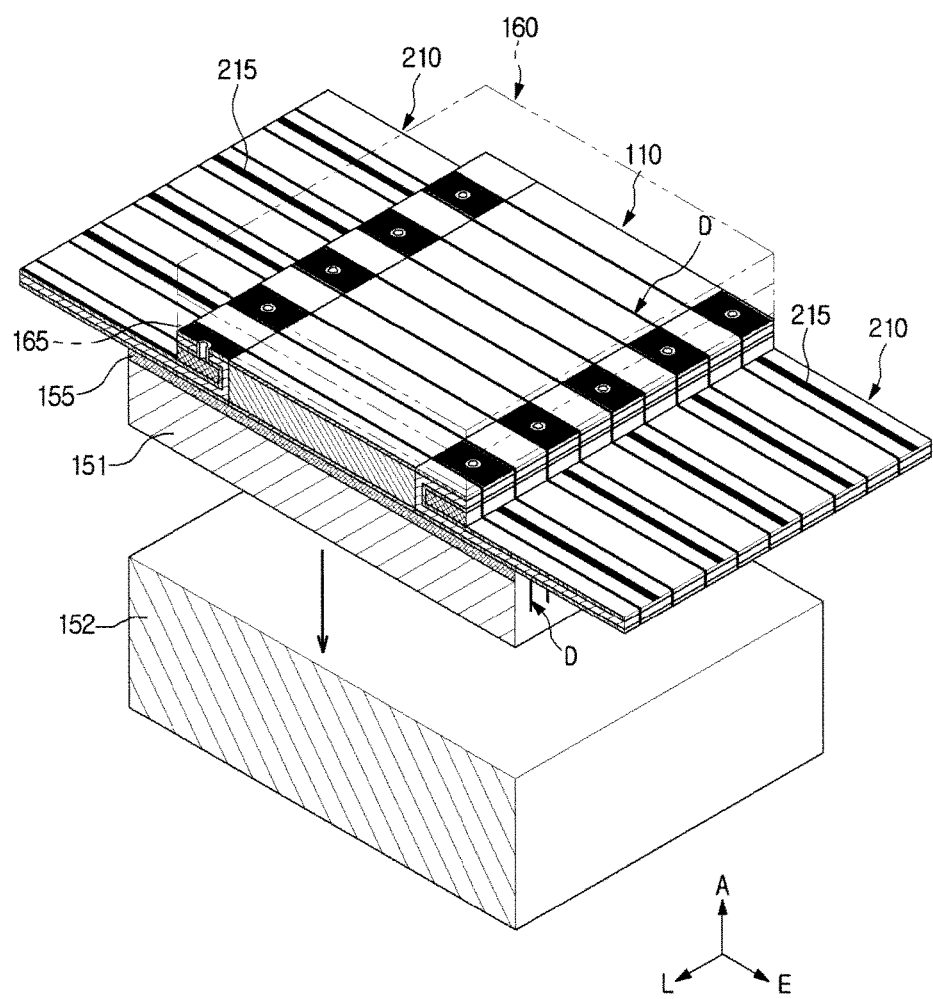
FIG. 20 illustrates an exemplary method for bonding a channel division and acoustic module of the acoustic module to a second backing layer.

FIG. 18 is a flowchart illustrating a method for manufacturing the probe of the ultrasonic imaging apparatus shown in FIG. 17. FIGS. 19 and 20 are flowcharts illustrating a method for manufacturing the probe of the ultrasonic imaging apparatus. For convenience of description, the same or similar structures in construction and function as those described in the above-mentioned embodiment are denoted by the same reference numerals, and the explanation thereof will be omitted herein.

Referring to FIG. 18, the piezoelectric unit 110 in which electrodes are arranged on the piezoelectric substance 120 is formed in operation 731. Thereafter, the PCB unit 210 including the support unit 260 and the FPCB 220 may have the same height as the piezoelectric unit 110 in operation 732. Operations 731 and 732 may respectively correspond to operations 711 and 712.

If the PCB unit 210 is formed, the PCB unit 210 is bonded to both sides of the front surface of the first backing layer 151 in operation 733, and the piezoelectric unit 110 is bonded between the PCB units 210 in operation 734.

FIG. 19 illustrates one example for bonding the PCB unit 210 and the piezoelectric unit to the first backing layer.

Referring to FIG. 19, by depositing a conductive material, such as gold, silver, or copper on the front surface of the first backing layer 151, or by sputtering, plating, or spraying, the electrode layer 155 is formed. The PCB unit 210 is bonded to both sides of the front surface of the first backing layer 151 including the electrode layer 155. If the backing layer 150 is formed of a conductive material, the electrode layer 155 may be omitted. Here, the PCB unit 210 may be directly bonded to the first backing layer 151.

The first backing layer 151 may have a larger width than the piezoelectric unit 110, and one PCB unit 210 may be bonded to each of one side and the other side of the front surface of the first backing layer 151 on the basis of a predetermined interval corresponding to the width of the piezoelectric unit 110. In this case, the conductive line 215 of the PCB unit 210 bonded to the one side and the conductive line 215 of the PCB unit 210 bonded to the other side are arranged to cross each other. The piezoelectric unit 110 is bonded to be meshed with the spacing formed by the PCB unit 210.

The bonding (or attachment) of the PCB unit 210 or the bonding (or attachment) of the piezoelectric unit 110 may be achieved through an adhesive. The PCB unit 210 may be bonded to the first backing layer 151 through an adhesive. Here, the adhesive may be formed of a non-conductive material.

In accordance with the bonding between the PCB unit 210 and the piezoelectric unit 110, a first electrode 130a serving as a ground electrode of the piezoelectric unit 110 is connected to the first line unit 221a so as to form a line unit for a grounding part, and a second electrode 130b serving as a signal electrode is connected to the second line unit 221b so as to form a line unit for a signaling part.

If the piezoelectric unit 110 is bonded, the matching layer 160 is bonded to the front surfaces of the piezoelectric unit 110 and the PCB unit 210, the acoustic module is formed in operation 735. In this case, the acoustic module may be defined as a module formed by bonding of the matching layer 160. The acoustic module may be defined as a module that is formed by bonding of the first backing layer 151, the piezoelectric unit 110, the PCB unit 210, and the matching layer 160.

The acoustic module including the first backing layer 151, the piezoelectric unit 110, the PCB unit 210, and the matching layer 160 may be channel-divided through dicing in operation 736. The acoustic module is bonded to the front surface of the second backing layer 152, and the lens may be bonded to the front surface of the acoustic module in operation 737.

FIG. 20 illustrates an exemplary method for bonding a channel division and acoustic module of the acoustic module to a second backing layer.

Referring to FIG. 20, each of both PCB units 210 (i.e., one PCB unit 210 bonded to one side of the front surface of the first backing layer 151 and the other PCB unit 210 bonded to the other side of the front surface of the first backing layer 151) may include a plurality of conductive lines 215 spaced apart from each other by a predetermined distance. Here, the conductive line 215 of the PCB unit 210 bonded to one side and the other conductive line 215 of the PCB unit 210 bonded to the other side may be arranged to cross each other.

Channel division may be achieved considering that both conductive lines 215 are arranged to cross each other. In more detail, such dicing may be achieved along a specific line D disposed between one conductive line 215 provided at one side and the other conductive line 215 arranged at the other side. Therefore, one conductive line 215 and the other conductive line 215 may form a plurality of arrays, and may be electrically isolated from each other. In order to reliably isolate among the matching layer 160, the piezoelectric unit 110, and the PCB unit 210, the matching layer 160, the piezoelectric unit 110, and the PCB unit 210 may be diced to a predetermined depth. That is, as shown in FIG. 20, the acoustic module including the first backing layer 151, the piezoelectric unit 110, the PCB unit 210, and the matching layer 160 may be diced to a predetermined depth.

Although the acoustic module can be channel-divided through dicing as described above, the scope or spirit of the present invention is not limited thereto, and channel division may also be achieved using an arbitrary method (e.g., etching, photolithographic pattering, etc.) known to those skilled in the art.

If channel division is achieved, the channel-divided acoustic module may be bonded to the front surface of the second backing layer 152. Although FIG. 20 exemplarily shows that the first backing layer 151 and the second backing layer 152 are formed as a block shape, the second backing layer 152 may also have a curved shape having a curvature. If the second backing layer 152 has a curved shape, the back surface of the acoustic module may be bended in response to the curvature of the second backing layer 152. The banded acoustic module may be bonded to the front surface of the second backing layer 152. That is, the acoustic module is modified in shape in response to the shape of the second backing layer 152, and is then bonded to the second backing layer 152.

Thereafter, the lens is bonded to the front surface of the acoustic module, and the probe 100 shown in FIG. 17 is formed. Prior to bonding of the lens 170, a process for forming at least one of a chemical shield (CS) and a radio frequency (RF) on the front surface of the acoustic module may be further used.

Figure 21:
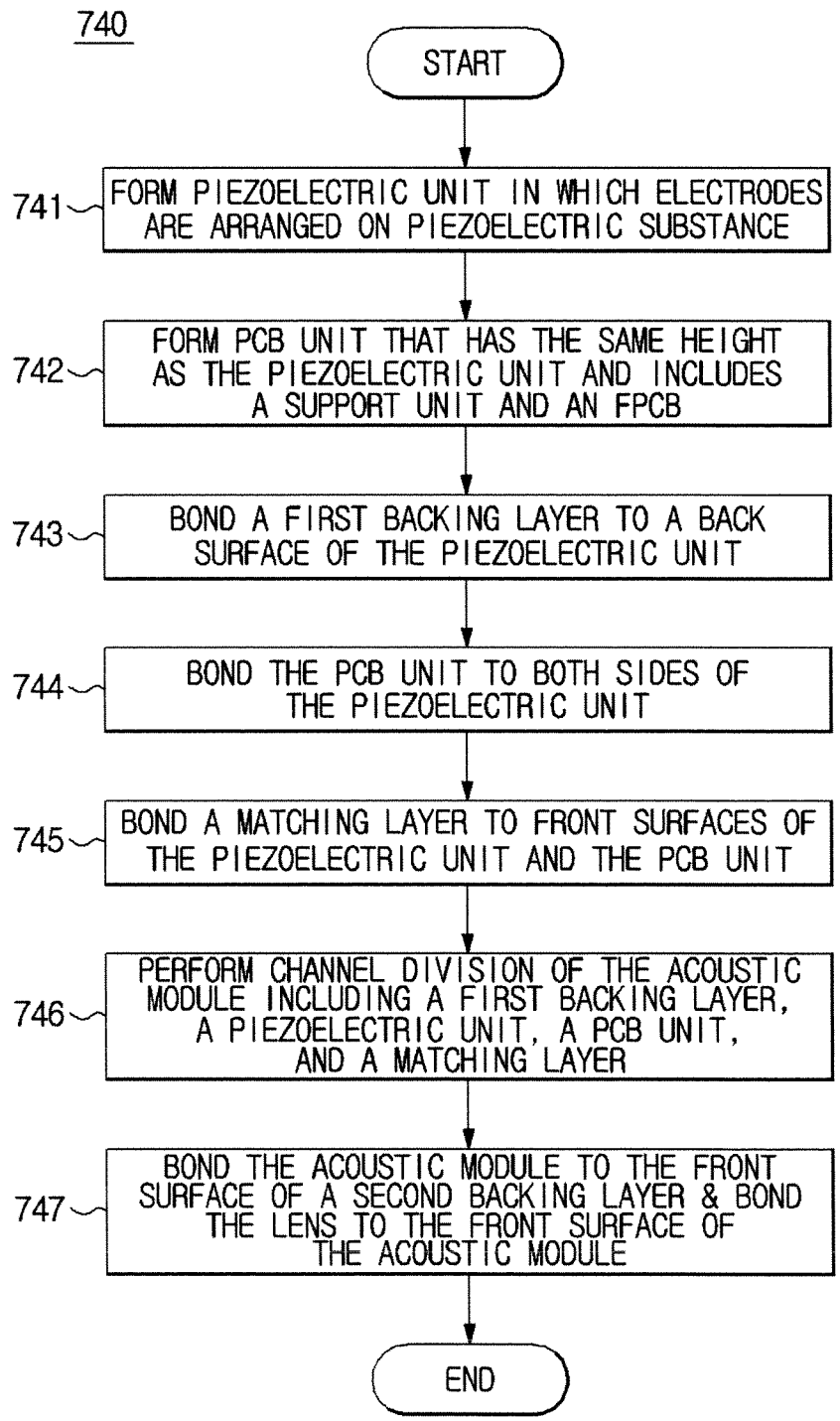
FIG. 21 is a flowchart illustrating a method for manufacturing the probe of the ultrasonic imaging apparatus shown in FIG. 17.

FIG. 21 is a flowchart illustrating a method for manufacturing the probe of the ultrasonic imaging apparatus shown in FIG. 17 according to another embodiment. In a method for forming the probe of the ultrasonic imaging apparatus according to another embodiment, a detailed description of the same or similar process as in FIGS. 5 and 18 will herein be omitted for convenience of description.

Referring to FIG. 21, the piezoelectric unit 110 in which electrodes are arranged in the piezoelectric substance 120 is formed in operation 741. Thereafter, the PCB unit 210 including the support unit 260 and the FPCB 220 is formed to have the same height as the piezoelectric unit 110 in operation 742. The operation 741 may correspond to the operation 711, and the operation 742 may correspond to the operation 712, and as such a detailed description thereof will herein be omitted for convenience of description.

Figure 22:
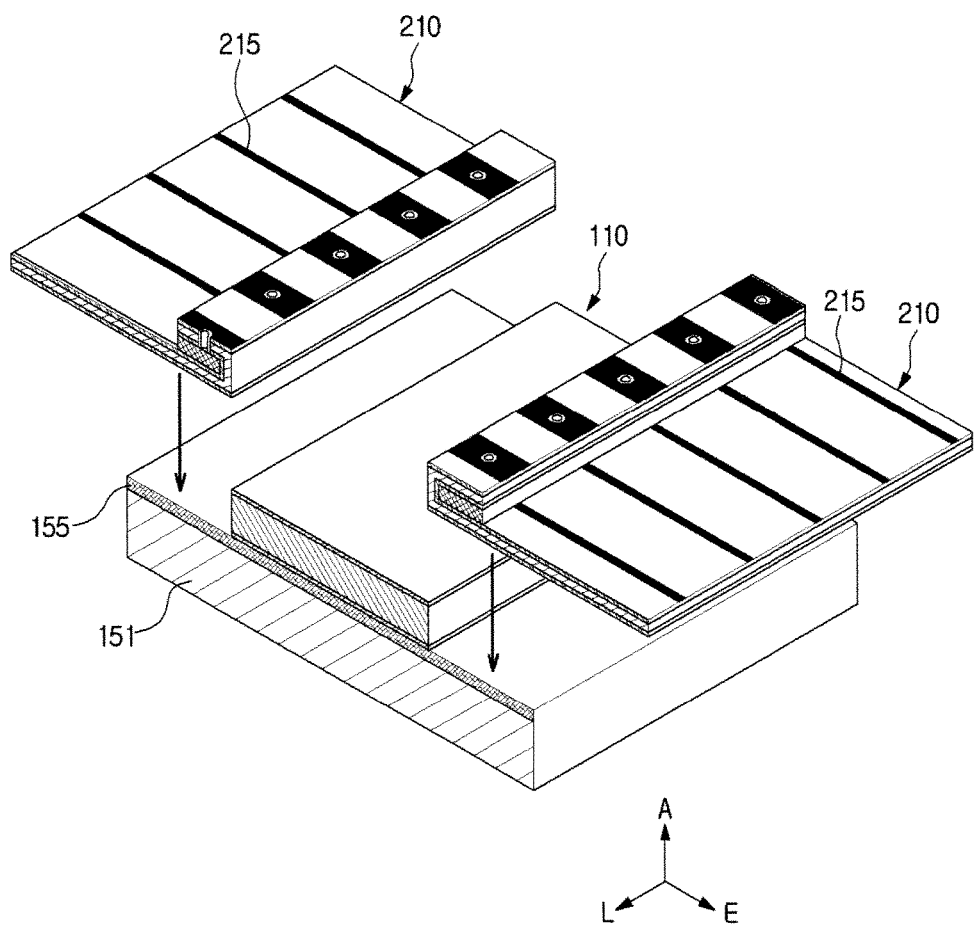
FIG. 22 illustrates another example for bonding a PCB unit 210 and a piezoelectric unit to a first backing layer.

If the PCB unit 210 is formed, the first backing layer 151 may be bonded to the back surface of the piezoelectric substance 110, or the piezoelectric unit 110 may be bonded to the front surface of the first backing layer 151 in operation 743. The PCB unit 210 may be bonded to both sides of the piezoelectric unit 110 in operation 744. FIG. 22 shows another example in which the PCB unit 210 and the piezoelectric unit are bonded to the first backing layer.

Referring to FIG. 22, by depositing a conductive material, such as gold, silver, or copper on the front surface of the first backing layer 151, or by sputtering, plating, or spraying, the electrode layer 155 is formed. The piezoelectric unit 110 may be bonded to the front surface of the first backing layer 151 including the electrode layer 155. If the first backing layer 151 is formed of a conductive material, the electrode layer 155 may be omitted. Here, the piezoelectric unit 110 may be directly bonded to the first backing layer 151.

The first backing layer 151 may have a larger width than the piezoelectric unit 110, and the piezoelectric unit 110 may be bonded to be located at the center of the front surface of the first backing layer 151. One PCB unit 210 may be bonded to one side of the piezoelectric unit 110, and the other one PCB unit 210 may be bonded to the other side thereof. In this case, the conductive line 215 of the PCB unit 210 bonded to one side and the conductive line 215 of the PCB unit 210 bonded to the other side may be arranged to cross each other.

In addition, the bonding of the piezoelectric unit 110 or the bonding of the PCB unit 210 may be achieved by an adhesive. The piezoelectric unit 110 may be bonded to the first backing layer 151 through adhesive, and the PCB unit 210 may be bonded to the first backing layer 151 and the piezoelectric unit 110 through the adhesive. In this case, the adhesive may be formed of a non-conductive material.

In accordance with the bonding of the PCB unit 210 and the piezoelectric unit 110, a first electrode 130a acting as a ground electrode of the piezoelectric unit 110 is connected to the first line unit 221a so that a line unit for a grounding part is formed. A second electrode 130b acting as a signal electrode is connected to the second line unit 221b so that a line unit for a signaling part is formed.

If the PCB unit 210 is bonded, the matching layer 160 is bonded to the front surface of the PCB unit 210 in operation 745. The acoustic module including the first backing layer 151, the piezoelectric unit 110, the PCB unit 210, and the matching layer 160 is channel-divided through dicing in operation 746. The lens 170 is bonded to the front surface of the channel-divided acoustic module in operation 747. Prior to bonding of the lens 170, a process for forming at least one of a chemical shield (CS) and a radio frequency (RF) on the front surface of the acoustic module may be further used. Operations 745 to 747 may respectively correspond to the operations 735 to 737, and as such a detailed description thereof will herein be omitted for convenience of description.

Although the above-mentioned description has exemplarily disclosed that a process (i.e., operation 742) for forming the PCB unit 210 is performed prior to the process (i.e., operation 743) for bonding the piezoelectric unit 110 to the first backing layer 151, it should be noted that the process (i.e., operation 742) for forming the PCB unit 210 can also be achieved after the process (i.e., operation 743) for bonding the piezoelectric unit 110 to the first backing layer 151.

Figure 23:
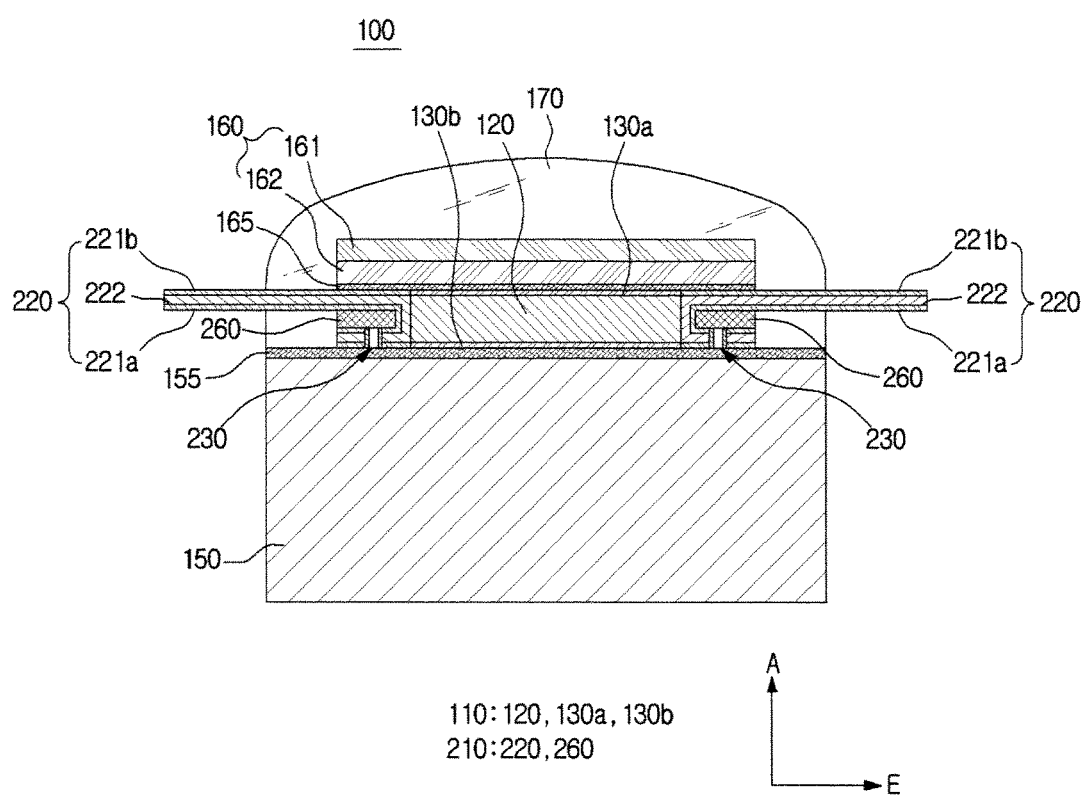
FIG. 23 is a cross-sectional view illustrating a probe of an ultrasonic imaging apparatus according to still another embodiment.

FIG. 23 is a cross-sectional view illustrating a probe for the ultrasonic imaging apparatus according to still another embodiment.

Referring to FIG. 23, the PCB unit 210 includes an FPCB 220 and a support unit 260 supporting the FPCB 220, and may form a folded structure. The support unit 260 may have a predetermined thickness. The PCB unit 210 may have the same height as the piezoelectric unit 110 in response to a thickness variation of the support unit 260. The FPCB 220 may be a double-sided FPCB, and may include a first line unit 221a, a second line unit 220b, and an insulation unit 222.

Since the PCB unit 210 is arranged at a lateral surface of the piezoelectric unit 110, any one of the first line unit 221a and the second line unit 221b may be connected to the first electrode 130a, and the other one thereof may be connected to the second electrode 130b. Referring to FIG. 23, the first line unit 221a connected to the second electrode 130b acting as a signal electrode may be used as a line unit for a signal part, and the second line unit 220b connected to the first electrode 130a of the ground electrode may be used as a line unit for a ground part. In other words, the front surface and the back surface of the PCB unit 210 may be replaced with each other as shown in FIG. 3, and a conductive through hole 230 may be arranged in a backward direction.

An electrode layer 155 may be arranged at the front surface of the backing layer 150. The electrode layer 155 may be disposed among the piezoelectric unit 110, the PCB unit 210, and the backing layer 150, and may be formed of a conductive material. Therefore, the electrode layer 155 may electrically connect the second electrode 130b of the piezoelectric unit 110 to the second line unit 221b of the PCB unit 210.

Likewise, the electrode layer 165 may be arranged at the back surface of the matching layer 160. The electrode 165 may be disposed among the piezoelectric unit 110, the PCB unit 210, and the matching layer 160, and may be formed of a conductive material. Therefore, the electrode layer 165 may electrically connect the first electrode 130a of the piezoelectric unit 110 to the first line unit 221a of the PCB unit 210.

Figure 24:
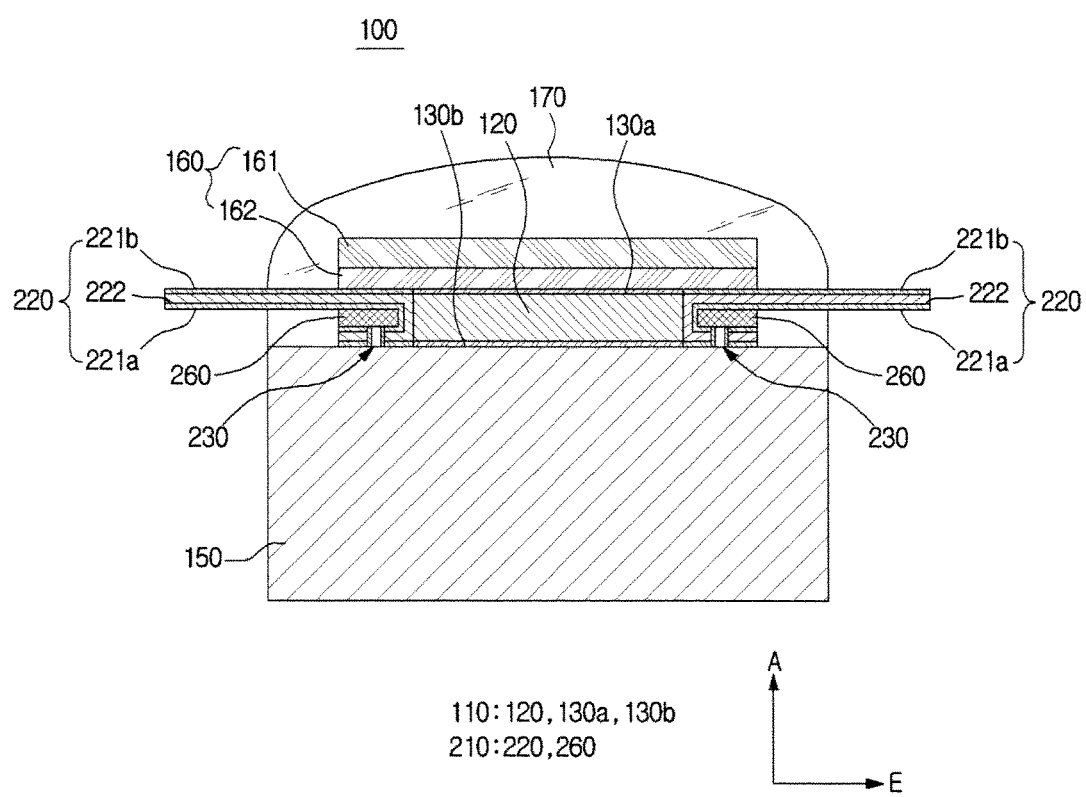
FIG. 24 is a cross-sectional view illustrating a probe of an ultrasonic imaging apparatus according to still another embodiment.

FIG. 24 is a cross-sectional view illustrating a probe for an ultrasonic imaging apparatus according to still another embodiment.

Referring to FIG. 24, the probe 100 for the ultrasonic imaging apparatus may be arranged in a manner that the conductive through hole 230 is located in a backward direction as shown in FIG. 23.

However, the backing layer 150 may be formed of a conductive material, and the electrode layer 155 may be omitted. All parts of the backing layer 150 may be formed of a conductive material, and some parts thereof may also be formed of a conductive material. If some parts of the backing layer 150 are formed of a conductive material, the front surface of the backing layer 150 contiguous to the second electrode 130b of the piezoelectric unit 110 may be formed of a conductive material.

Likewise, the matching layer 160 may be formed of a conductive material, for example, graphite, gold, silver or copper. The electrode layer 165 may be omitted. The matching layer 160 may be formed of a conductive material, or some parts thereof may be formed of a conductive material. If some parts of the matching layer 160 are formed of a conductive material, a back surface of the matching layer 160 contiguous to the first electrode 130a of the piezoelectric unit 110 may be formed of a conductive material.

Figure 25:
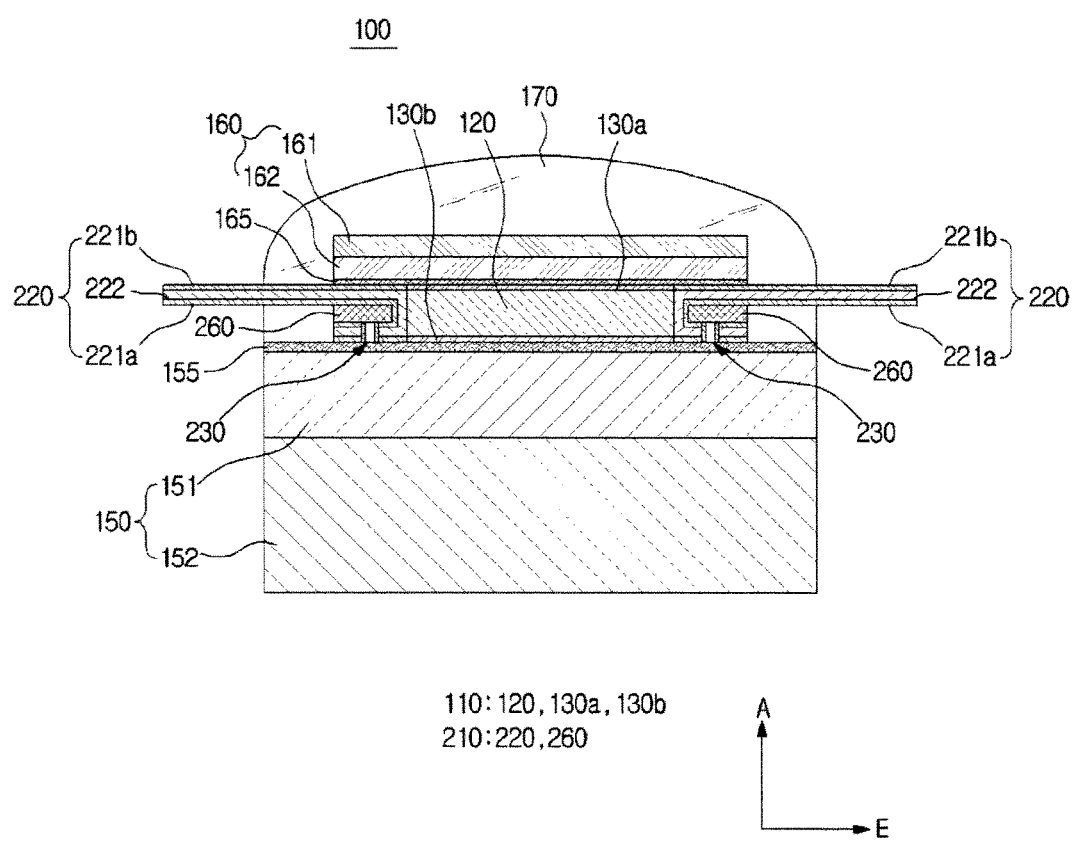
FIG. 25 is a cross-sectional view illustrating a probe of an ultrasonic imaging apparatus according to still another embodiment.

FIG. 25 is a cross-sectional view illustrating a probe for an ultrasonic imaging apparatus according to still another embodiment.

Referring to FIG. 25, the probe 100 for the ultrasonic imaging apparatus may be arranged in a manner that the conductive through hole 230 is located in a backward direction in the same manner as in FIG. 23.

However, the probe 100 may include a backing layer 150 composed of a plurality of layers. For example, the backing layer 150 may include a first backing layer 151 and a second backing layer 152.

The first backing layer 151 and the second backing layer 152 may have different thicknesses. For example, the first backing layer 151 may be thinner than the second backing layer 152. The first backing layer 151 and the second backing layer 152 may have the same shapes. As can be seen from FIG. 25, the first backing layer 151 and the second backing layer 152 may be formed in a block shape. The first backing layer 151 is formed in a block shape, and the second backing layer 152 may have a curved shape having a curvature. The first backing layer 151 and the second backing layer 152 may also have different formats. In accordance with the shapes of the first backing layer 151 and the second backing layer 152, the arrangement shape of the piezoelectric substance 120 and the shape and category of the probe 100 may be determined.

Figure 26:
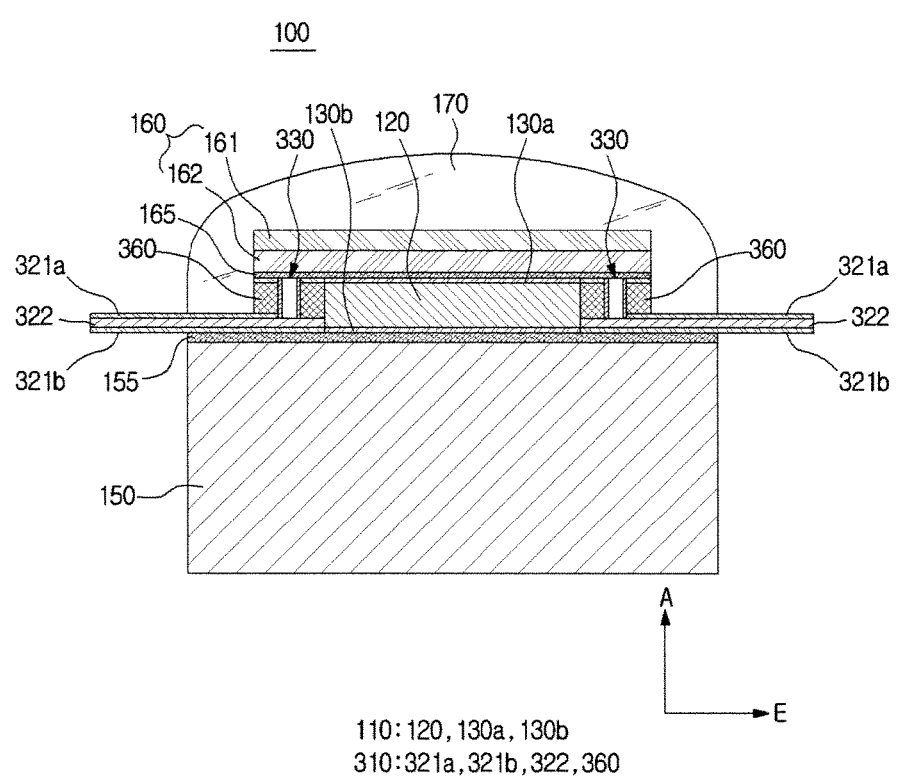
FIGS. 26 and 27 are cross-sectional views illustrating a probe for an ultrasonic imaging apparatus according to still another embodiment.
Figure 27:
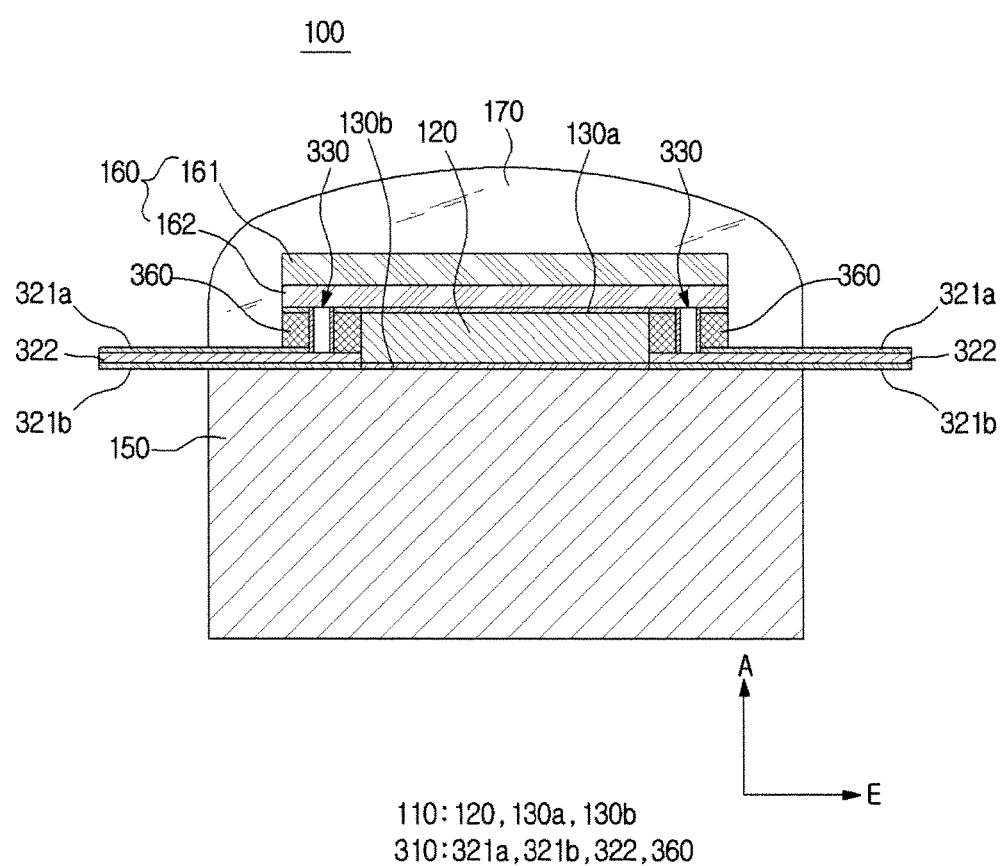

FIGS. 26 and 27 are cross-sectional views illustrating the probe for the ultrasonic imaging apparatus. For convenience of description, the same or similar structures in construction and function as those described in the above-mentioned embodiment are denoted by the same reference numerals, and the explanation thereof will be omitted herein.

Referring to FIGS. 26 and 27, the probe 100 may include a piezoelectric unit 110, a PCB unit 310 provided at a lateral side of the piezoelectric unit 110, a backing layer 150 provided at a back surface of the piezoelectric unit 110, and a matching layer 160 and a lens 170 provided at a front surface of the piezoelectric unit 110. In this case, the piezoelectric unit 110 may include the piezoelectric substance 120 and the electrodes (130a, 130b) respectively formed at the front and back surfaces of the piezoelectric substance 120.

The PCB unit 310 may be formed by integrating a flexible printed circuit board (i.e., FPCB) and a rigid printed circuit board (RPCB) into one unit. In more detail, the PCB unit 310 may include an FPCB and a rigid support unit 360 to support the FPCB. A rigid support unit 360 is coupled to the FPCB, resulting in formation of the rigid-flexible printed circuit board (R-FPCB). A method for forming the PCB unit 310 will hereinafter be described in detail.

The PCB unit 310 is a double-sided PCB, and includes a first line unit 321a, a second line unit 321b, an insulation unit 322, and a support unit 260. The PCB unit 310 may have the same height as the piezoelectric unit 110 in response to a thickness variation of the support unit 360, and may be arranged at both sides of the piezoelectric unit 110.

The insulation unit 322 may be disposed between the first line unit 321a and the second line unit 321b. The insulation unit 322 may be formed of a soft insulation material. For example, the insulation unit 322 may be formed of a polyester (PET) film, a polyimide (PI) film, or the like, but not limited thereto. The insulation unit 222 may be formed of other soft insulation materials well known to those skilled in the art.

The first line unit 321a and the second line unit 321b may be spaced apart from each other by the insulation unit 322 interposed therebetween. As described above, since the insulation unit 322 is formed of an insulation material, electric connection between the first line unit 321a and the second line unit 321b is severed through the insulation unit 322.

Each of the first line unit 321a and the second line unit 321b may include a plurality of conductive lines (See 315 of FIG. 32). The plural conductive lines 215 may be spaced apart from each other at intervals of a predetermined distance in the lateral direction (L), and the position of the conductive line 315 of the first line unit 321a is opposite to the position of the conductive line 315 of the second line unit 321b. The conductive line 315 of the PCB unit 310 located at one lateral surface of the piezoelectric unit 110 and the conductive line 315 of the PCB unit 310 located at the other lateral surface are arranged to cross each other, and a detailed description thereof will hereinafter be described.

Since the PCB unit 310 is arranged at a lateral surface of the piezoelectric unit 110, any one of the first line unit 321a and the second line unit 321b is coupled to the first electrode 130a, and the other one is coupled to the second electrode 130b. For convenience of description and better understanding of the present invention, the first line unit 321a is coupled to the first electrode 130a, and the second line unit 321b is coupled to the second electrode 130b. The conductive line 315 of the first line unit 221a may be electrically coupled to the first electrode 130a acting as a ground electrode, so that the first line unit 321a may be used as a ground line. In addition, the conductive line 315 of the second line unit 321b may be electrically coupled to the second electrode 130b acting as a signal electrode, so that the second line unit 321b may be used as a line unit for signaling.

In addition, since the PCB unit 310 is provided at a lateral surface of the piezoelectric unit 110, instead of the front or back surface of the piezoelectric unit 110, i.e., since the PCB unit 310 is not provided in the progressing direction of ultrasonic waves, ultrasonic acoustic characteristics can be prevented from being changed by the PCB unit 310.

The support unit 360 is provided at a connection part of the first line unit 321a, so that the support unit 360 supports the PCB unit 310. The support unit 360 may be formed of an insulation material, and may also be formed of a conductive material. The support unit 360 may be formed of a rigid material, and may be formed in a block shape. For example, the support unit 360 may include a ceramic material, and the ceramic block formed as a block shape may construct the support unit 360.

The support unit 360 may be formed to have a predetermined thickness. As described above, the PCB unit 310 may have the same height as the piezoelectric unit 110 through thickness control of the support unit 360.

An electrode layer 155 may be arranged at the front surface of the backing layer 150 as shown in FIG. 26. The electrode layer 155 may be disposed among the piezoelectric unit 110, the PCB unit 210, and the backing layer 150. The electrode layer 155 may be formed of a conductive material such as gold, silver or copper, or may be formed by deposition, sputtering, plating, spraying or the like. Therefore, the electrode layer 155 may electrically connect the second electrode 130b of the piezoelectric unit 110 to the second line unit 321b of the PCB unit 310.

The backing layer 150 may be formed of a conductive material. The electrode layer 155 may be omitted as shown in FIG. 27. The backing layer 150 may be formed of a conductive material, or some parts thereof may also be formed of a conductive material. If some parts of the backing layer 150 are formed of a conductive material, the front surface of the backing layer 150 contiguous to the second electrode 130b of the piezoelectric unit 110 may be formed of a conductive material.

An electrode layer 165 may be arranged at the back surface of the matching layer 160 as shown in FIG. 26. The electrode layer 165 may be disposed among the piezoelectric unit 110, the PCB unit 310, and the matching layer 160. The electrode layer 165 may be formed of a conductive material such as gold, silver or copper, or may be formed by deposition, sputtering, plating, spraying or the like. Therefore, the electrode layer 165 may electrically connect the first electrode 130a of the piezoelectric unit 110 to the first line unit 321a of the PCB unit 310.

The matching layer 160 may be formed of a conductive material, for example, graphite, gold, silver or copper. The electrode layer 165 may be omitted as shown in FIG. 27. The matching layer 160 may be formed of a conductive material, or some parts thereof may be formed of a conductive material. If some parts of the matching layer 160 are formed of a conductive material, a back surface of the matching layer 160 contiguous to the first electrode 130a of the piezoelectric unit 110 may be formed of a conductive material.

Figure 28:
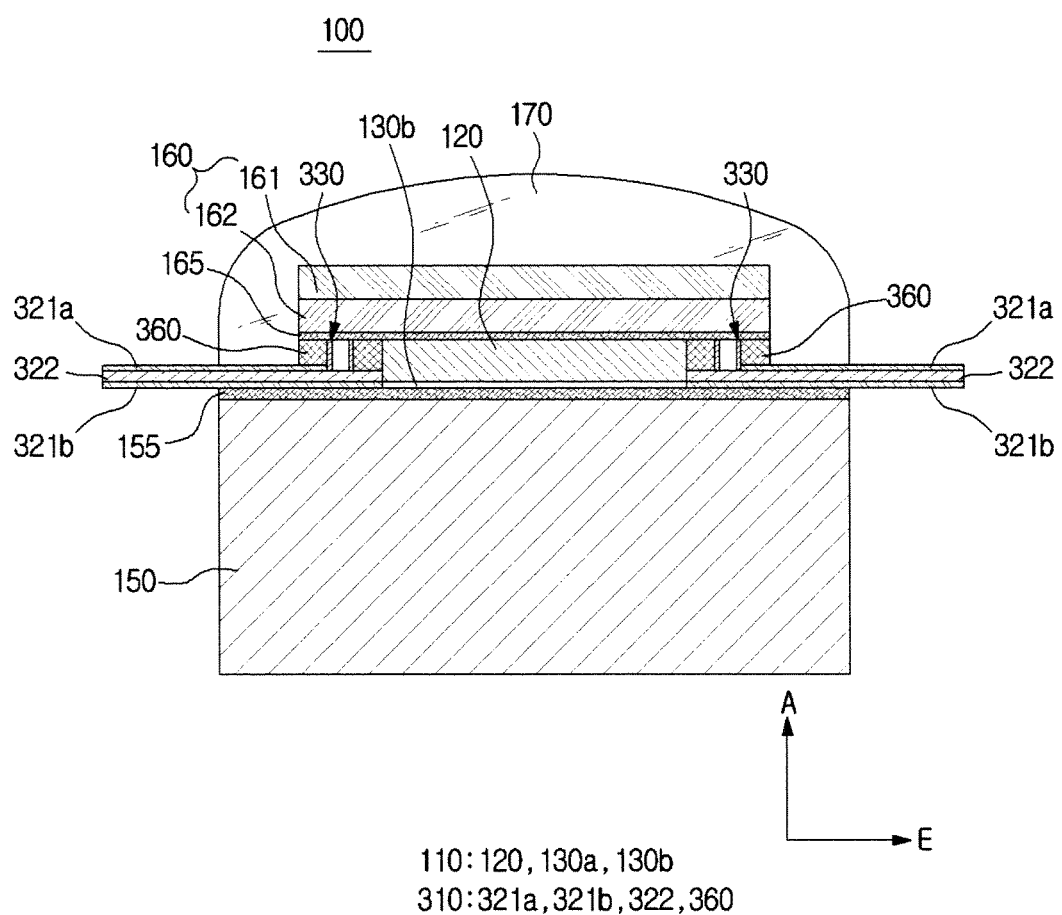
FIG. 28 is a cross-sectional view illustrating a probe for an ultrasonic imaging apparatus according to still another embodiment.

FIG. 28 is a cross-sectional view illustrating a probe for the ultrasonic imaging apparatus according to still another embodiment.

Referring to FIG. 28, the first electrode 130a may be omitted from the piezoelectric unit 110, and the first line unit 321a may be omitted from the PCB unit 310. For example, the PCB unit 310 including the first line unit 321a is arranged at both sides of the piezoelectric unit 110 having the first electrode 130a, and the first electrode 130a and the first line unit 321a may be removed by dicing the front surfaces of the piezoelectric unit 110 and the PCB unit 310. By dicing, the height of the piezoelectric unit 110 may be identical to the height of the PCB unit 310. In addition, the PCB unit 310 not including the first line unit 321a is arranged at both sides of the piezoelectric unit 110 not including the first electrode 130a. By dicing the front surfaces of the piezoelectric unit 110 and the PCB unit 310, the height of the piezoelectric unit 110 may be identical to the height of the PCB unit 310.

In this case, the electrode layer 165 arranged in the matching layer 160 may be used as a ground electrode and a line unit for a ground part, instead of the first electrode 130a and the first line unit 321a.

Figure 29:
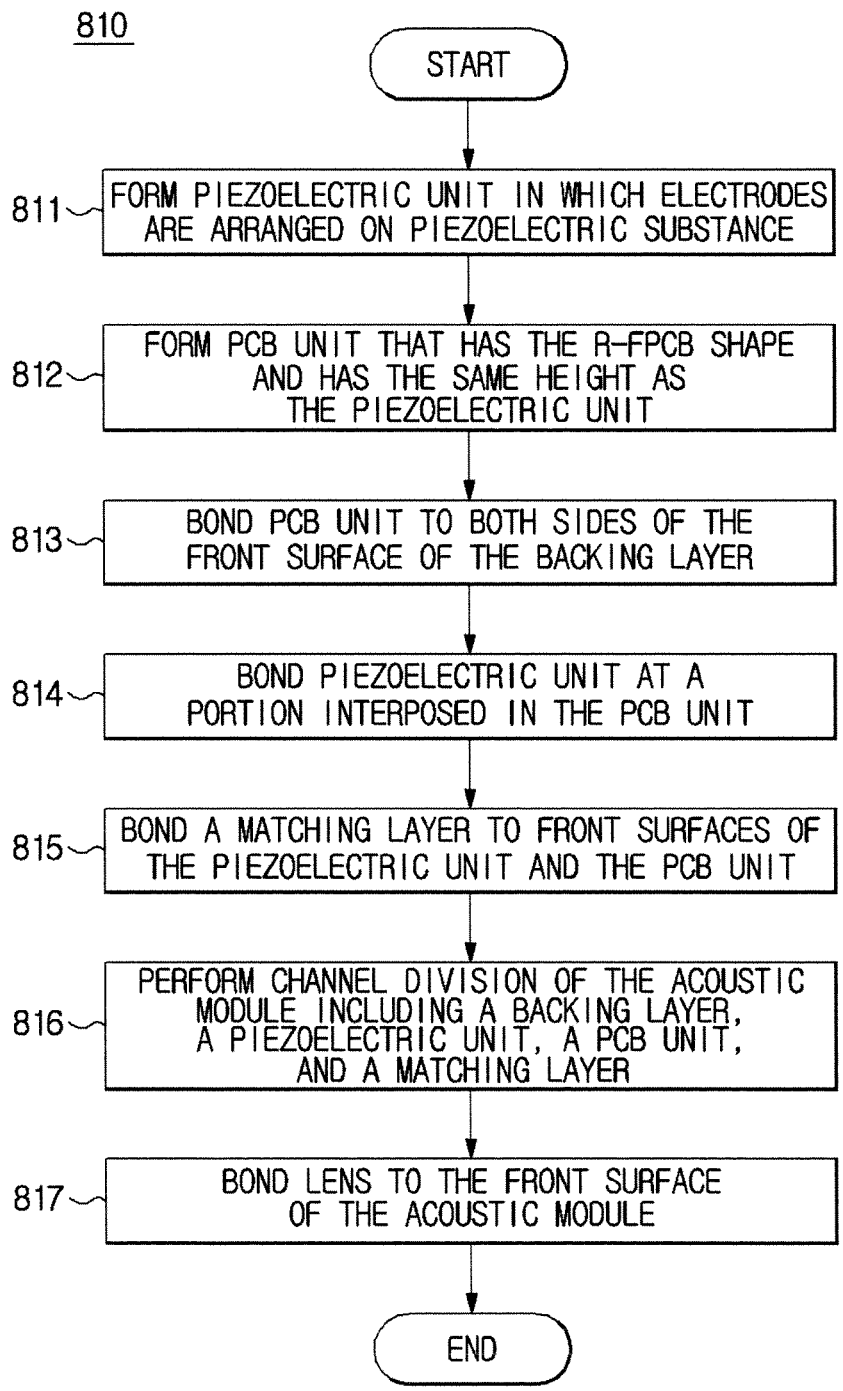
FIG. 29 is a flowchart illustrating a method for manufacturing the probe of the ultrasonic imaging apparatus shown in FIG. 26.

FIG. 29 is a flowchart illustrating a method for manufacturing the probe of the ultrasonic imaging apparatus shown in FIG. 26 according to another embodiment. In a method for forming the probe of the ultrasonic imaging apparatus, a detailed description of the same or similar process as in FIG. 5 will herein be omitted for convenience of description.

Referring to FIG. 29, the piezoelectric unit 110 in which electrodes are arranged on the piezoelectric substance 120 is formed in operation 811. Operation 911 is identical to the operation 711.

Thereafter, the PCB unit 310 having an R-FPCB format is formed to have the same height as the piezoelectric unit 110 in operation 812. FIGS. 30 to 32 exemplarily illustrate the method for forming the PCB unit 310.

Referring to FIG. 30, an FPCB 320 having a soft insulation unit 322 is provided. The FPCB 320 is a double-sided FPCB. A plurality of conductive lines may be respectively printed on the front surface and the back surface of the FPCB 320 on the basis of the insulation unit 322 interposed therebetween. In this case, a front line unit P3 including a plurality of conductive lines printed on the front surface of the insulation unit 322 is defined, and a back line unit P4 including a plurality of conductive lines printed on the back surface of the insulation unit 322 is defined.

The conductive lines of the front line unit P3 are printed on the front surface of the insulation unit 322 while being spaced apart from each other by a predetermined distance, and the conductive lines of the back line unit P4 are printed on the back surface of the insulation unit 322 while being spaced apart from each other by a predetermined distance. In this case, the position of the conductive line of the front line unit P3 is opposite to the position of the conductive line of the back line unit P4. In addition, the conductive lines of the front line unit P3 are printed to have a shorter length than the conductive lines of the back line unit P4.

Although the conductive lines may be printed at intervals of a predetermined distance as shown in FIG. 30(b), it should be noted that different both ends of the conductive lines may also be printed to have different spacing values. When printing the conductive lines, the spacing between the conductive lines may be gradually reduced or reduced in the range from one end to the other end of the conductive lines. In addition, the conductive lines may be printed to have a constant thickness, or both ends of the conductive lines may also be printed to have different thicknesses. The thickness of the conductive lines may be gradually reduced or increased in the range from one end to the other end of the conductive lines.

Referring to FIG. 31, the rigid support unit 360 is bonded to one end of the front surface of the FPCB 320, and the support unit 360 may have a predetermined width to cover one end of the front line unit P3. If the support unit 360 is bonded, a plurality of conductive lines may be printed on the front surface of the support unit 360. Upon printing completion of the conductive lines, the support unit 360 may also be bonded. In this case, the support layer line unit P5 is defined to include a plurality of conductive lines printed on the front surface of the support unit 360.

The conductive lines of the support layer line unit P5 are printed on the front surface of the support unit 360 while being spaced apart from each other by a predetermined distance, and the position of the above conductive lines may be opposite to the position of the conductive lines of the front line unit P3. Preferably, the conductive lines contained in the support layer line unit P5 may have a larger thickness than the conductive lines of the remaining parts.

As described above, the rigid support unit 360 may be bonded to the FPCB 320, and the support layer line unit P5 is printed, resulting in R-FPCB formation.

A through hole 331 is located at one end of the R-FPCB (i.e., at a bonded part of the support unit 360) as shown in FIG. 32(*a*). The through hole 331 is formed on the conductive lines, and electric connection of the support layer line units P5 is severed by the through hole interposed therebetween. Likewise, electric connection of the front line unit P3 is also severed through the through hole 331.

After generation of the through hole 331, the through hole 331 may be plated or fabricated with a conductive material such as gold, silver or copper. Because the through hole 331 is fabricated with the conductive material 332, the support layer line unit P5 and the front line unit P3 may be electrically interconnected as shown in FIG. 32(*b*). Therefore, a conductive through hole 330 is defined to include the through hole 331 and the conductive material 332.

As described above, the conductive through hole 330 is formed in the R-FPCB, and formation of the PCB unit 310 is completed. However, although the above-mentioned description illustrates one example for forming the PCB unit 310, the scope or spirit of the present invention is not limited thereto. Assuming that the double-sided R-FPCB is formed, the PCB unit 310 may also be formed by other steps or other structures.

Figure 33:
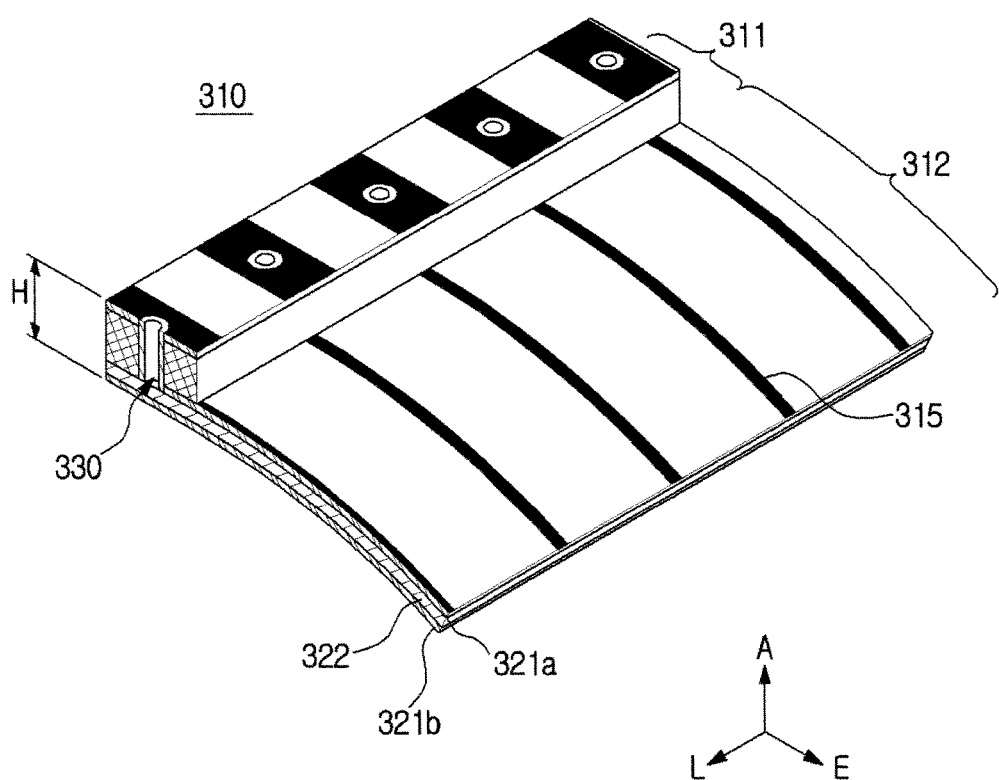
FIG. 33 illustrates the PCB unit having a Rigid-Flexible Printed Circuit Board (R-FPCB) format.
Figure 34:
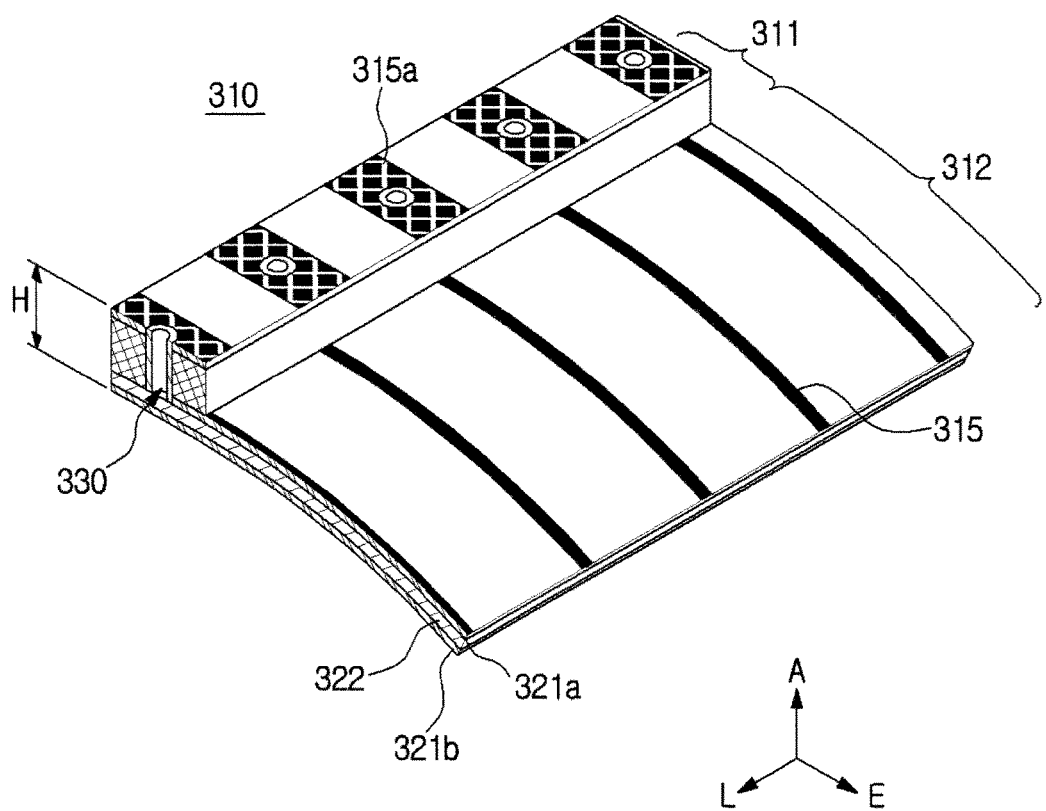
FIG. 34 illustrates the PCB unit having an R-FPCB format.

FIG. 33 illustrates a PCB unit having a Rigid-Flexible Printed Circuit Board (R-FPCB) format according to one embodiment. FIG. 34 illustrates a PCB unit having an R-FPCB format according to another embodiment.

Referring to FIGS. 33 and 34, a plurality of conductive lines 315 may be spaced apart from each other by a predetermined distance on the PCB unit 310. The conductive through hole 330 is arranged in a forward direction of the PCB unit 210, so that the front line unit P3 can be electrically connected to the support layer line unit P5. The conductive through hole 330 is formed on the conductive lines 315. The front line unit P3, the conductive through hole 330, and the support layer line unit P5 connected to both the front line unit P3 and the conductive through hole 330 is defined as a first line unit 321*a*, and the back line unit P4 is defined as a second line unit 321*b*.

A conductive line of the support layer line unit P5 (i.e., conductive line parts located at the front of the PCB unit 210) may have a larger thickness than the remaining parts. Referring to FIG. 34, a groove 315*a* may be formed at a conductive line part arranged at the front of the PCB unit 210. The groove 315*a* may be formed by etching of the conductive line. For etching, the dry etch method or the wet etch method can be applied. Although the groove 315*a* may form lattice structures having a regular spacing, it should be noted that a net structure having irregular spacing may be formed as necessary. Because of formation of the groove 315*a*, the conductive line 215 may be divided into a plurality of regions, and the plural regions may be formed in various shapes, for example, a diamond shape, a rectangular shape, a triangular shape, etc.

A specific part bonded to the rigid support unit 360 of the PCB unit 310 may construct the RPCB 311, and a specific part in which the soft insulation unit 322 is formed may construct the FPCB 312. Meanwhile, the height of the PCB unit 210 may be adjusted through a thickness of the support unit 260 and the width of the groove 240, such that the PCB unit 210 may be formed to have the same height H as the piezoelectric unit 110.

If the PCB unit 310 is formed in operation 812, the PCB unit 310 is bonded to both sides of the front surface of the backing layer 150 in operation 813. The piezoelectric unit 110 is bonded between the PCB units 310 in operation 814.

Figure 35:
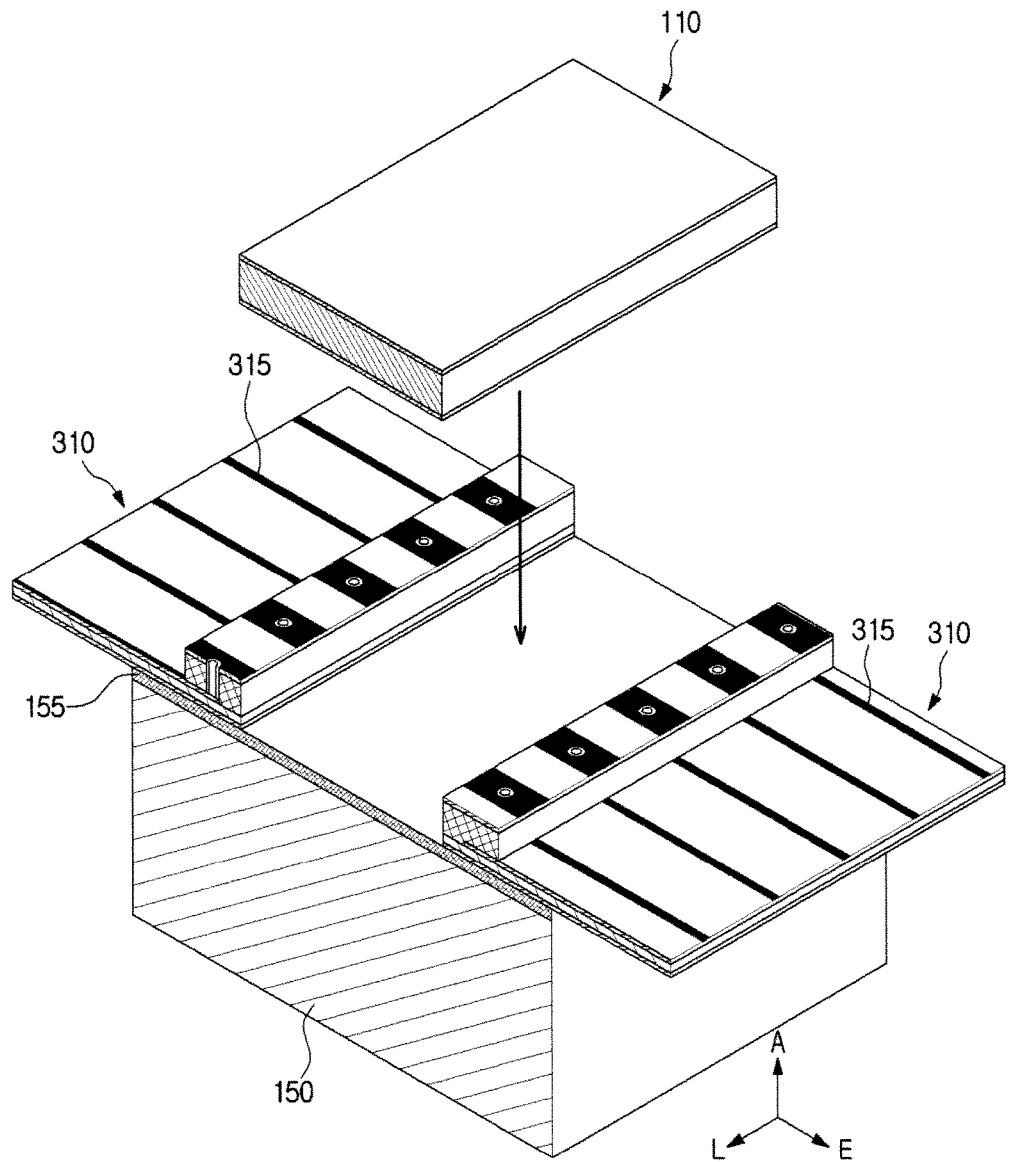
FIG. 35 illustrates a method for bonding the PCB unit and the piezoelectric unit to a backing layer.

FIG. 35 illustrates a method for bonding the PCB unit and the piezoelectric unit to a backing layer.

Referring to FIG. 35, by depositing a conductive material, such as gold, silver, or copper on the back surface of the backing layer 150, or by sputtering, plating, or spraying, the electrode layer 155 is formed. The PCB unit 310 is bonded to both sides of the front surface of the backing layer 150 including the electrode layer 155. If the backing layer 150 is formed of a conductive material, the electrode layer 155 may be omitted. Here, the PCB unit 310 may be directly bonded to the backing layer 150.

The backing layer 150 may have a larger width than the piezoelectric unit 110, and one PCB unit 310 may be bonded to each of one side and the other side of the front surface of the backing layer 150 on the basis of a predetermined interval corresponding to the width of the piezoelectric unit 110. In this case, the conductive line 315 of the PCB unit 310 bonded to the one side and the conductive line 315 of the PCB unit 310 bonded to the other side are arranged to cross each other. The piezoelectric unit 110 is bonded to be meshed with the spacing formed by the PCB unit 310.

The bonding (or attachment) of the PCB unit 310 or the bonding (or attachment) of the piezoelectric unit 110 may be achieved through an adhesive. The PCB unit 310 may be bonded to the backing layer 150 through an adhesive. The piezoelectric unit 110 may be bonded to the backing layer 150 and the PCB unit 310 through an adhesive. Here, the adhesive may be formed of a non-conductive material.

In accordance with the bonding between the PCB unit 210 and the piezoelectric unit 110, a first electrode 130*a* serving as aground electrode of the piezoelectric unit 110 is connected to the first line unit 321*a* so as to form a line unit for grounding, and a second electrode 130*b* serving as a signal electrode is connected to the second line unit 321*b* so as to form a line unit for signaling.

If the piezoelectric unit 110 is bonded, the matching layer 160 is bonded to the front surfaces of the piezoelectric unit 110 and the PCB unit 310 so that the acoustic module is formed in operation 815. Here, the acoustic module is a module formed by bonding of the matching layer 160, and includes the backing layer 150, the piezoelectric unit 110, the PCB unit 310, and the matching layer 160.

The acoustic module including the backing layer 150, the piezoelectric unit 110, the PCB unit 310, and the matching layer 160 is channel-divided through dicing in operation 816. The lens 170 is bonded to the front surface of the channel-divided acoustic module, so that the probe 100 shown in FIG. 26 is formed in operation 817. Prior to bonding of the lens 170, a process for forming at least one of a chemical shield (CS) and a radio frequency (RF) on the front surface of the acoustic module may be further used. The operations 815 to 817 may respectively correspond to the operations 715 to 717, and as such a detailed description thereof will herein be omitted for convenience of description.

Meanwhile, after the piezoelectric unit 110 is bonded in operation 814, a method for dicing the front surface of the piezoelectric unit 110 and the PCB unit 310 may be further used. By dicing, the piezoelectric unit 110 and the PCB unit 310 can more correctly and easily form the same height. If the matching layer 160 is bonded to the dicing surface and channel division and lens bonding are performed in operations 816 and 817, the probe 100 shown in FIG. 28 may be formed. In this case, the electrode layer 165 arranged in the matching layer 160 may be used as a ground electrode or a line unit of grounding, instead of the first electrode 130a and the first line unit 321a.

Figure 36:
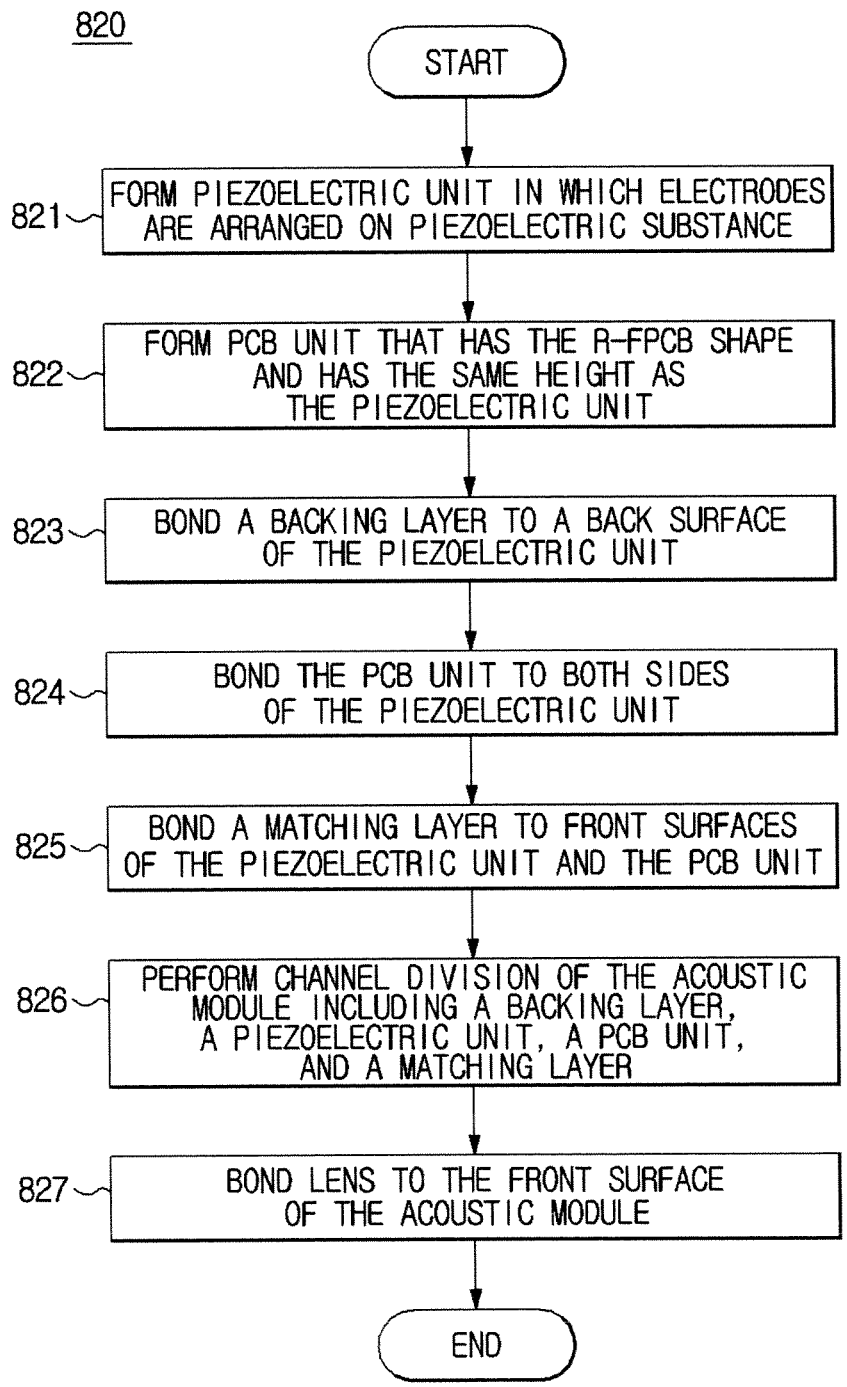
FIG. 36 is a flowchart illustrating a method for manufacturing the probe of the ultrasonic imaging apparatus shown in FIG. 26.

FIG. 36 is a flowchart illustrating a method for manufacturing the probe of the ultrasonic imaging apparatus shown in FIG. 26 according to another embodiment. In a method for forming the probe of the ultrasonic imaging apparatus, a detailed description of the same or similar process as in FIGS. 5 and 29 will herein be omitted for convenience of description.

Referring to FIG. 36, the piezoelectric unit 110 in which electrodes are arranged on the piezoelectric substance 120 is formed in operation 821. Thereafter, the PCB unit 110 having an R-FPCB format is formed to have the same height as the piezoelectric unit 110 in operation 822. Operations 821 and 822 may respectively correspond to operations 811 and 812.

If the PCB unit 310 is formed, the PCB unit 310 is bonded to the front or back surface of the piezoelectric unit 110 in operation 823. The PCB unit 310 is bonded at both sides of the piezoelectric unit 110 in operation 824.

Figure 37:
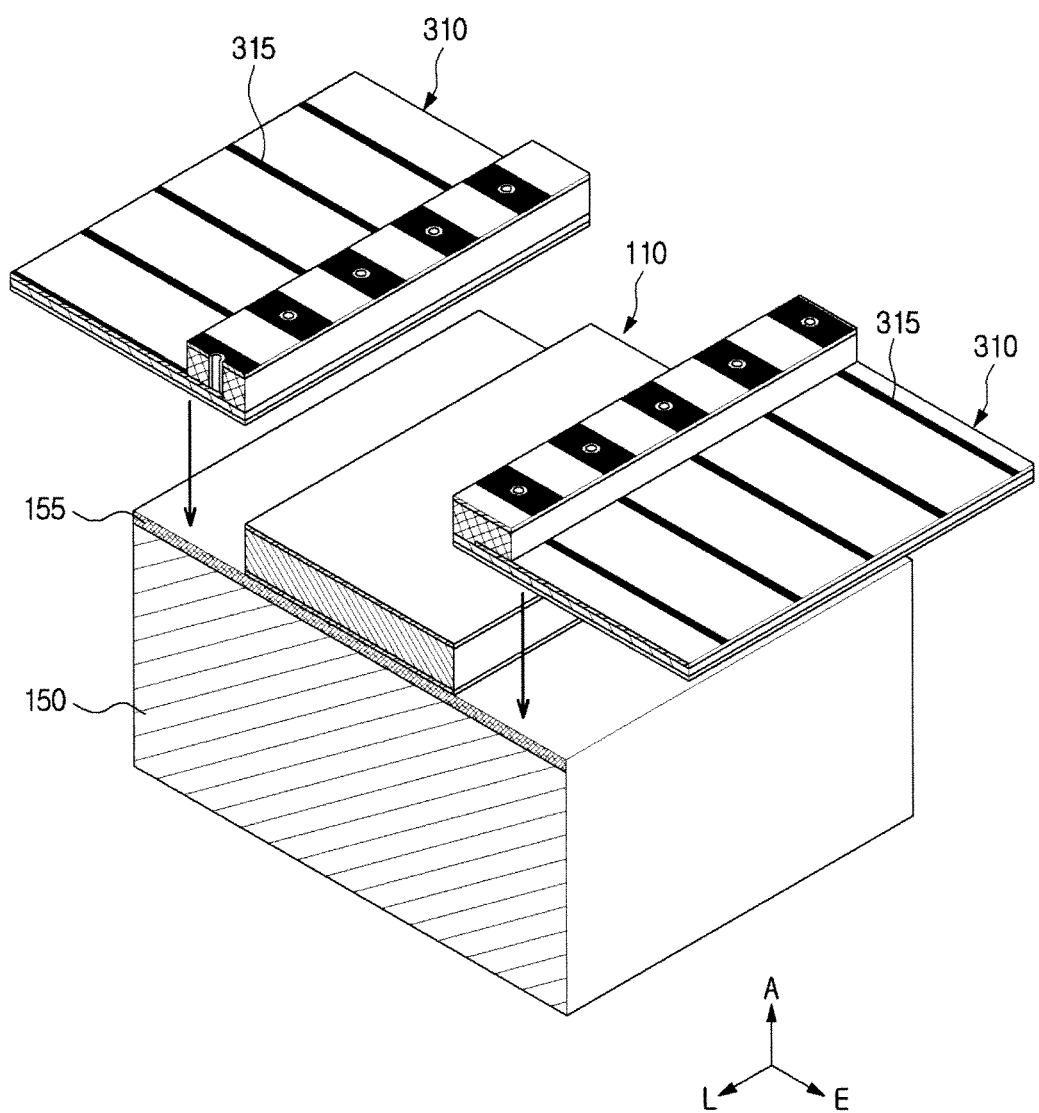
FIG. 37 illustrates another example for bonding a PCB unit 310 and a piezoelectric unit to a backing layer.

FIG. 37 illustrates another exemplary method for bonding the PCB unit 310 and the piezoelectric unit to the backing layer.

Referring to FIG. 37, by depositing a conductive material, such as gold, silver, or copper on the front surface of the backing layer 150, or by sputtering, plating, or spraying, the electrode layer 155 is formed. The piezoelectric unit 110 is bonded to a front surface of the backing layer 150 including the electrode layer 155. If the backing layer 150 is formed of a conductive material, the electrode layer 155 may be omitted. Here, the PCB unit 110 may be directly bonded to the backing layer 150.

The backing layer 150 may have a larger width than the piezoelectric unit 110, and one PCB unit 110 may be bonded to be located at the center part of the front surface of the backing layer 150. The PCB unit 310 is bonded to each of one side and the other side of the piezoelectric unit 110. In this case, the conductive line 315 of the PCB unit 310 bonded to the one side and the conductive line 315 of the PCB unit 310 bonded to the other side are arranged to cross each other.

In addition, the bonding (or attachment) of the piezoelectric unit 110 or the bonding (or attachment) of the PCB unit 310 may be achieved through an adhesive. The piezoelectric unit 110 may be bonded to the backing layer 150 through an adhesive. Here, the adhesive may be formed of a non-conductive material.

In accordance with the bonding between the PCB unit 310 and the piezoelectric unit 110, a first electrode 130a serving as a ground electrode of the piezoelectric unit 110 is connected to the first line unit 321a so as to form a line unit for grounding, and a second electrode 130b serving as a signal electrode is connected to the second line unit 321b so as to form a line unit for signaling.

If the PCB unit 310 is bonded, the matching layer 160 is bonded to the front surfaceas of the piezoelectric unit 110 and the PCB unit 210 in operation 825. The acoustic module including the backing layer 150, the piezoelectric unit 110, the PCB unit 310, and the matching layer 160 is channel-divided through dicing in operation 826. The lens 170 is bonded to the front surface of the channel-divided acoustic module, so that the probe 100 shown in FIG. 26 is formed in operation 827. Prior to bonding of the lens 170, a process for forming at least one of a chemical shield (CS) and a radio frequency (RF) on the front surface of the acoustic module may be further used. Operations 825 to 827 may respectively correspond to the operations 715 to 717, and as such a detailed description thereof will herein be omitted for convenience of description.

Meanwhile, after the PCB unit 310 is bonded in operation 824, a method for dicing the front surface of the piezoelectric unit 110 and the PCB unit 310 may be further used. If the matching layer 160 is bonded to the dicing surface and channel division and lens bonding are performed in operations 816 and 817, the probe 100 shown in FIG. 28 may be formed.

Although the above-mentioned description has exemplarily disclosed that a process (i.e., operation 822) for forming the PCB unit 310 is performed prior to the process (i.e., operation 823) for bonding the piezoelectric unit 110 to the backing layer 150, it should be noted that the process (i.e., operation 822) for forming the PCB unit 310 can also be achieved after the process (i.e., operation 823) for bonding the piezoelectric unit 110 to the backing layer 150.

Figure 38:
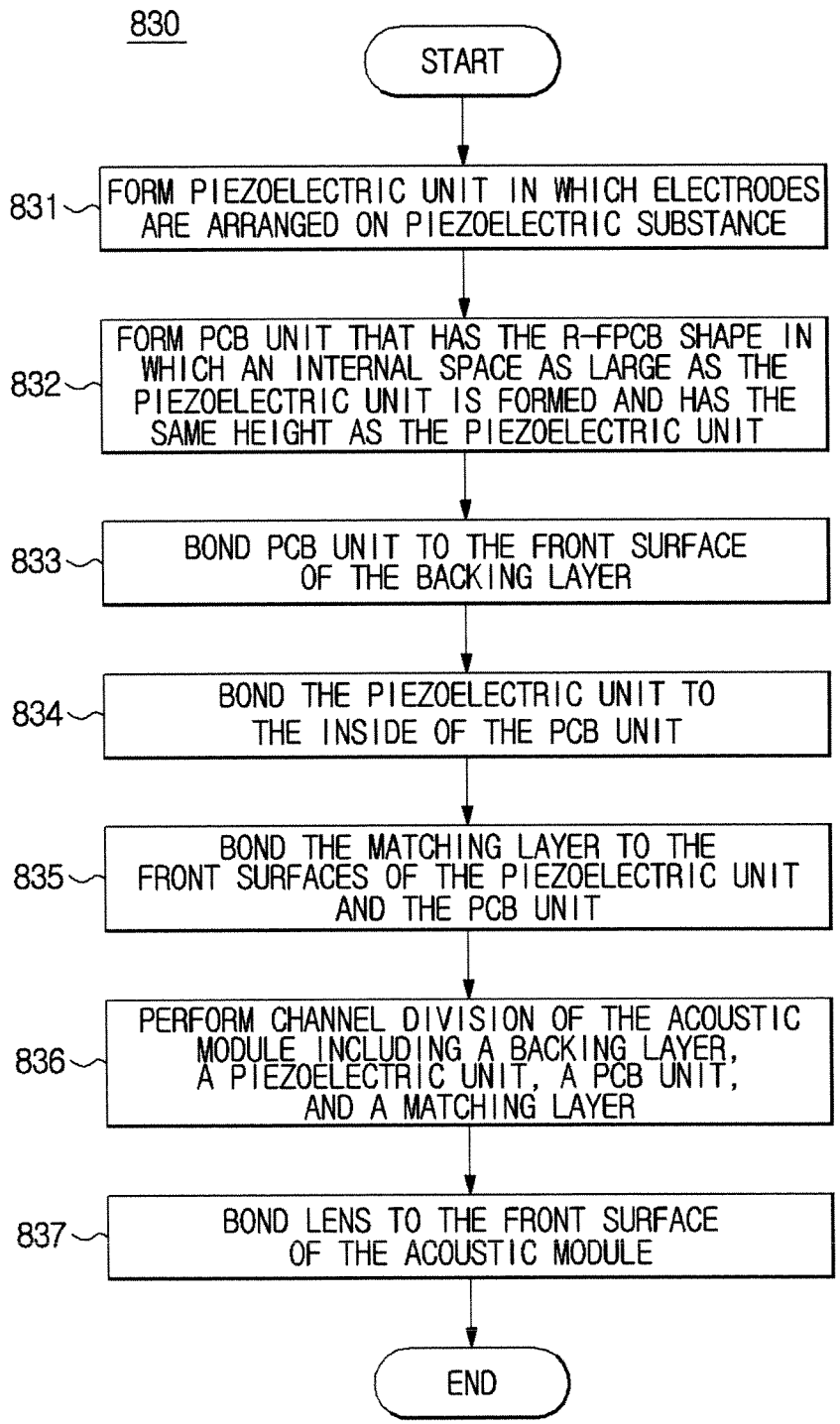
FIG. 38 is a flowchart illustrating a method for manufacturing the probe of the ultrasonic imaging apparatus shown in FIG. 26.

FIG. 38 is a flowchart illustrating a method for manufacturing the probe of the ultrasonic imaging apparatus shown in FIG. 26.

Referring to FIG. 38, the piezoelectric unit 110 in which electrodes are arranged in the piezoelectric substance 120 is formed in operation 831. The operation 831 may correspond to the operation 811, and as such a detailed description thereof will herein be omitted for convenience of description.

Thereafter, the PCB unit 310 includes the R-FPCB in which an internal space as large as the piezoelectric unit 110 is formed, and the PCB unit 310 having the same height as the piezoelectric unit 110 in operation 832.

Figure 39:
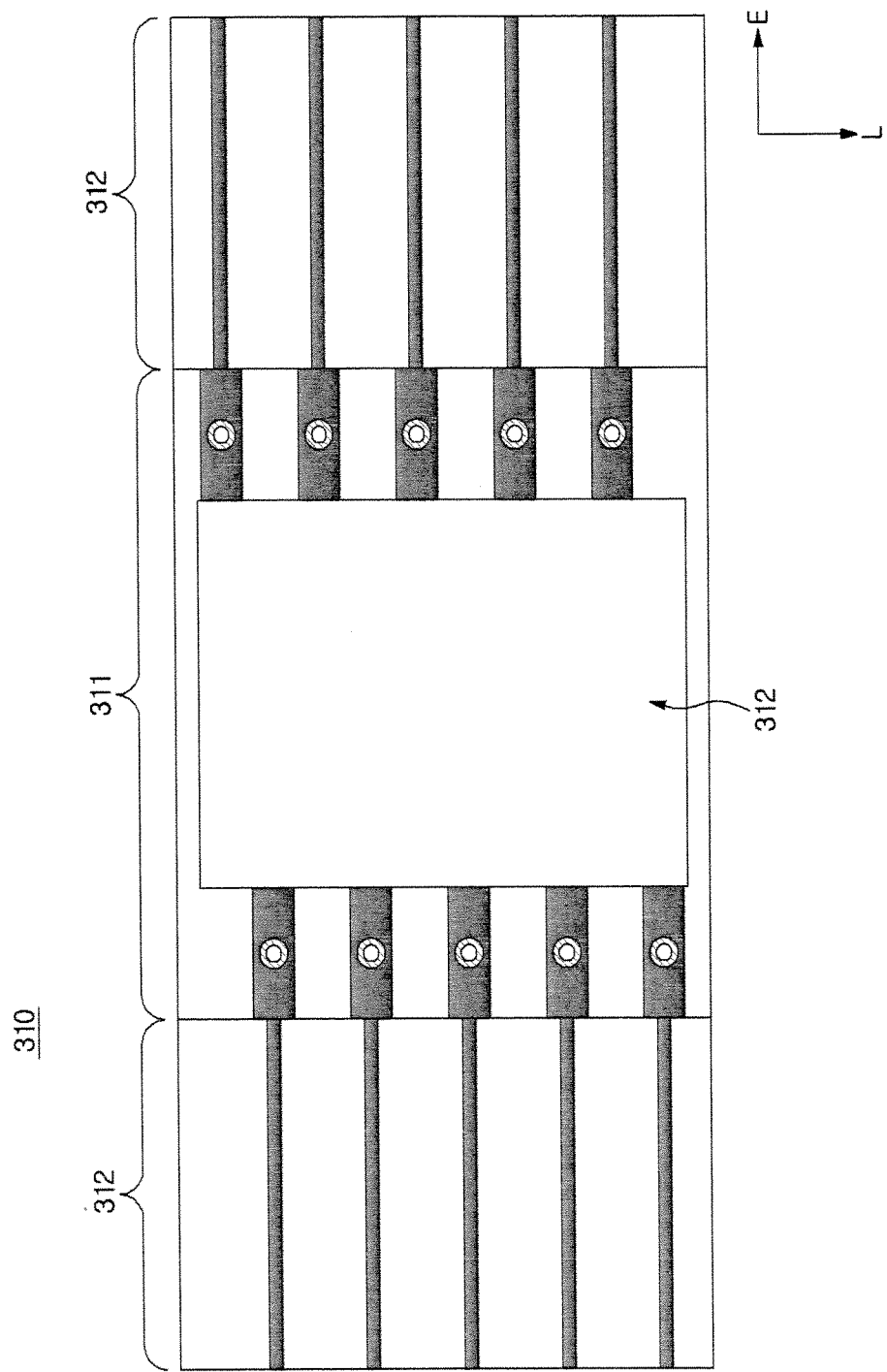
FIG. 39 is a plan view illustrating a PCB unit having an internal space.

FIG. 39 is a plan view illustrating a PCB unit having an internal space.

Referring to FIG. 39, the PCB unit 310 has an R-FPCB format in which the RPCB 311 and the FPCB 312 are integrated as one, and the internal space 313 having the same size as the piezoelectric unit 110 is provided at the center part of the RPCB 311. The conductive through hole 330 is located at one side of the internal space 313, and is also located at the other side of the internal space so that the first line unit or the ground line unit 321a can be defined at both sides of the internal space 313. As described above, the conductive through hole 330 is formed over conductive lines, one conductive line and the other conductive line are arranged to cross each other so as to perform channel division. In addition, the conductive line part printed on the front surface of the PCB unit 210 may have a larger thickness than the remaining parts.

If the PCB unit 310 is formed, the PCB unit 310 is bonded to the front surface of the backing layer 150 in operation 833. The piezoelectric unit 110 is bonded to the internal space of the PCB unit 310 in operation 834.

Figure 40:
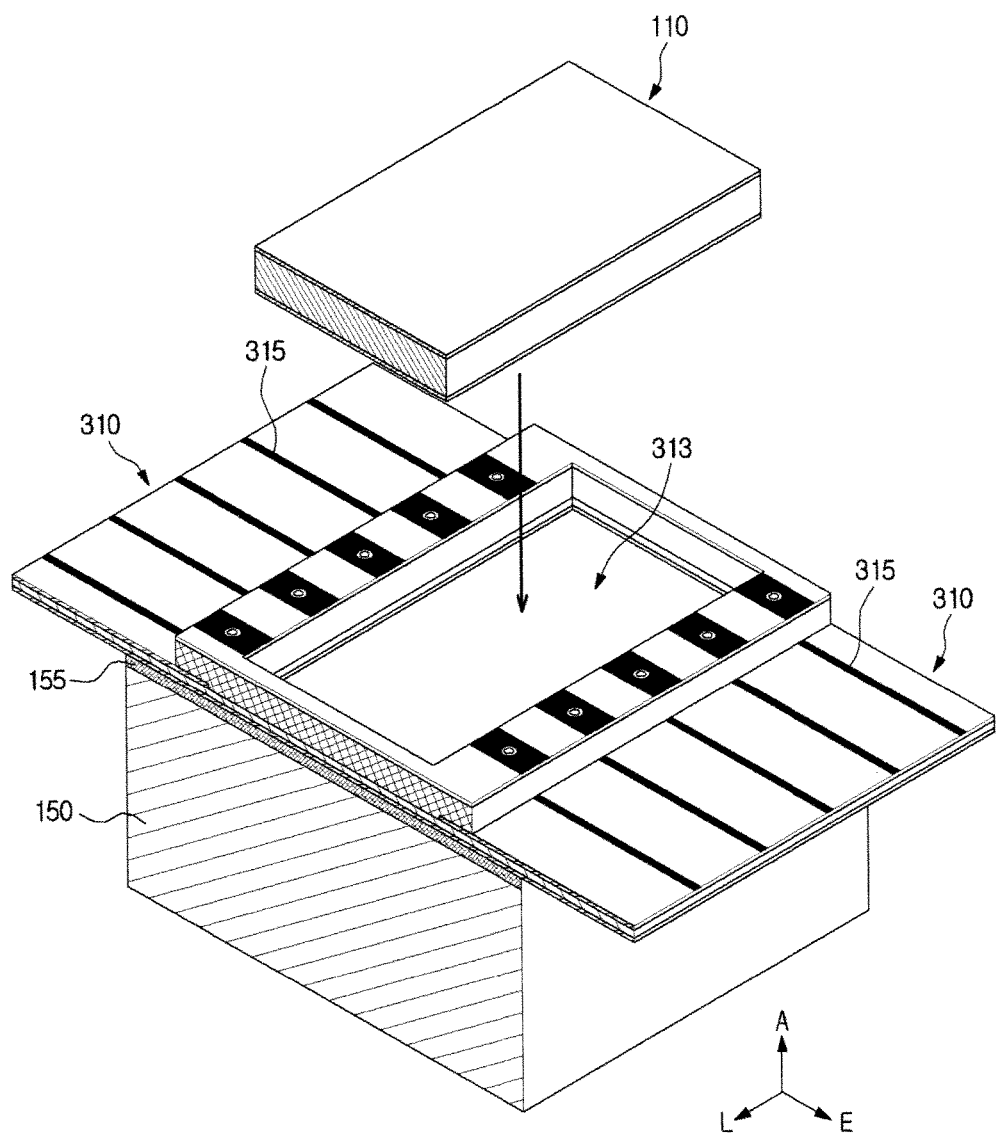
FIG. 40 illustrates another example for bonding a PCB unit 310 and a piezoelectric unit to a backing layer.

FIG. 40 illustrates another method for bonding the PCB unit 310 and the piezoelectric unit to the backing layer.

Referring to FIG. 40, the electrode layer 155 is formed by depositing a conductive material, such as gold, silver, or copper on the front surface of the backing layer 150. The PCB unit 310 is bonded to the front surface of the backing layer 150 including the electrode layer 155. If the backing layer 150 is formed of a conductive material, the electrode layer 155 may be omitted. Here, the PCB unit 310 may be directly bonded to the backing layer 150.

The PCB unit 310 may be bonded to the front surface of the backing layer 150 without execution of the spacing adjustment process shown in operation 813. In addition, the internal space 313 of the PCB unit 310 may have the same size as the piezoelectric unit 110, so that the piezoelectric unit 110 is bonded to be meshed with the internal space 313 of the PCB unit 310.

The bonding (or attachment) of the PCB unit 310 or the bonding (or attachment) of the piezoelectric unit 110 may be achieved through an adhesive. The PCB unit 310 may be bonded to the backing layer 150 through an adhesive. The piezoelectric unit 110 may be bonded to the backing layer 150 and the PCB unit 310 through an adhesive. Here, the adhesive may be formed of a non-conductive material.

If the piezoelectric unit 110 is bonded, the matching layer 160 is bonded to the front surfaces of the piezoelectric unit 110 and the PCB unit 210 in operation 835. The acoustic module including the backing layer 150, the piezoelectric unit 110, the PCB unit 310, and the matching layer 160 is channel-divided through dicing in operation 836. The lens 170 is bonded to the front surface of the channel-divided acoustic module, so that the probe 100 shown in FIG. 26 is formed in operation 837. Prior to bonding of the lens 170, a process for forming at least one of a chemical shield (CS) and a radio frequency (RF) on the front surface of the acoustic module may be further used. The operations 835 to 837 may respectively correspond to the operations 715 to 717, and as such a detailed description thereof will herein be omitted for convenience of description.

Figure 41:
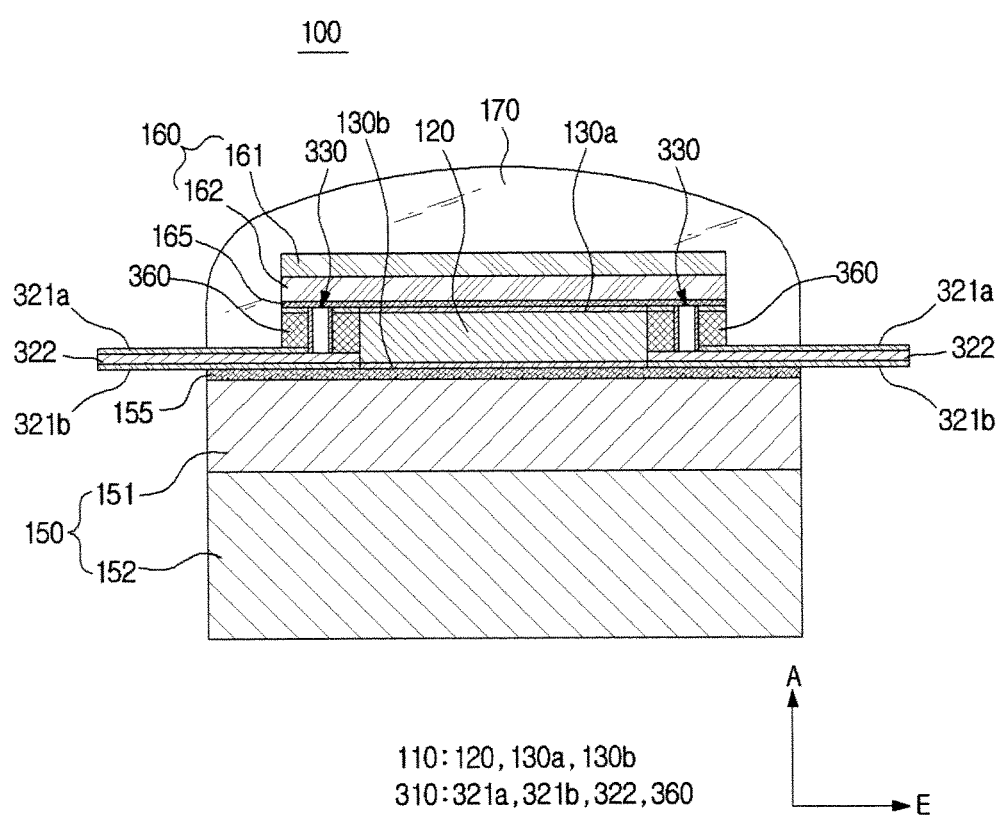
FIG. 41 is a cross-sectional view illustrating a probe for an ultrasonic imaging apparatus according to still another embodiment.

FIG. 41 is a cross-sectional view illustrating a probe for an ultrasonic imaging apparatus according to still another embodiment. For convenience of description, the same or similar structures in conduction and function as those described in the above-mentioned embodiment are denoted by the same reference numerals, and the explanation thereof will be omitted herein.

Referring to FIG. 41, the probe 100 may include a piezoelectric unit 110, a PCB unit 310 provided at a lateral surface of the piezoelectric unit 110, a backing layer 150 provided at a back surface of the piezoelectric unit 110, a matching layer 160 provided at a front surface of the piezoelectric unit 110, and a lens 170. In this case, the piezoelectric unit 110 may include the piezoelectric substance 120 and electrodes (130a, 130b) formed at the front and back surfaces of the piezoelectric substance 120. The PCB unit 310 may have an R-FPCB shape through bonding of the rigid support unit 360, and may have the same height as the piezoelectric unit 110 in response to a thickness variation of the support unit 360. The backing layer 150 includes a plurality of layers, and is arranged at a back surface of the piezoelectric unit 110. As can be seen from FIG. 41, the backing layer 150 may include a first backing layer 151 and a second backing layer 152.

Figure 42:
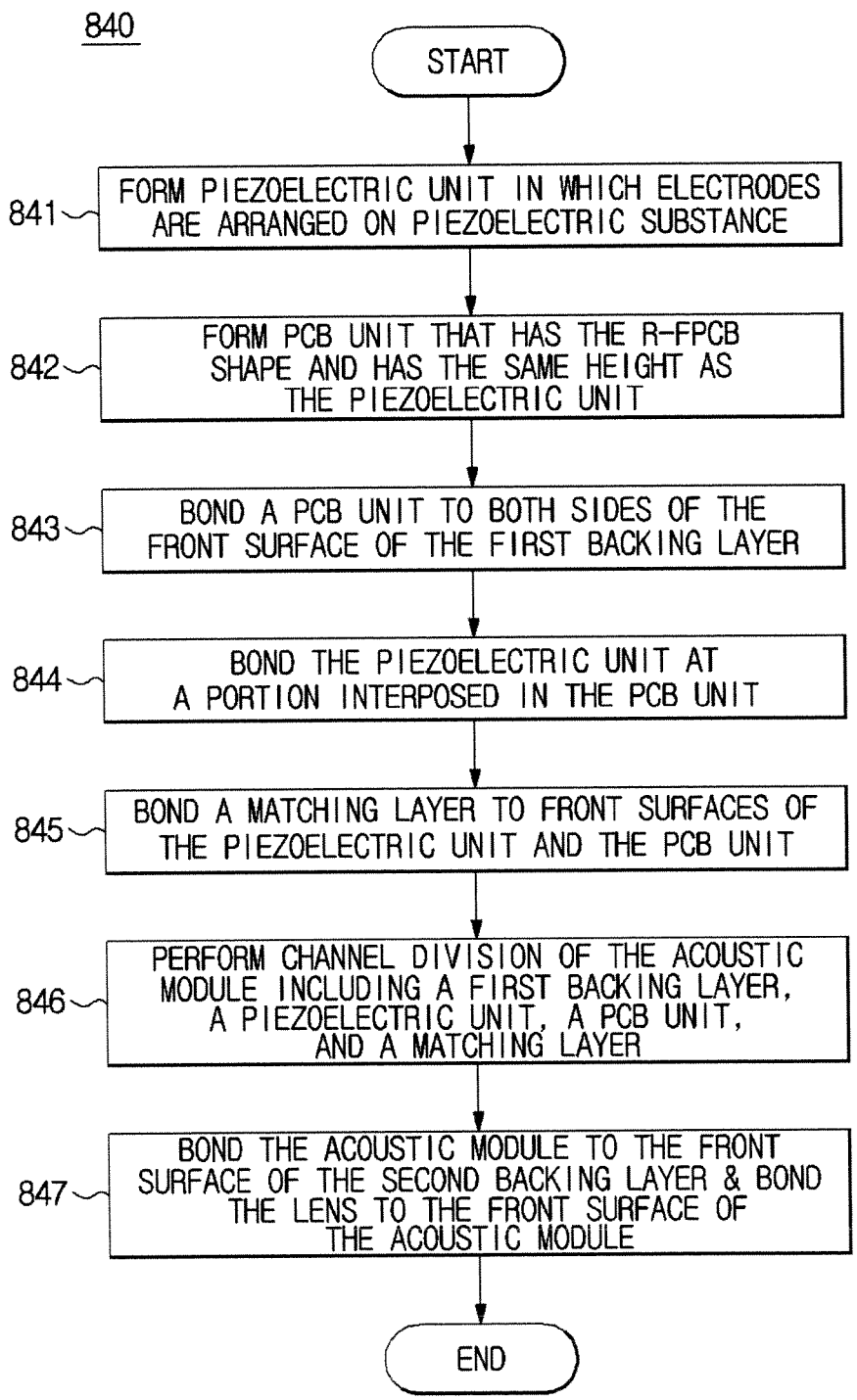
FIG. 42 is a flowchart illustrating a method for manufacturing the probe of the ultrasonic imaging apparatus shown in FIG. 41.
Figure 43:
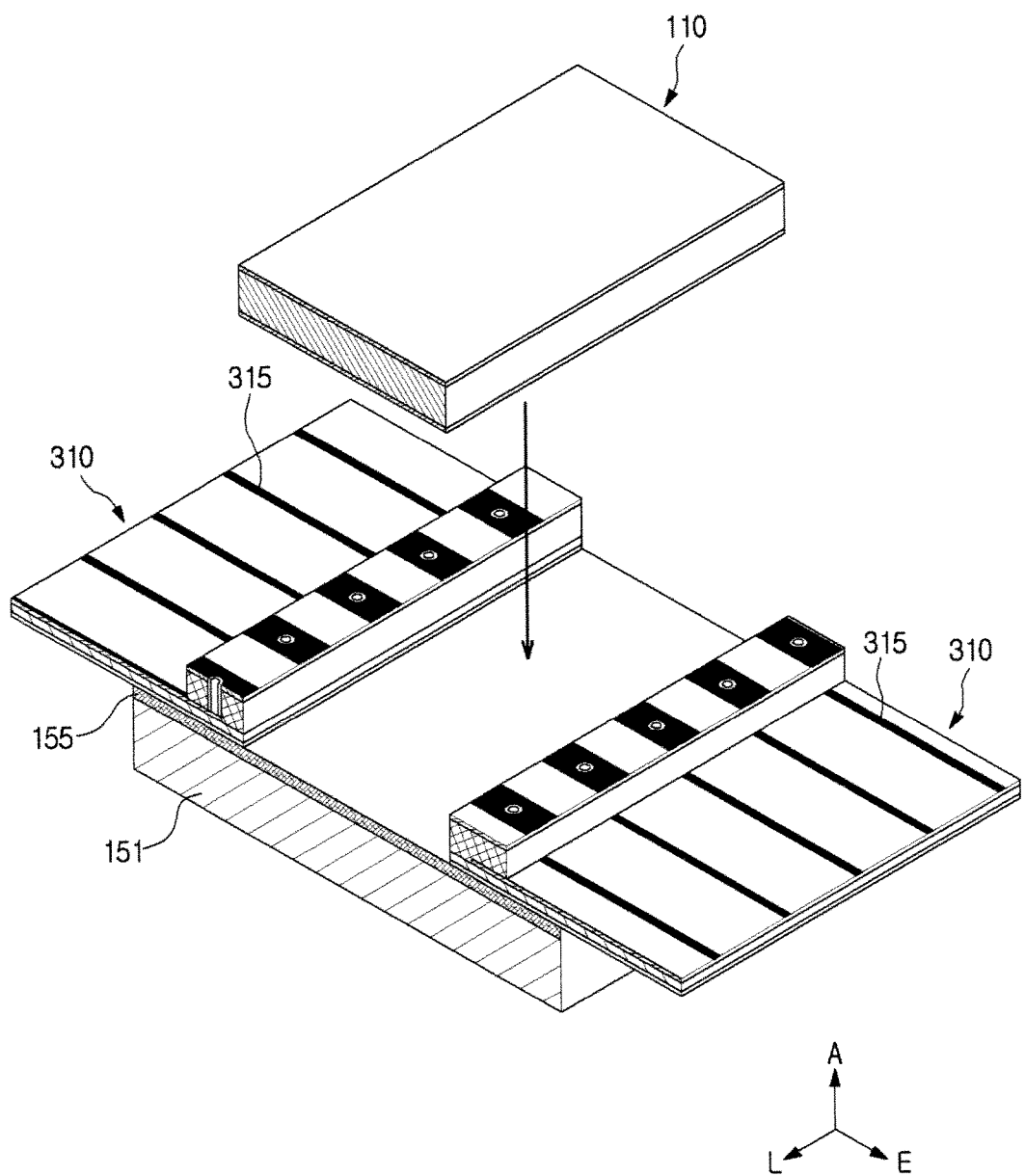
FIG. 43 illustrates an example for bonding a PCB unit 310 and a piezoelectric unit to a first backing layer.
Figure 44:
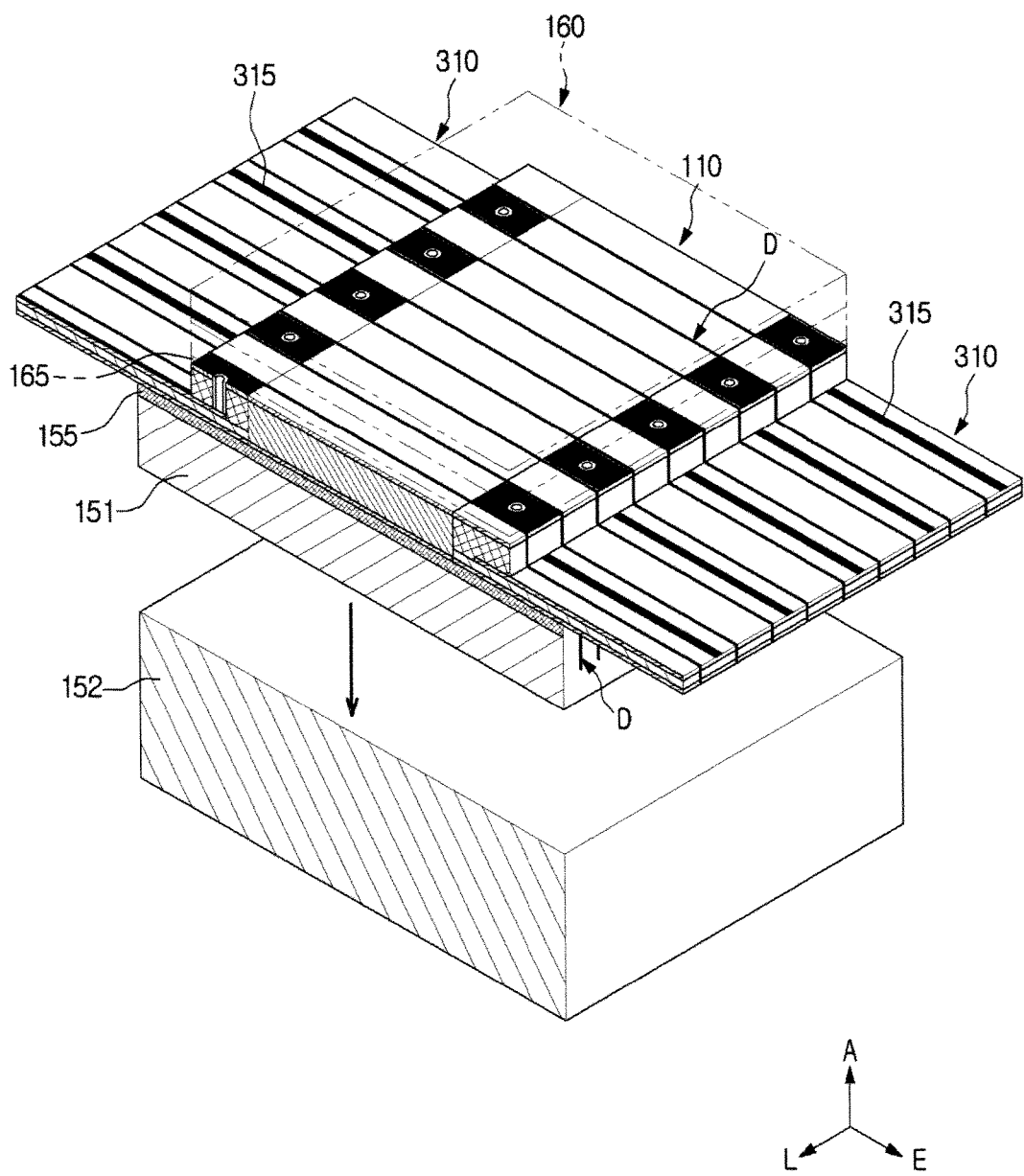
FIG. 44 illustrates an exemplary method for bonding a channel division and acoustic module of the acoustic module to a second backing layer.

FIG. 42 is a flowchart illustrating a method for manufacturing the probe of the ultrasonic imaging apparatus shown in FIG. 41 according to another embodiment. FIGS. 43 and 44 illustrate a method for manufacturing the probe of the ultrasonic imaging apparatus according to the embodiments.

Referring to FIG. 42, the piezoelectric unit 110 in which electrodes are arranged on the piezoelectric substance 120 is formed in operation 841. Thereafter, the PCB unit 310 having an R-FPCB format is formed to have the same height as the piezoelectric unit 110 in operation 842. The operations 841 and 842 may respectively correspond to the operations 811 and 812, and as such a detailed description thereof will herein be omitted for convenience of description.

If the PCB unit 310 is formed, the PCB unit 310 is bonded to both sides of the front surface of the first backing layer 151 in operation 843. The piezoelectric unit 110 is bonded between the PCB units 310 in operation 844.

FIG. 43 illustrates an exemplary method for bonding the PCB unit 310 and the piezoelectric unit to the backing layer.

Referring to FIG. 43, by depositing a conductive material, such as gold, silver, or copper on the front surface of the first backing layer 151, the electrode layer 155 is formed. The PCB unit 310 (구슬은 210, 확인요망) is bonded to both sides of the front surface of the first backing layer 151 including the electrode layer 155. If the first backing layer 151 is formed of a conductive material, the electrode layer 155 may be omitted. Here, the PCB unit 210 may be directly bonded to the first backing layer 151.

The first backing layer 151 may have a larger width than the piezoelectric unit 110, and one PCB unit 310 may be bonded to each of one side and the other side of the front surface of the first backing layer 151 on the basis of a predetermined interval corresponding to the width of the piezoelectric unit 110. In this case, the conductive line 315 of the PCB unit 310 bonded to the one side and the conductive line 315 of the PCB unit 310 bonded to the other side are arranged to cross each other. The piezoelectric unit 110 is bonded to be meshed with the spacing formed by the PCB unit 310.

The bonding (or attachment) of the PCB unit 310 or the bonding (or attachment) of the piezoelectric unit 110 may be achieved through an adhesive. The piezoelectric unit 110 may be bonded to the first backing layer 151 and the PCB unit 310 through an adhesive. Here, the adhesive may be formed of a non-conductive material.

In accordance with the bonding between the PCB unit 310 and the piezoelectric unit 110, a first electrode 130a serving as a ground electrode of the piezoelectric unit 110 is connected to the first line unit 321a so as to form a line unit for grounding, and a second electrode 130b serving as a signal electrode is connected to the second line unit 321b so as to form a line unit for signaling.

If the piezoelectric unit 110 is bonded, the matching layer 160 is bonded to the front surfaces of the piezoelectric unit 110 and the PCB unit 210, the acoustic module is formed in operation 845. In this case, the acoustic module may be defined as a module formed by bonding of the matching layer 160. The acoustic module may be defined as a module that is formed by bonding of the first backing layer 151, the piezoelectric unit 110, the PCB unit 210, and the matching layer 160.

The acoustic module including the first backing layer 151, the piezoelectric unit 110, the PCB unit 310, and the matching layer 160 may be channel-divided through dicing in operation 846. The acoustic module is bonded to the front surface of the second backing layer 152 in operation 846.

FIG. 44 illustrates an exemplary method for bonding a channel division and acoustic module of the acoustic module to the second backing layer.

Referring to FIG. 44, each of both PCB units 310 (i.e., one PCB unit 310 bonded to one side of the front surface of the first backing layer 151 and the other PCB unit 310 bonded to the other side of the front surface of the first backing layer 151) may include a plurality of conductive lines 315 spaced apart from each other by a predetermined distance. Here, the conductive line 315 of the PCB unit 310 bonded to one side and the other conductive line 315 of the PCB unit 310 bonded to the other side may be arranged to cross each other.

Channel division may be achieved considering that both conductive lines 315 are arranged to cross each other. In more detail, such dicing may be achieved along a specific line D disposed between one conductive line 315 provided at one side and the other conductive line 315 arranged at the other side. The conductive line 315 provided at one side and the other conductive line 315 provided at the other side may form a plurality of arrays, and may be electrically isolated from each other.

In order to reliably isolate among the matching layer 160, the piezoelectric unit 110, and the PCB unit 310, the matching layer 160, the piezoelectric unit 110, the PCB unit 310, and the first backing layer 151 may be diced to a predetermined depth.

Although the acoustic module can be channel-divided through dicing, the scope or spirit of the present invention is not limited thereto, and channel division may also be achieved using an arbitrary method (e.g., etching, photolithographic pattering, etc.) known to those skilled in the art.

If channel division is achieved, the channel-divided acoustic module may be bonded to the front surface of the second backing layer 152. The acoustic module is modified in shape in response to the shape of the second backing layer 152, and is then bonded to the second backing layer 152. For example, differently from FIG. 44, if the second backing layer 152 has a curved shape, the back surface of the acoustic module is bended in response to the curvature of the second backing layer 152, and the bended acoustic module is bonded to the front surface of the second backing layer 152.

Thereafter, the lens is bonded to the front surface of the acoustic module, and the probe 100 shown in FIG. 41 is formed in operation 847. Prior to bonding of the lens 170, a process for forming at least one of a chemical shield (CS) and a radio frequency (RF) on the front surface of the acoustic module may be further used.

Figure 45:
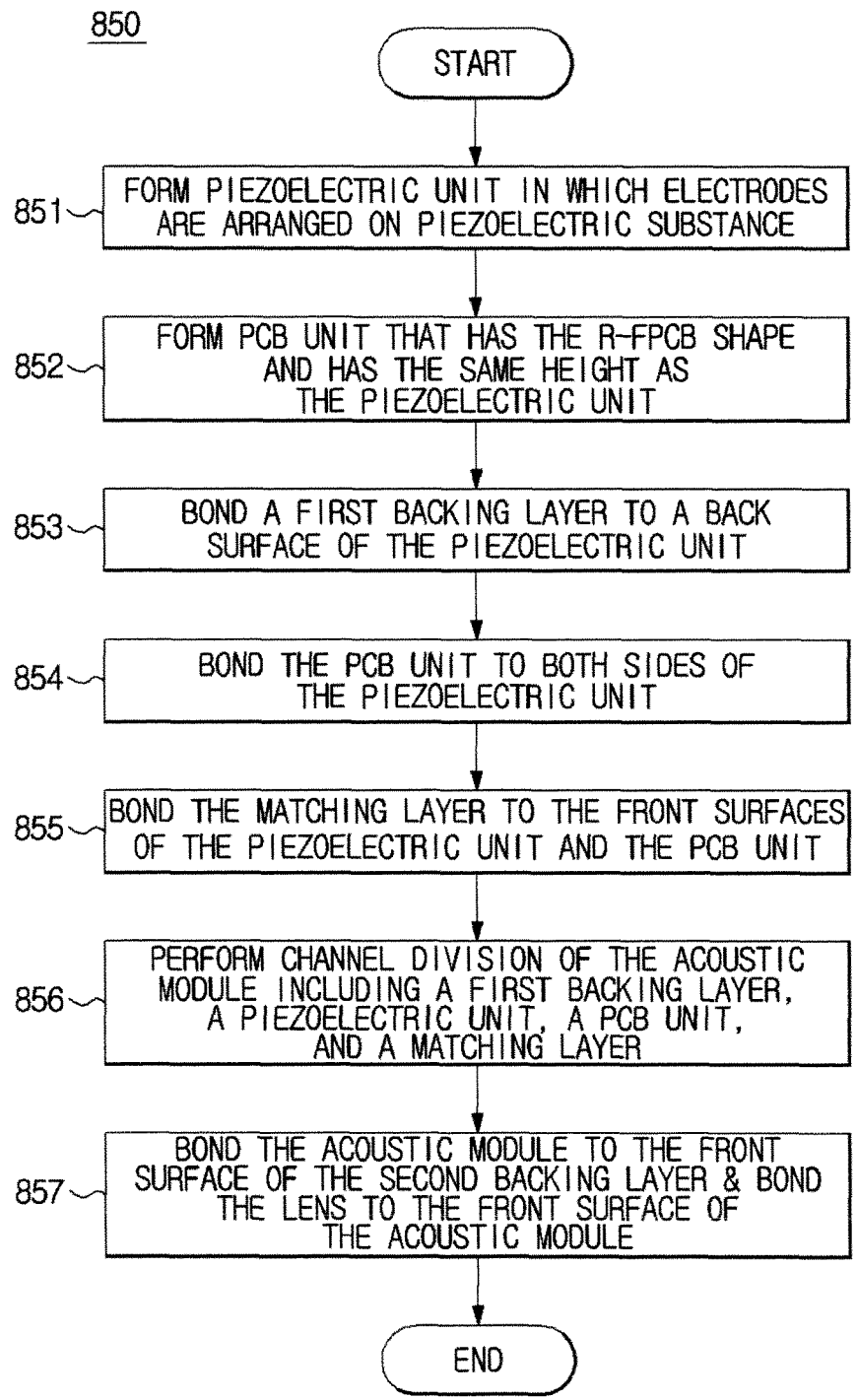
FIG. 45 is a flowchart illustrating a method for manufacturing the probe of the ultrasonic imaging apparatus shown in FIG. 41.

FIG. 45 is a flowchart illustrating a method for manufacturing the probe of the ultrasonic imaging apparatus shown in FIG. 41 according to another embodiment.

Referring to FIG. 45, the piezoelectric unit 110 in which electrodes are arranged on the piezoelectric substance 120 is formed in operation 851. Thereafter, the PCB unit 310 having an R-FPCB format is formed to have the same height as the piezoelectric unit 110 in operation 852. Operations 851 and 852 may respectively correspond to the operations 811 and 812.

If the PCB unit 310 is formed, the first backing layer 151 may be bonded to the back surface of the piezoelectric unit 110, or the piezoelectric unit 110 may be bonded to the front surface of the first backing layer 151 in operation 853. The piezoelectric unit 310 is bonded to both sides of the piezoelectric unit 110 in operation 854.

Figure 46:
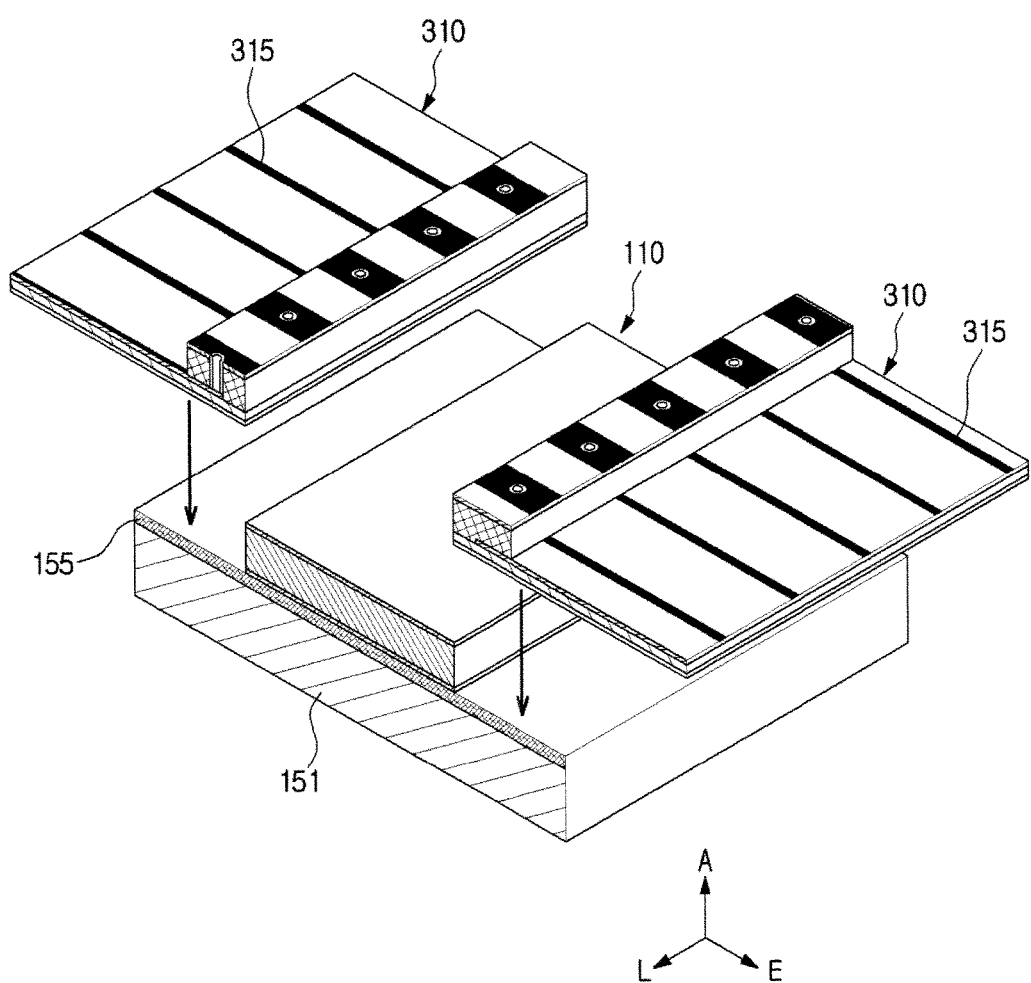
FIG. 46 illustrates another example for bonding a PCB unit 310 and a piezoelectric unit to a first backing layer.

FIG. 46 illustrates a method for bonding the PCB unit 310 and the piezoelectric unit to the first backing layer.

Referring to FIG. 46, by depositing a conductive material, such as gold, silver, or copper on the front surface of the first backing layer 151, the electrode layer 155 is formed. The piezoelectric unit 110 is bonded to the front surface of the first backing layer 151 including the electrode layer 155. If the first backing layer 151 is formed of a conductive material, the electrode layer 155 may be omitted. Here, the piezoelectric unit 110 may be directly bonded to the first backing layer 151.

The first backing layer 151 may have a larger width than the piezoelectric unit 110, and the piezoelectric unit 110 is bonded to be located at the center part of the front surface of the first backing layer 151. The PCB unit 310 may be bonded to each of one side and the other side of the piezoelectric unit 110. In this case, the conductive line 315 of the PCB unit 310 bonded to the one side and the conductive line 315 of the PCB unit 310 bonded to the other side are arranged to cross each other.

The bonding (or attachment) of the piezoelectric unit 110 or the bonding (or attachment) of the PCB unit 310 may be achieved through an adhesive. The piezoelectric unit 110 may be bonded to the first backing layer 151 through an adhesive. The PCB unit 310 may be bonded to the first backing layer 151 and the PCB unit 310 through an adhesive. Here, the adhesive may be formed of a non-conductive material.

In accordance with the bonding between the PCB unit 310 and the piezoelectric unit 110, a first electrode 130a serving as a ground electrode of the piezoelectric unit 110 is connected to the first line unit 321a so as to form a line unit for a grounding part, and a second electrode 130b serving as a signal electrode is connected to the second line unit 321b so as to form a line unit for a signaling part.

If the PCB unit 310 is bonded, the matching layer 160 is bonded to the front surfaces of the piezoelectric unit 110 and the PCB unit 210 in operation 855. The acoustic module including the first backing layer 151, the piezoelectric unit 110, the PCB unit 310, and the matching layer 160 is channel-divided through dicing in operation 856. The lens 170 is bonded to the front surface of the channel-divided acoustic module in operation 857. Prior to bonding of the lens 170, a process for forming at least one of a chemical shield (CS) and a radio frequency (RF) on the front surface of the acoustic module may be further used. The operations 855 to 857 may respectively correspond to the operations 845 to 847, and as such a detailed description thereof will herein be omitted for convenience of description.

Although the above-mentioned description has exemplarily disclosed that a process (i.e., operation 852) for forming the PCB unit 310 is performed prior to the process (i.e., operation 853) for bonding the piezoelectric unit 110 to the first backing layer 151, it should be noted that the process (i.e., operation 852) for forming the PCB unit 310 can also be achieved after the process (i.e., operation 853) for bonding the piezoelectric unit 110 to the first backing layer 151.

Figure 47:
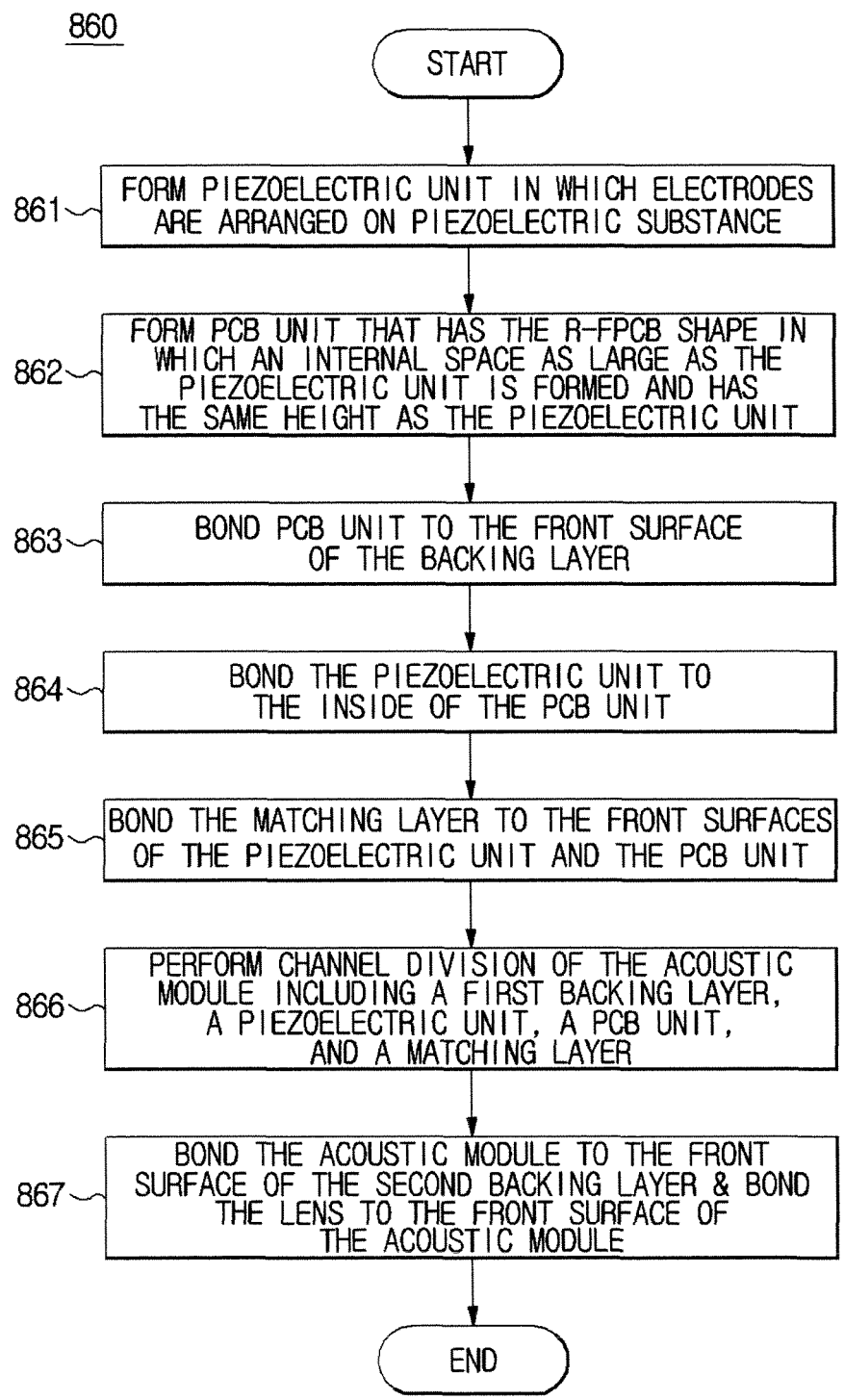
FIG. 47 is a flowchart illustrating a method for manufacturing the probe of the ultrasonic imaging apparatus shown in FIG. 41.

FIG. 47 is a flowchart illustrating a method for manufacturing the probe of the ultrasonic imaging apparatus shown in FIG. 41.

Referring to FIG. 47, the piezoelectric unit 110 in which electrodes are arranged in the piezoelectric substance 120 is formed in operation 861.

The operation 831 may correspond to the operation 811, and as such a detailed description thereof will herein be omitted for convenience of description. Thereafter, the PCB unit 310 includes an R-FPCB in which an internal space as large as the piezoelectric unit 110 is formed, and the PCB unit 310 having the same height as the piezoelectric unit 110 in operation 862. Operations 861 and 862 may respectively correspond to the operations 831 and 832, and as such a detailed description thereof will herein be omitted for convenience of description.

If the PCB unit 310 is formed, the PCB unit 310 is bonded to the front surface of the first backing layer 151 in operation 863. The piezoelectric unit 110 is bonded to the internal space of the PCB unit 310 in operation 864.

Figure 48:
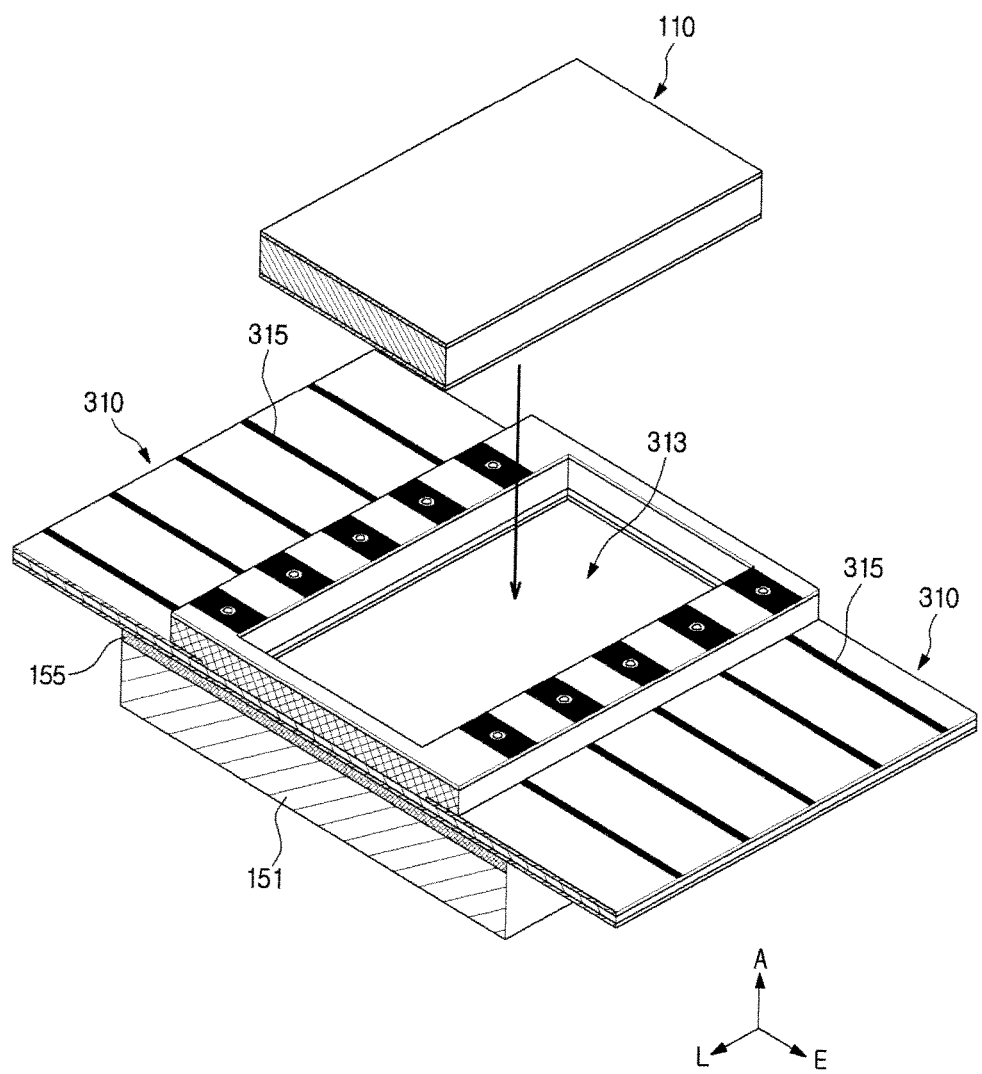
FIG. 48 is a flowchart illustrating another example for bonding a PCB unit 310 and a piezoelectric unit to a first backing layer.

FIG. 48 illustrates another method for bonding the PCB unit 310 and the piezoelectric unit to the first backing layer.

Referring to FIG. 48, the electrode layer 155 is formed by depositing a conductive material, such as gold, silver, or copper on the front surface of the first backing layer 151. The PCB unit 310 is bonded to the front surface of the backing layer 150 including the electrode layer 155. If the backing layer 150 is formed of a conductive material, the electrode layer 155 may be omitted. Here, the PCB unit 310 may be directly bonded to the backing layer 150.

The PCB unit 310 may be bonded to the front surface of the first backing layer 151 without execution of the spacing adjustment process shown in operation 813. In addition, the internal space 313 of the PCB unit 310 may have the same size as the piezoelectric unit 110, so that the piezoelectric unit 110 is bonded to be meshed with the internal space 313 of the PCB unit 310.

The bonding (or attachment) of the PCB unit 310 or the bonding (or attachment) of the piezoelectric unit 110 may be achieved through an adhesive. The PCB unit 310 may be bonded to the first backing layer 151 through an adhesive. The piezoelectric unit 110 may be bonded to the first backing layer 151 and the PCB unit 310 through an adhesive. Here, the adhesive may be formed of a non-conductive material.

If the piezoelectric unit 110 is bonded, the matching layer 160 is bonded to the front surfaces of the piezoelectric unit 110 and the PCB unit 310 in operation 855. The acoustic module including the first backing layer 151, the piezoelectric unit 110, the PCB unit 310, and the matching layer 160 is channel-divided through dicing in operation 856. The lens 170 is bonded to the front surface of the channel-divided acoustic module, so that the probe 100 shown in FIG. 41 is formed in operation 857. Prior to bonding of the lens 170, a process for forming at least one of a chemical shield (CS) and a radio frequency (RF) on the front surface of the acoustic module may be further used. The operations 855 to 857 may respectively correspond to the operations 815 to 817, and as such a detailed description thereof will herein be omitted for convenience of description.

Figure 49:
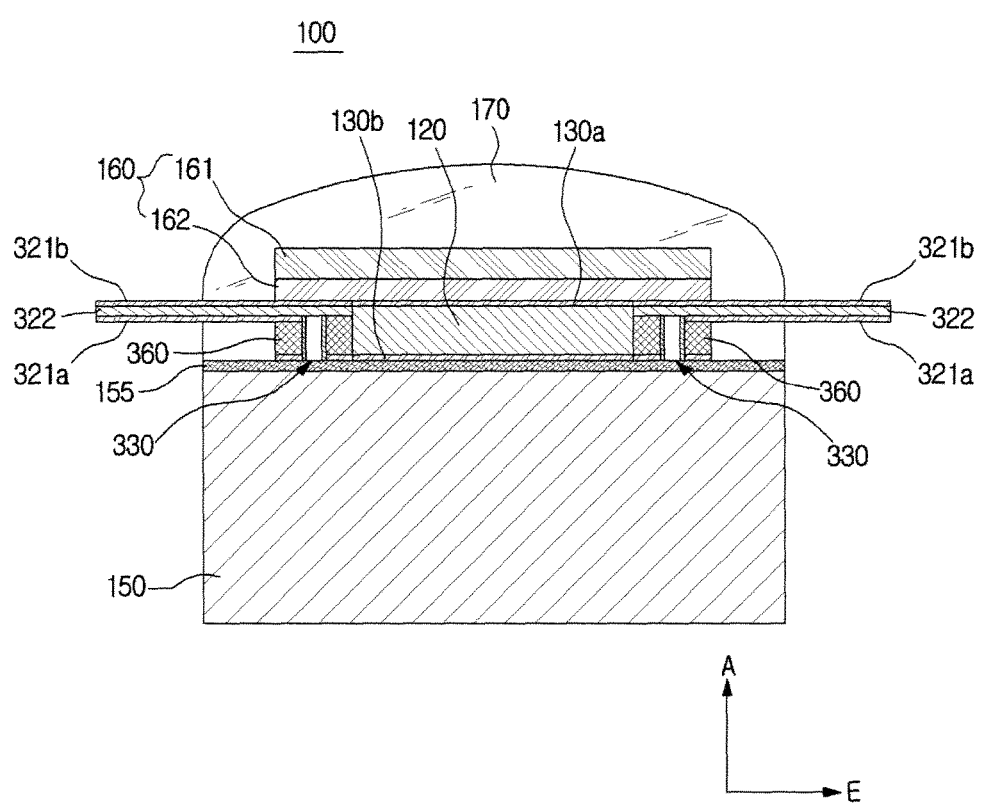
FIG. 49 is a cross-sectional view illustrating a probe for an ultrasonic imaging apparatus according to still another embodiment.

FIG. 49 is a cross-sectional view illustrating a probe for an ultrasonic imaging apparatus according to still another embodiment.

Referring to FIG. 49, the PCB unit 310 may have an R-FPCB shape through bonding of the rigid support unit 360, and include a double-sided PCB in which a second line unit 321b and a first line unit 321a are respectively provided at the front surface and the back surface of the PCB unit 310 while being spaced apart from each other by the insulation unit 322 interposed therebetween. In other words, the front surface and the back surface of the PCB unit 310 may be replaced with each other as shown in FIG. 16, and a conductive through hole 330 may be arranged in a backward direction.

Since the PCB unit 3310 is arranged at a lateral surface of the piezoelectric unit 110, the first line unit 221a is connected to a second electrode 130b acting as a signal electrode so that the first line unit 221a may be used as a line unit for signaling, and the second line unit 220b is connected to a first electrode 130a acting as aground electrode so that the second line unit 220b may be used as a line unit for grounding.

Although FIG. 49 has exemplarily disclosed that the electrode layers (155, 165) are contained in the PCB unit 310 for convenience of description and better understanding of the present invention, if the backing layer 150 or the matching layer 160 is formed of a conductive material, the electrode layers (155, 165) may be omitted herein.

FIG. 50 is a cross-sectional view illustrating a probe for an ultrasonic imaging apparatus according to still another embodiment.

Referring to FIG. 50, the PCB unit 310 of the probe 100 may have an R-FPCB shape through bonding of the rigid support unit 360. The PCB unit 310 may be a double-sided PCB in which a first line unit 321a and a second line unit 321b are respectively provided at the front surface and the back surface of the PCB unit 310 while being spaced apart from each other by the insulation unit 322 interposed therebetween. In other words, the front surface and the back surface of the PCB unit 310 may be replaced with each other as shown in FIG. 26, and a conductive through hole 330 may be arranged in a backward direction.

The probe 100 may include a backing layer 150 composed of a plurality of layers. For example, the backing layer 150 may include a first backing layer 151 and a second backing layer 152. The first backing layer 151 may be thinner than the second backing layer 152. Differently from FIG. 60, the first backing layer 151 is formed in a block shape, the second backing layer 152 has a curved shape having a curvature, and the first backing layer 151 and the second backing layer 152 may be formed to have different shapes. The arrangement shape of the piezoelectric substance 120 may be determined according to the shapes of the first backing layer 151 and the second backing layer 152, and the shape and category of the probe 100 may also be determined.

As is apparent from the above description, a probe for the ultrasonic imaging apparatus and a method for manufacturing the same according to the embodiments can reduce a variation of ultrasonic acoustic characteristics caused by a printed circuit board (PCB) because the PCB is not arranged among a piezoelectric substance, a matching layer, and a backing layer. In addition, a PCB is provided at a lateral surface of the piezoelectric substance, so that strength against impact can be increased either during channel division based on dicing or during the usage time of a probe. In addition, a single crystal (monocrystal) may be used as a piezoelectric substance or the like, such that a probe having a large bandwidth can be formed, and low-frequency ultrasonic signals and high-frequency ultrasonic signals can be transmitted and received. In addition, the embodiments of the present invention can easily perform channel division of the acoustic module, and can make the divided acoustic module using a curvature, such that the embodiments of the present invention can be applied to various technical fields without being limited to the shapes of probes.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A probe for an ultrasonic imaging apparatus comprising:
   a piezoelectric unit including a piezoelectric substance and an electrode;
   a printed circuit board (PCB) unit having a printed circuit board (PCB) and a support unit supporting the PCB, disposed at a lateral surface of the piezoelectric unit;
   a matching layer disposed at front surfaces of the piezoelectric unit and the PCB unit; and
   a backing layer disposed at a back surface of the piezoelectric unit and the PCB unit,
   wherein the height of the PCB unit is determined based on a thickness of the support unit, the PCB includes a flexible printed circuit board (FPCB), the support unit is a rigid support unit, the PCB unit has a rigid-flexible printed circuit board (R-FPCB) shape having the rigid support unit and the FPCB bonded, and the support unit is sandwiched by the PCB unit.

2. The probe according to claim 1, wherein the PCB unit is disposed at both lateral surfaces of the piezoelectric unit on the basis of the piezoelectric unit inserted into the PCB unit.

3. The probe according to claim 2, wherein a spacing between one PCB unit disposed at one side of the piezoelectric unit and another PCB unit disposed at another side thereof is formed to correspond to an elevation-directional width of the piezoelectric unit.

4. The probe according to claim 2, wherein the PCB unit is formed to have the same height as an axial-directional height of the piezoelectric unit.

5. The probe according to claim 1, wherein the PCB unit has the same height as an axial-directional height of the piezoelectric unit on the basis of a thickness of the support unit.

6. The probe according to claim 1, wherein the PCB unit has a folded shape in a manner that one end of the FPCB encloses the support unit.

7. The probe according to claim 1, wherein the R-FPCB includes an internal space corresponding to a size of the piezoelectric unit.

8. The probe according to claim 7, wherein the piezoelectric unit is bonded to the internal space.

9. The probe according to claim 1, wherein the PCB unit includes a line electrically connected to the electrode.

10. The probe according to claim 9, wherein: the line includes a plurality of lines, wherein the plurality of lines is arranged to be spaced apart from each other by a predetermined distance in a lateral direction.

11. The probe according to claim 10, wherein the plurality of lines arranged at one side of the piezoelectric unit and the plurality of lines arranged at side thereof are arranged to cross each other.

12. The probe according to claim 11, wherein the piezoelectric unit and the PCB unit are configured to form channel division in a lateral direction on the basis of the arrangement of the lines.

13. The probe according to claim 9, wherein the PCB unit further includes a conductive through hole electrically connected to lines disposed on a front surface of the PCB unit.

14. The probe according to claim 12, wherein the conductive through hole is bonded to the support unit or is formed to pass through the support unit.

15. The probe according to claim 1, wherein at least one of the matching layer and the backing layer includes a conductive material.

16. The probe according to claim 1, further comprising: at least one electrode layer configured to electrically connect the electrode to the PCB.

17. The probe according to claim 1, wherein the backing layer includes a plurality of backing layers.

18. The probe according to claim 2, wherein: the PCB unit is bonded to the piezoelectric unit through an adhesive, wherein the adhesive is formed of a non-conductive material.

19. A probe for an ultrasonic imaging apparatus comprising:

a piezoelectric unit including a piezoelectric substance and an electrode;

a printed circuit board (PCB) unit having a printed circuit board (PCB) and a support unit supporting the PCB, disposed at a lateral surface of the piezoelectric unit;

a matching layer disposed at front surfaces of the piezoelectric unit and the PCB unit; and a backing layer disposed at a back surface of the piezoelectric unit and the PCB unit, wherein the height of the PCB unit is determined based on a thickness of the support unit, the PCB includes a flexible printed circuit board (FPCB), the support unit is a rigid support unit, the PCB unit has a rigid-flexible printed circuit board (R-FPCB) shape having the rigid support unit and the FPCB bonded, the PCB unit further comprises a first line unit, a second line unit, and an insulation unit disposed between the first line unit and the second line unit, and the height of the PCB unit is determined based on thicknesses of the support unit, the first line unit, the second line unit, and the insulation unit.

20. The probe according to claim 19, wherein the height of the PCB unit, which is determined based on a sum of the thicknesses of the support unit, the first line unit, the second line unit, and the insulation unit, is equal to an axial-directional height of the piezoelectric unit.

* * * * *